United States Patent
Holmquist et al.

(10) Patent No.: US 9,625,477 B2
(45) Date of Patent: *Apr. 18, 2017

(54) VITAMIN D METABOLITE DETERMINATION UTILIZING MASS SPECTROMETRY FOLLOWING DERIVATIZATION

(75) Inventors: Brett Holmquist, Mission Viejo, CA (US); Nigel Clarke, Oceanside, CA (US); Richard E. Reitz, San Clemente, CA (US)

(73) Assignee: Quest Diagnostics Invstments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/287,012

(22) Filed: Nov. 1, 2011

(65) Prior Publication Data
US 2012/0115242 A1 May 10, 2012

Related U.S. Application Data

(63) Continuation of application No. 13/115,935, filed on May 25, 2011, now Pat. No. 8,076,157, which is a continuation of application No. 12/630,790, filed on Dec. 3, 2009, now Pat. No. 7,977,117.

(51) Int. Cl.
G01N 24/00 (2006.01)
G01N 33/82 (2006.01)
G01N 30/72 (2006.01)
G01N 30/88 (2006.01)

(52) U.S. Cl.
CPC ......... *G01N 33/82* (2013.01); *G01N 30/7233* (2013.01); *G01N 2030/8813* (2013.01); *Y10T 436/203332* (2015.01); *Y10T 436/24* (2015.01)

USPC ........................................................ 436/173

(58) Field of Classification Search
CPC ............. G01N 33/82; G01N 30/7233; G01N 2030/8813; Y10T 436/24; Y10T 436/203332
USPC ........................................................ 436/173
See application file for complete search history.

(56) References Cited

U.S. PATENT DOCUMENTS

| | | |
|---|---|---|
| 4,332,591 A | 6/1982 | Oi et al. |
| 5,772,874 A | 6/1998 | Quinn et al. |
| 5,795,469 A | 8/1998 | Quinn et al. |
| 5,916,523 A | 6/1999 | Yan et al. |
| 5,919,368 A | 7/1999 | Quinn et al. |
| 5,968,367 A | 10/1999 | Quinn et al. |
| 6,107,623 A | 8/2000 | Bateman et al. |
| 6,124,137 A | 9/2000 | Hutchens et al. |

(Continued)

FOREIGN PATENT DOCUMENTS

| | | |
|---|---|---|
| JP | 07-027763 | 1/1995 |
| JP | 2002-518474 | 6/2002 |

(Continued)

OTHER PUBLICATIONS

Aronov et al., Anal. Bioanal. Chem. (2008) 391:1917-1930.*

(Continued)

*Primary Examiner* — Jill Warden
*Assistant Examiner* — Monique Cole
(74) *Attorney, Agent, or Firm* — Quest Diagnostics, Inc.

(57) ABSTRACT

The invention relates to the detection of vitamin D metabolites. In a particular aspect, the invention relates to methods for detecting derivatized vitamin D metabolites by mass spectrometry.

15 Claims, 41 Drawing Sheets

(56) References Cited

U.S. PATENT DOCUMENTS

| | | | |
|---|---|---|---|
| 6,204,500 | B1 | 3/2001 | Whitehouse et al. |
| 6,268,144 | B1 | 7/2001 | Koster |
| 6,787,660 | B1 | 9/2004 | Armbruster et al. |
| 6,977,143 | B1 | 12/2005 | Caulfield et al. |
| 7,019,146 | B1 | 3/2006 | Ishigai et al. |
| 7,087,395 | B1 | 8/2006 | Garrity et al. |
| 7,321,116 | B2 | 1/2008 | Picard et al. |
| 7,348,137 | B2 | 3/2008 | Caulfield et al. |
| 7,473,560 | B2 | 1/2009 | Soldin |
| 7,482,162 | B2 | 1/2009 | Laurie et al. |
| 7,618,827 | B2 | 11/2009 | Steven |
| 7,700,365 | B2 | 4/2010 | Singh et al. |
| 7,745,226 | B2 | 6/2010 | Clarke et al. |
| 7,972,867 | B2 | 7/2011 | Clarke et al. |
| 7,972,868 | B2 | 7/2011 | Holmquist et al. |
| 7,977,117 | B2 * | 7/2011 | Holmquist et al. ........... 436/173 |
| 8,034,627 | B2 | 10/2011 | Holmquist et al. |
| 8,076,157 | B2 * | 12/2011 | Holmquist et al. ........... 436/173 |
| 8,084,269 | B2 | 12/2011 | Holmquist et al. |
| 8,101,427 | B2 | 1/2012 | Clarke et al. |
| 8,173,442 | B2 | 5/2012 | Holmquist et al. |
| 8,431,411 | B2 | 4/2013 | Clarke et al. |
| 8,936,943 | B2 | 1/2015 | Clarke et al. |
| 9,244,084 | B2 | 1/2016 | Clarke et al. |
| 2003/0171605 | A1 | 9/2003 | Reddy et al. |
| 2004/0235193 | A1 | 11/2004 | Soldin |
| 2006/0054807 | A1 | 3/2006 | Picard et al. |
| 2006/0094125 | A1 | 5/2006 | Singh et al. |
| 2006/0228808 | A1 | 10/2006 | Clarke et al. |
| 2006/0228809 | A1 * | 10/2006 | Clarke et al. ................ 436/173 |
| 2006/0236886 | A1 | 10/2006 | Leenders et al. |
| 2006/0263886 | A1 | 11/2006 | Peters et al. |
| 2007/0139956 | A1 | 6/2007 | Sugimoto et al. |
| 2008/0128606 | A1 | 6/2008 | Grant et al. |
| 2008/0241955 | A1 | 10/2008 | Purkayastha et al. |
| 2009/0137056 | A1 | 5/2009 | Holmquist et al. |
| 2011/0133068 | A1 | 6/2011 | Holmquist et al. |
| 2011/0226944 | A1 | 9/2011 | Holmquist et al. |
| 2012/0061562 | A1 | 3/2012 | Holmquist et al. |
| 2014/0127825 | A1 | 5/2014 | Dey et al. |
| 2014/0147878 | A1 | 5/2014 | Herman et al. |

FOREIGN PATENT DOCUMENTS

| | | |
|---|---|---|
| JP | 2005-503534 | 2/2005 |
| JP | 2007515625 A | 6/2007 |
| JP | 2009115724 A | 5/2009 |
| JP | 2009543069 A | 12/2009 |
| WO | WO-95/33279 | 12/1995 |
| WO | WO-96/18618 | 6/1996 |
| WO | WO-99/67211 | 12/1999 |
| WO | WO-02/057797 | 7/2002 |
| WO | WO-2004/002996 | 1/2004 |
| WO | WO-2006/034427 | 3/2006 |
| WO | WO-2006/107339 | 10/2006 |
| WO | WO-2006/107814 | 10/2006 |
| WO | WO-2007/039193 | 4/2007 |
| WO | WO-2007/139956 | 12/2007 |
| WO | 2008005846 A2 | 1/2008 |
| WO | WO-2008/097246 | 8/2008 |
| WO | 2009070594 A1 | 6/2009 |

OTHER PUBLICATIONS

Extended European Search Report dated Dec. 1, 2011 for EP Application No. 11184151.6.
Office Action dated Dec. 27, 2011 in Chinese Application No. 200880124794.5.
US Notice of Allowance dated Feb. 23, 2012 in U.S. Appl. No. 13/117,997.
US Office Action dated Dec. 20, 2011 in U.S. Appl. No. 13/299,212.
US Office Action dated Mar. 13, 2012 in U.S. Appl. No. 13/327,650.
Armas et. al, Vitamin D2 Is Much Less Effective than Vitamin D3 in Humans, J. Clin. Endocrinol. Metab. 89:5387-5391 (2004).
Aronov et al, Metabolic profiling of major vitamin D metabolites using Diels-Alder derivatization and ultra-performance liquid chromatography-tandem mass spectrometry, Anal Bioanal Chem, 2008, 391:1917-1930.
Ascalone et al, Stereospecific determination of amisulpride, a new benzamide derivative, in human plasma and urine by automated solid-phase extraction and liquid chromatography on a chiral column. application to pharmacokinetics, Journal of Chromatography B., 676:95-105, 1996.
Bartolucci, et al., Liquid chromatography tandem mass spectrometric quantitation of sulfamethazine and its metabolites: direct analysis of swine urine by triple quadrupole and by ion trap mass spectrometry, Rapid Commun. Mass Spectrom, 14:967-73 (2000).
Busch, A Glossary for Mass Spectrometry, Mass Spectrometry, 17(65):526-534, 2002.
Capote et al, Identification and determination of fat-soluble vitamins and metabolites in human serum by liquid chromatography/triple quadrupole mass spectrometry with multiple reaction monitoring, Rapid Commun. Mass. Spectrom., 21:1745-1754, 2007.
Coldwell et al, Mass Fragmentographic Assay for 25-Hydroxyvitamin D in Plasma Without Derivatization: Enhanced Sensitivity for Metabolites of Vitamins D2 and D3 After Pre-column Dehydration, Journal of Mass Spectrometry, 30:348-356, (1995).
Coldwell et al, Stable isotope-labeled vitamin D, metabolites and chemical analogs: synthesis and use in mass spectrometric studies, Steroids, 55: 418-432, 1990.
Coldwell et al., Measurement of Vitamins D2 and D3 and Seven Major Metabolites in a Single Sample of Human Plasma Using Gas Chromatography/Mass Spectrometry, Biomedical and Environmental Mass Spectromety, 16:81-85 (1988).
Examination Report dated Sep. 20, 2011 for EP Application No. 08 853 843.4.
Extended Search Report dated Feb. 2, 2009 in EP application 06749272.
Extended Search Report dated Dec. 22, 2010 in EP application 08853843.
Guo et al, Steroid profiles using liquid chromatography-Tandem mass spectrometry with atmospheric pressure photoionization source, Arch Pathol Lab Med., 128: 469-475, 2004.
Higashi et al, Characterization of new conjugated metabolites in bile of rats administered 24,25-dihydroxyvitamin D3 and 25-hydroxyvitamin D3, Steroids, 65(5):281-94 (2000).
Higashi et al, Characterization of urinary metabolites of vitamin D3 in man under physiological conditions using liquid chromatography-tandem mass spectrometry, J Pharm Biomed Anal. 29(5):947-55 (2002).
Higashi et al, Liquid chromatography-tandem mass spectrometric method for the determination of salivary 25-hydroxyvitamin D3: a noninvasive tool for the assessment of vitamin D status, Anal. Bioanal Chem, 2008, 391:229-238.
Higashi et al, Simultaneous Determination of 25-Hydroxyvitamin D2 and 25-Hydroxyvitamin D3 in Human Plasma by Liquid Chromatography-Tandem Mass Spectrometry Employing Derivatization with a Cookson-Type Reagent, Biol Pharm Bull., 24(7):738-43, (2001).
International Preliminary Report on Patentability dated Oct. 9, 2007 in application PCT/US2006/012539.
International Preliminary Report on Patentability dated Jun. 1, 2010 in application PCT/US2008/084709.
International Search Report and Written Opinion dated Jan. 26, 2011 in application PCT/US2010/056461.
International Search Report and Written Opinion dated Jan. 27, 2011 in application PCT/US2010/057627.
International Search Report and Written Opinion dated Feb. 7, 2011 in application PCT/US2010/059765.
International Search Report and Written Opinion dated Feb. 8, 2011 in application PCT/US2010/059746.
International Search Report dated Feb. 24, 2009 in application PCT/US2008/084709.
International Search Report dated Jan. 14, 2011 in PCT/US2010/056886.

(56) References Cited

OTHER PUBLICATIONS

International Search Report dated Jan. 4, 2007 in application PCT/US2006/012539.
International Search Report dated Feb. 11, 2011 in application PCT/US2010/059771.
Interview Summary dated Jan. 28, 2009 in U.S. Appl. No. 11/101,166.
Jemal, High-throughput quantitative bioanalysis by LC/MS/MS, Biomedical Chromatography, 14:422-429, 2000.
Jones et al, Biological activity of I,25-Dihydroxyvitamin D2 in the Chick, Biochemistry, 15(3): 713-716, 1976.
Jones et al, Current understanding of the molecular actions of Vitamin D, Physiological Reviews, 78(4): 1193-1231, 1998.
Jones et al, Vitamin Ds: Metabolites and Analogs, Chapter 2 in Modern Chromatographic Analysis of Vitamins, Third Edition, 2002, 79 pgs.
Kamao et al, C-3 Epimerization of Vitamin D3 metabolites and further metabolism of C-3 epimers, The Journal of Biological Chemistry, 279 (16):15897-15907, (2004).
Kissmeyer et al, Sensitive analysis of 1a,25-dihydroxyvitamin D3 in biological fluids by liquid chromatography-tandem mass spectrometry, J Chromatogr A., 935(1-2):93-103 (2001).
Kobayashi et al, Tandem immunoaffinity chromatography for plasma 1a,25-dihydroxyvitamin D3 utilizing two antibodies having different specificities: A novel and powerful pretreatment tool for 1a,25-dihydroxyvitamin D3 radioreceptor assays, J.Steroid Biochem. Molec. Biol., 54(5/6): 217-226, 1995.
Kobayashi, et al, Production of a group-specific antibody to 1 alpha,25-dihydroxyvitamin D and its derivatives having the 1 alpha,3 beta-dihydroxylated A-ring structure, Steroids, (1994), 59(7):404-11.
Letter from Vicki G. Norton, Ph.D. Partner, Duane Morris LLP, Sep. 4, 2008 (originally cited in an Information Disclosure Statement on Oct. 15, 2008 for U.S. Appl. No. 10/977,121.
Maunsell et al, Routine Isotope-Dilution Liquid Chromatography-Tandem Mass Spectrometry Assay for Simultaneous Measurement of the 25-Hydroxy Metabolites of Vitamins D2 and D3, Clinical Chemistry, 51:9 1683-1690, (2005).
Merchant et al, Recent advancements in surface-enhanced laser desorption/ionization-time of flight-mass spectrometry, Electrophoresis 21:1164-1177 (2000).
Miller et al, Genetic causes of rickets, Current Opinions in Pediatrics, 11:333-339, 1999.
Odrzywolska et al, Convergent Synthesis, Chiral HPLC, and Vitamin D Receptor Affinity of Analogs of 1,25-Dihydroxycholecalciferol, Chirality, 11:249-255, (1999).
Office Action dated Sep. 29, 2009 for EP Application No. 06749272.8.
Polson et al., Optimization of protein precipitation based upon effectiveness of protein removal and ionization effect in liquid chromatography-tandem mass spectrometry, Journal of Chromatography B 785:263-275 (2003).
Robb et al., Atmospheric Pressure Photoionization: An Ionization Method for Liquid Chromatography-Mass Spectrometry. Anal. Chem. 72(15):3653-3659 (2000).
Salm et al., The Quantification of Sirolimus by High-Performance Liquid Chromatography-Tandem Mass Spectrometry and Microparticle Enzyme Immunoassay in Renal Transplant Recipients, Clin. Therapeutics, 22 Supl. B:B71-B85, (2000).
Singh et al, C-3 epimers can account for a significant proportion of total circulating 25-hydroxyvitamin D in infants, complicating accurate measurement and interpretation of vitamin D status, The Journal of Clinical Endocrinology & Metabolism, 91(8): 3055-3061, 2006.
Taylor et al., Simultaneous Quantification of Tacrolimus and Sirolimus, in Human Blood, by High-Performance Liquid Chromatography-Tandem Mass Spectrometry, Therapeutic Drug Monitoring, 22:608-12, (2000).
Tsugawa et al, Determination of 25-hydroxyvitamin D in human plasma using high-performance liquid chromatography-tandem mass spectrometry, Anal. Chem., 77:3001-3007, 2005.
US Notice of Allowance dated Dec. 15, 2009 in U.S. Appl. No. 11/101,166.
US Notice of Allowance dated Mar. 2, 2011 in U.S. Appl. No. 11/386,215.
US Notice of Allowance dated Mar. 3, 2011 in U.S. Appl. No. 11/946,765.
US Notice of Allowance dated May 20, 2011 in U.S. Appl. No. 12/630,790.
US Notice of Allowance dated Jul. 6, 2011 in U.S. Appl. No. 12/630,796.
US Notice of Allowance dated Aug. 19, 2009 for U.S. Appl. No. 11/101,166.
US Notice of Allowance dated Aug. 4, 2011 in U.S. Appl. No. 13/115,935.
US Notice of Allowance dated Aug. 24, 2011 in U.S. Appl. No. 13/165,685.
US Notice of Allowance dated Sep. 16, 2011 in U.S. Appl. No. 13/115,916.
US Office Action dated Apr. 12, 2010 in U.S. Appl. No. 11/386,215.
US Office Action dated Jan. 6, 2011 in U.S. Appl. No. 12/630,790.
US Office Action dated Oct. 8, 2008 in U.S. Appl. No. 11/101,166.
US Office Action dated Oct. 5, 2010 in U.S. Appl. No. 11/386,215.
US Office Action dated Dec. 17, 2010 in U.S. Appl. No. 11/946,765.
US Office Action dated Dec. 17, 2010 in U.S. Appl. No. 12/630,796.
US Office Action dated Jun. 24, 2010 in U.S. Appl. No. 11/946,765.
US Office Action dated Jun. 28, 2010 in U.S. Appl. No. 12/630,790.
US Office Action dated Jun. 29, 2011 in U.S. Appl. No. 13/115,935.
US Office Action dated Jul. 21, 2011 in U.S. Appl. No. 13/165,685.
US Office Action dated Jul. 29, 2011 in U.S. Appl. No. 13/117,997.
US Office Action dated Jul. 7, 2010 in U.S. Appl. No. 12/630,796.
US Office Action dated Aug. 4, 2011 in U.S. Appl. No. 13/115,916.
Vieth et al, Age-related changes in the 25-hydroxyvitamin D versus parathyroid hormone relationship suggest a different reason why older adults require more Vitamin D, The Journal of Clinical Endocrinology & Metabolism, 88(1): 185-191, 2003.
Vieth, Vitamin D supplementation, 25-hydroxyvitamin D concentrations, and safety, Am J Clin Nutr, 69:842-856, 1999.
Vogeser et al, Candidate reference method for the quantification of circulating 25-Hydroxyvitamin D3 by liquid chromatography-tandem mass spectrometry, Clinical Chemistry, 50(8): 1415-1417, (2004).
Vreeken et al, On-line post-column Diels-Alder derivatization for the determination of vitamin D3 and its metabolites by liquid chromatography/thermospray mass spectrometry, Biological Mass Spectrometry, 22:621-632, (1993).
Watson et al, Analysis of Vitamin D and its metabolites using thermospray liquid chromatography/Mass spectrometry, Biomedical Chromatography, 5:153-160, 1991.
Wharton et al, Rickets. The Lancet, 362: 1389-1400, 2003.
Wright et al, Proteinchip surface enhanced laser desorption/ionization (SELDI) mass spectrometry: a novel protein biochip technology for detection of prostate cancer biomarkers in complex protein mixtures, Prostate Cancer and Prostatic Diseases, 2:264-76, (1999).
Yeung et al, Characterization of the Metabolic Pathway of 1,25-Dihydroxy-16-Ene Vitamin D3 in Rat Kidney by On-Line High Performance Liquid Chromatography-Electrospray Tandem Mass Spectrometry, Biochemical Pharmacology, vol. 49, No. 8, pp. 1099-1110, (1995).
Yeung et al, Characterization of vitamin D3 metabolites using continuous-flow fast atom bombardment tandem mass spectrometry and high performance liquid chromatography, Chromatogr, 645(1):115-123 (1993).
Yeung, et al, The role of mass spectrometry in vitamin D research, Mass Spec Reviews, (1995), 14(3):179-194.
Zimmer et al. Comparison of turbulent-flow chromatography with automated solid-phase extraction in 96-well plates and liquid-liquid extraction used as plasma sample preparation techniques for liquid chromatography-tandem mass spectrometry. J Chromatogr A, 854: 23-35 (1999).

(56) References Cited

OTHER PUBLICATIONS

EP Communication issued in European Patent Application No. 08853843.4 and dated May 23, 2012.
International Preliminary Report on Patentability issued for PCT/US2010/059746 on Jun. 12, 2012.
International Preliminary Report on Patentability issued for PCT/US2010/059771 on Jun. 12, 2012.
International Preliminary Report on Patentability issued in PCT/US2010/056886 on Jun. 5, 2012.
International Preliminary Report on Patentability issued in PCT/US2010/057627 on Jun. 5, 2012.
Non-final Office Action issued in U.S. Appl. No. 13/436,651 and mailed Jun. 26, 2012.
Notice of Allowance dated Jun. 12, 2012 in U.S. Appl. No. 13/299,212.
International Preliminary Report on Patentability issued for PCT/US2010/059765 on Jun. 12, 2012.
Bunch, Dustin R. et al., "Development and validation of a liquid chromatography-tandem mass spectrometry assay for serum 25-hydroxyvitamin D2/D3 using a turbulent flow online extraction technology," Clin Chem Lab Med, vol. 47, No. 12, (2009), pp. 1565-1572.
Non-Final Office Action issued in U.S. Appl. No. 12/964,710 dated Oct. 15, 2012.
Notice of Allowance issued in U.S. Appl. No. 13/327,650 dated Dec. 12, 2012.
Office Action dated Dec. 11, 2012 in Japanese Application No. 2010-536134 with English translation.
Notice of Allowance issued in U.S. Appl. No. 13/436,651 dated Oct. 11, 2012 (4 pages).
de Castro, et al., "Determination of vitamin D3 metabolites: state-of-the-art and trends", Journal of Pharmaceutical and Biomedical Analysis, 1999, vol. 20, pp. 1-17.
Final Office Action issued in U.S. Appl. No. 12/964,710 dated Feb. 28, 2013.
Gao, et al., "Sensitivity enhancement in liquid chromatography/atmospheric pressure ionization mass spectrometry using derivatization and mobile phase additives", Journal of Chromatography B, 825, 2005, pp. 98-110.
Hashizume, et al., "Identification of human UDP-glucuronosyltransferases catalyzing hepatic $1\alpha,25$-dihydroxyvitamin D3 conjugation", Biochemical Pharmacology, 2008, vol. 75, pp. 1240-1250.
Higashi, et al., "Application of 4-(4-Nitrophenyl)-1,2,4-triazoline-3,5-dione to Analysis of 25-Hydroxyvitamin D3 in Human Plasma by Liquid Chromatography/Electron Capture Atmospheric Pressure Chemical Ionization-Mass Spectrometry", Analytical Sciences, Jun. 2003, vol. 19, pp. 941-943.
Higashi, et al., "Determination of 24,25-dihydroxyvitamin D3 in human plasma using liquid chromatography-mass spectrometry after derivatization with a Cookson-type reagent", Biomedical Chromatography, 2001, vol. 15, pp. 133-140.
Higashi, et al., "Liquid chromatography-mass spectrometric method combined with derivatization for determination of $1\alpha$-hydroxyvitamin D3 in human plasman", Journal of Chromatography B, 772 (2002), pp. 229-238.
Higashi, et al., "Usefulness of Derivatization in High-Performance Liquid Chromatography/Tandem Mass Spectrometry of Conjugated Vitamin D Metabolites", Analytical Sciences, Jul. 1999, vol. 15, pp. 619-623.
Kamao, et al., "Quantification of fat-soluble vitamins in human breast milk by liquid chromatography-tandem mass spectrometry", Journal of Chromatography B, 2007, vol. 859, pp. 192-200.
Murao, et al., "Ferrocene-based Diels-Alder derivatization for the determination of 1 $\alpha$-hydroxyvitamin D3 in rat plasma by high-performance liquid chromatography-electrospray tandem mass spectrometry", Analytical Biochemistry, 2005, vol. 346, pp. 158-166.
Non-Final Office Action issued by U.S. Appl. No. 13/751,915 dated Mar. 11, 2013.
Non-Final Office Action issued in U.S. Appl. No. 12/964,717 dated Feb. 13, 2013.
Wang, et al., "An Electron-Capture Dienophile Derivatization Agent for Increasing Sensitivity: Determination of a Vitamin D Analog (Ro 24-2090) in Plasma Sample with Liquid Chromatography/Mass Spectrometry", Analytical Biochemistry, 1996, vol. 243, Article No. 0478, pp. 28-40.
Weiskopf, et al., "Examination of structurally selective derivatization of vitamin D3 analogues by electrospray mass spectrometry" Journal of Mass Spectrometry, 2001, vol. 36, pp. 71-78.
Chen et al., "Induction of Apoptosis by Vitamin D2, Ergocalciferol, via Reactive Oxygen Generation, Glutathione Depletion, and Caspase Activation in Human Leukemia Cells", Journal of Food and Chemistry, 2008, 56, 2296-3005.
Decision of Final Rejection dated Apr. 25, 2013 issued in connection with Chinese Application No. 200880124794.5, with English translation.
Office Action dated Jun. 20, 2013 issued in connection with U.S. Appl. No. 13/514,892.
Office Action dated Jun. 27, 2013 issued in connection with U.S. Appl. No. 12/964,717.
U. S. Office Action dated Oct. 8, 2008 in U.S. Appl. No. 11/101,166.
US Notice of Allowance dated Aug. 19, 2009 in U.S. Appl. No. 11/101,166.
EPO Communication pursuant to Article 94(3) EPC issued for European application 11184151.6 dated Feb. 14, 2013.
Aguera A., et al., "One-Year Routine Application of a New Method Based On Liquid Chromatography—Tandem Mass Spectrometry to the Analysis of 16 Multiclass Pesticides in Vegetable Samples," Journal of Chromatography A, 2004, vol. 1045 (1-2), pp. 125-135.
Examiner's Answer to Appeal Brief mailed Sep. 20, 2016 for U.S. Appl. No. 12/964,710 filed Dec. 9, 2010.
Extended European Search Report for Application No. 16154623.9, mailed on Apr. 12, 2016.
Fiehn O., et al., "Mass Spectrometry: Quantitation" In: D Ganten and K Ruckpaul (Editors): "Encyclopedia Reference of Genomics and Proteomics and Molecular Medicine", Springer, 2006, pp. 1030-1034.
Jessome L.L., et al., "Ion Suppression: A Major Concern in Mass Spectromery,", Advanstar Communications Inc., 2006, vol. 24 (5), pp. 498-510.
Non-Final Office Action mailed May 3, 2016 for U.S. Appl. No. 14/639,834 filed Mar. 5, 2015.
Non-Final Office Action mailed Jan. 12, 2016 for U.S. Appl. No. 14/715,153 filed May 18, 2015.
Non-Final Office Action mailed Sep. 19, 2016 for U.S. Appl. No. 14/267,014 filed May 2014.
Non-Fonal Office Action mailed Mar. 24, 2016 for U.S. Appl. No. 15/005,801, filed Jan. 25, 2016.
Adachi T., et al., "Determination of Vitamin D3 nad D2 in the Multi-Vitamin Tablets by High Performance Liquid Chromatography/Atmospheric Pressure Chemical Ionization Mass Spectrometry,"Analytical Science, 1994, vol. 10, pp. 457-460.
Final Office Action mailed Oct. 2, 2013 for U.S. Appl. No. 13/751,915 filed Jan. 28, 2013.
Final Office Action mailed May 4, 2015 for U.S. Appl. No. 12/964,710 filed Dec. 9, 2010.
Final Office Action mailed Apr. 9, 2015 for U.S. Appl. No. 14/180,722 filed Feb. 14, 2014.
Final Office Action mailed Dec. 13, 2013 for U.S. Appl. No. 13/514,892 filed Jun. 8, 2012.
LC-MS: Why use it, and what is it?, Metabolite Services at JIC [online], [retrieved on Sep. 6, 2014]. Retried from the Internet.
Non-Final Office Action mailed Sep. 10, 2014 for U.S. Appl. No. 12/964,710, filed Dec. 9, 2010.
Non-Final Office Action mailed Dec. 11, 2013 for U.S. Appl. No. 14/063,956 filed Oct. 25, 2013.
Non-Final Office Action mailed Sep. 11, 2013 for U.S. Appl. No. 13/871,457 filed Apr. 26, 2013.
Non-Final Office Action mailed Dec. 12, 2014 for U.S. Appl. No. 14/063,956 filed Oct. 25, 2013.
Non-Final Office Action mailed Sep. 19, 2014 for U.S. Appl. No. 14/180,722 filed Feb. 14, 2014.

(56) References Cited

OTHER PUBLICATIONS

Non-Final Office Action mailed Aug. 22, 2014 for U.S. Appl. No. 13/5141,892 filed Jun. 8, 2012.
Non-Final Office Action mailed Jun. 25, 2015 for U.S. Appl. No. 14/639,834 filed Mar. 5, 2015.
Supplementary European Search Report for Application No. EP06749272, mailed on Feb. 2, 2009, 7 pages.
Supplementary European Search Report for Application for EP10836711, mailed on Oct. 28, 2013, 11 pages.
Supplementary European Search Report for Application No. EP11184151, mailed on Dec. 1, 2011, 7 pages.
Written Opinion for Application No. PCT/US08/84709, mailed on Feb. 24, 2009, 9 Pages.
Written Opinion for Application No. PCT/US10/59771, mailed on Feb. 11, 2011, 4 Pages.
Examiner's Answer in U.S. Appl. No. 12/964,717 dtd Jan. 9, 2014.
Aberhart, D.J. et al., Journal of Organic Chemistry 1976, 41, 2098-2102.
Mitamura, K. et al., Yakugaku Zasshi 1996, 118, 206-215.
Boyer, F.O. et al. Analyst 1999, 124, 401-406.
Magalhaes, P.J. et al., Journal of Agricultural and Food Chemistry 2007, 55, 7995-8002.
Extended European Search Report in EP Application No. 10836711.1 dtd Nov. 14, 2013 (12 pages).
Extended European Search Report in EP Appn. No. 10836702.0 dtd Oct. 2, 2013 (12 pages).
Heudi et al., "Simultaneous quantification of Vitamins A, D3 and E in fortified infant formulae by liquid chromatography-mass spectrometry," J. Chroma., 1022:115-123 (2004).
Notice of Allowance in U.S. Appl. No. 13/751,915 dtd Dec. 3, 2013 (7 pages).
Notice of Allowance in U.S. Appl. No. 13/871,457 dtd Nov. 6, 2013 (8 pages).
Office Action in U.S. Appl. No. 13/327,650 dtd Sep. 12, 2012 (7 pages).

\* cited by examiner

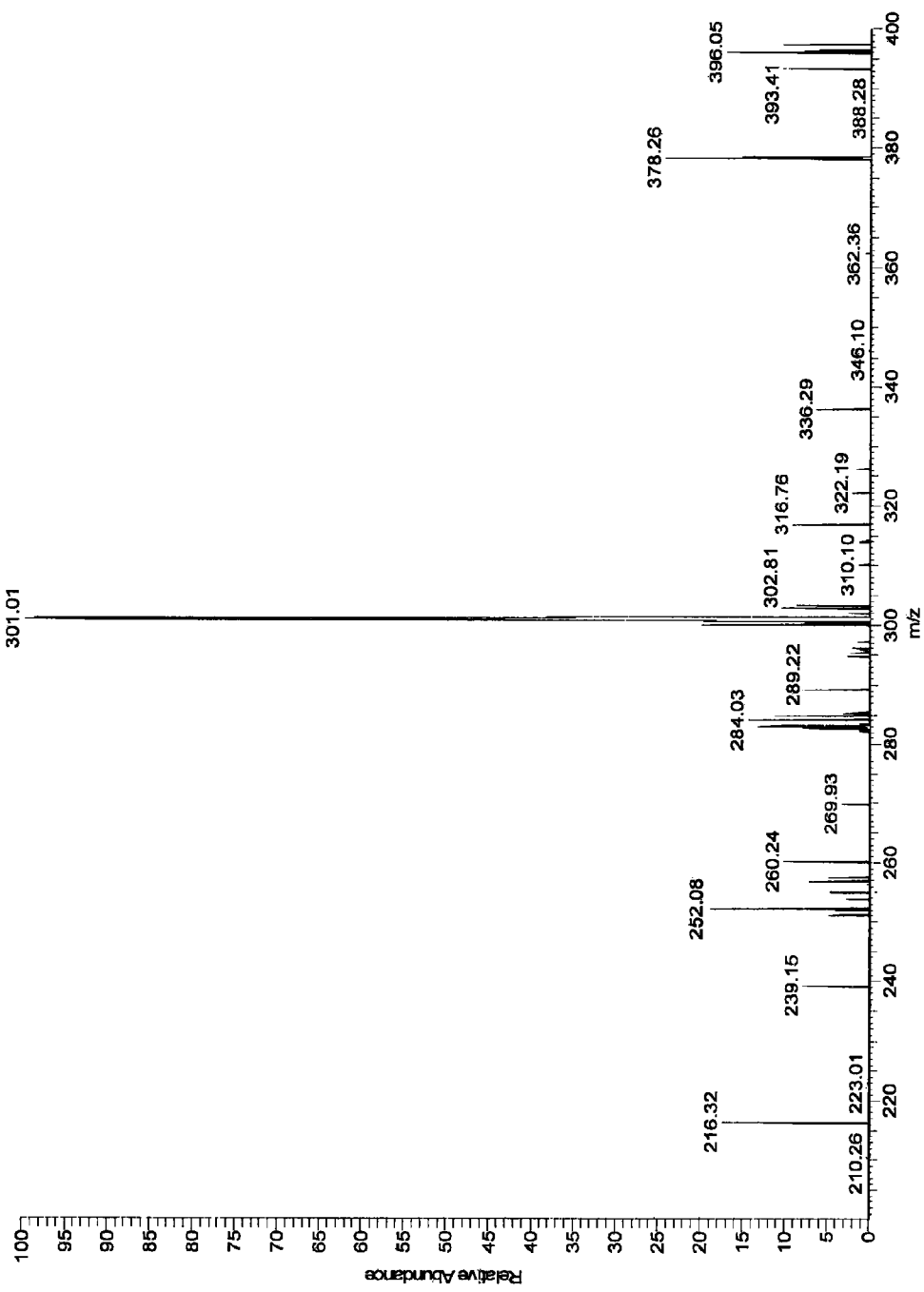

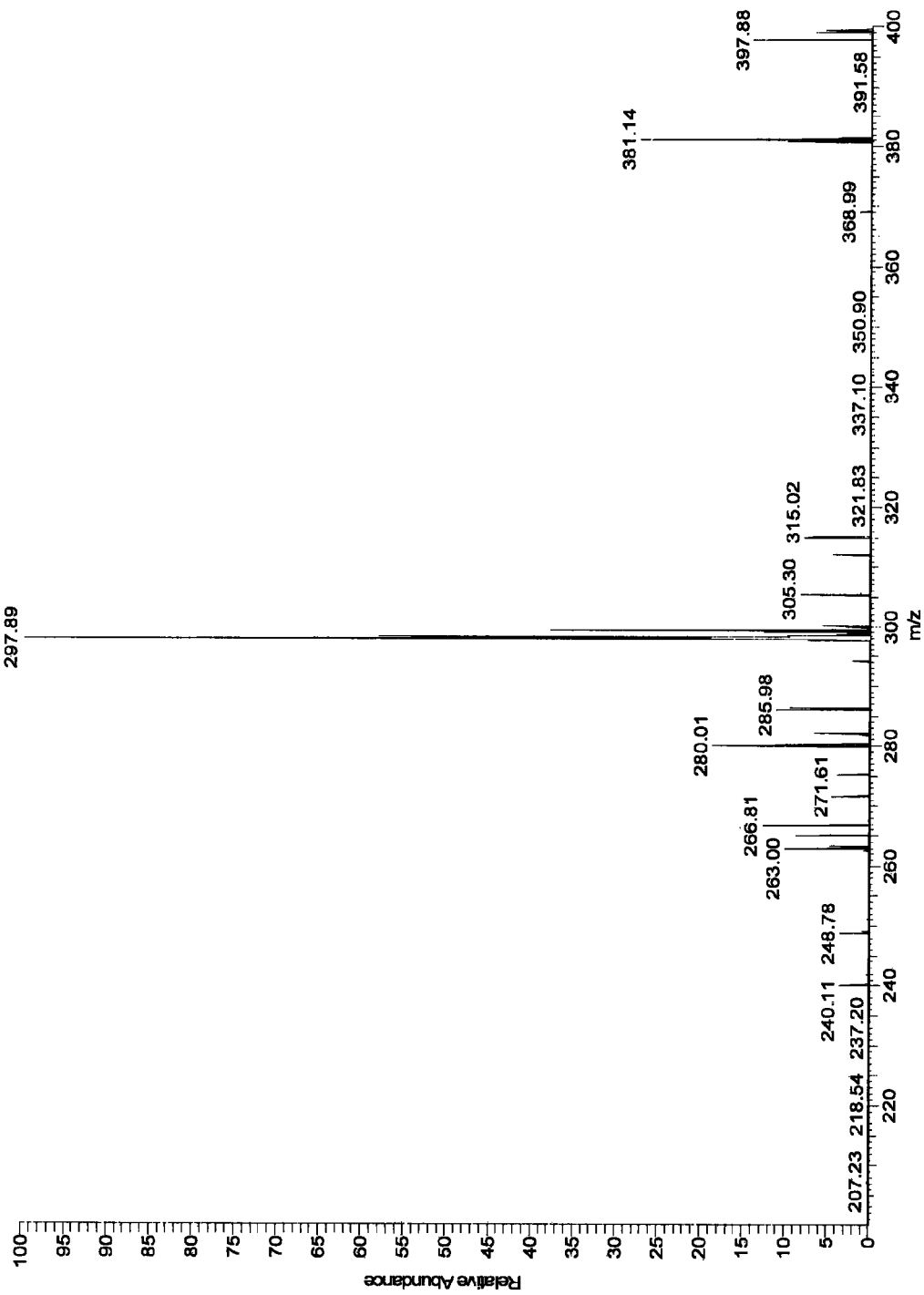

VITAMIN D METABOLITE DETERMINATION UTILIZING MASS SPECTROMETRY FOLLOWING DERIVATIZATION

CROSS-REFERENCE TO RELATED PATENT APPLICATION

This application is a continuation of U.S. application Ser. No. 13/115,935, filed May 25, 2011, which is a continuation of U.S. application Ser. No. 12/630,790 filed Dec. 3, 2009 (now U.S. Pat. No. 7,977,117), each of which is incorporated herein by reference in its entirety.

FIELD OF THE INVENTION

The invention relates to the quantitative measurement of vitamin D metabolites. In a particular aspect, the invention relates to methods for quantitative measurement of vitamin D metabolites by HPLC-tandem mass spectrometry.

BACKGROUND OF THE INVENTION

Vitamin D is an essential nutrient with important physiological roles in the positive regulation of calcium ($Ca^{2+}$) homeostasis. Vitamin D can be made de novo in the skin by exposure to sunlight or it can be absorbed from the diet. There are two forms of vitamin D; vitamin $D_2$ (ergocalciferol) and vitamin $D_3$ (cholecalciferol). Vitamin $D_3$ is the form synthesized de novo by animals. It is also a common supplement added to milk products and certain food products produced in the United States. Both dietary and intrinsically synthesized vitamin $D_3$ must undergo metabolic activation to generate the bioactive metabolites. In humans, the initial step of vitamin $D_3$ activation occurs primarily in the liver and involves hydroxylation to form the intermediate metabolite 25-hydroxycholecalciferol (calcifediol; $25OHD_3$). Calcifediol is the major form of Vitamin $D_3$ in circulation. Circulating $25OHD_3$ is then converted by the kidney to form 1α,25-dihydroxyvitamin $D_3$ (calcitriol; $1α,25(OH)_2D_3$), which is generally believed to be the metabolite of Vitamin $D_3$ with the highest biological activity.

Vitamin $D_2$ is derived from fungal and plant sources. Many over-the-counter dietary supplements contain ergocalciferol (vitamin $D_2$) rather than cholecalciferol (vitamin $D_3$). Drisdol, the only high-potency prescription form of vitamin D available in the United States, is formulated with ergocalciferol. Vitamin $D_2$ undergoes a similar pathway of metabolic activation in humans as Vitamin $D_3$, forming the metabolites $25OHD_2$ and $1α,25(OH)_2D_2$. Vitamin $D_2$ and vitamin $D_3$ have long been assumed to be biologically equivalent in humans, however recent reports suggest that there may be differences in the bioactivity and bioavailability of these two forms of vitamin D (Armas et. al., (2004) J. Clin. Endocrinol. Metab. 89:5387-5391).

Measurement of vitamin D, the inactive vitamin D precursor, is rare in clinical settings. Rather, serum levels of 25-hydroxyvitamin $D_3$, 25-hydroxyvitamin $D_2$, and total 25-hydroxyvitamin D ("25OHD") are useful indices of vitamin D nutritional status and the efficacy of certain vitamin D analogs. The measurement of 25OHD is commonly used in the diagnosis and management of disorders of calcium metabolism. In this respect, low levels of 25OHD are indicative of vitamin D deficiency associated with diseases such as hypocalcemia, hypophosphatemia, secondary hyperparathyroidism, elevated alkaline phosphatase, osteomalacia in adults and rickets in children. In patients suspected of vitamin D intoxication, elevated levels of 25OHD distinguishes this disorder from other disorders that cause hypercalcemia.

Measurement of $1α,25(OH)_2D$ is also used in clinical settings. Certain disease states can be reflected by circulating levels of $1α,25(OH)_2D$, for example kidney disease and kidney failure often result in low levels of $1α,25(OH)_2D$. Elevated levels of $1,25(OH)_2D$ may be indicative of excess parathyroid hormone or can be indicative of certain diseases such as sarcoidosis or certain types of lymphomas.

Detection of vitamin D metabolites has been accomplished by radioimmunoassay with antibodies co-specific for $25OHD_2$ and $25OHD_3$. Because the current immunologically-based assays do not separately resolve $25OHD_2$ and $25OHD_3$, the source of any nutritional deficiency of vitamin D cannot be determined without resorting to other tests. Reports have been published that disclose methods for detecting specific vitamin D metabolites using mass spectrometry. In some of the reports, the vitamin D metabolites are derivatized prior to mass spectrometry, but in others, they are not. For example Holmquist, et al., U.S. patent application Ser. No. 11/946,765, filed Dec. 28, 2007; Yeung B, et al., J Chromatogr. 1993, 645(1):115-23; Higashi T, et al., Steroids. 2000, 65(5):281-94; Higashi T, et al., Biol Pharm Bull. 2001, 24(7):738-43; Higashi T, et al., J Pharm Biomed Anal. 2002, 29(5):947-55; Higashi T, et al., Anal. Biochanal Chem, 2008, 391:229-38; and Aronov, et al., Anal Bioanal Chem, 2008, 391:1917-30 disclose methods for detecting various vitamin D metabolites by derivatizing the metabolites prior to mass spectrometry. Methods to detect underivatized vitamin D metabolites are reported in Clarke, et al., in U.S. patent application Ser. Nos. 11/101,166, filed Apr. 6, 2005, and 11/386,215, filed Mar. 21, 2006, and Singh, et al., in U.S. patent application Ser. No. 10/977,121, filed Oct. 24, 2004.

SUMMARY OF THE INVENTION

The present invention provides methods for detecting the amount of one or more vitamin D metabolites in a sample by mass spectrometry, including tandem mass spectrometry. The methods include derivatizing vitamin D metabolites in the sample prior to analysis.

In one aspect, the invention provides methods for determining the amount of one or more vitamin D metabolites in a sample by mass spectrometry. In some embodiments, the methods include the steps of: (i) subjecting one or more 4-phenyl-1,2,4-triazoline-3,5-dione (PTAD)-derivatized vitamin D metabolites in the sample to an extraction column and an analytical column; (ii) subjecting one or more PTAD-derivatized vitamin D metabolites in the sample to an ionization source to generate one or more ions detectable by mass spectrometry; (iii) determining the amount of one or more of the PTAD-derivatized vitamin D metabolite ions by mass spectrometry; and (iv) relating the amount of PTAD-derivatized vitamin D metabolite ions determined in step (iii) to the amount of a vitamin D metabolite in the sample. In these methods, the sample is subjected to 4-phenyl-1,2,4-triazoline-3,5-dione (PTAD) under conditions sufficient to generate one or more PTAD-derivatized vitamin D metabolites prior to step (i). In some embodiments, the sample is subject to turbulent flow liquid chromatography (TFLC) as the extraction column, and no analytical column is used. In other embodiments, no chromatography, including extraction chromatography, is used. In these methods, the derivatized vitamin D metabolites may be ionized with laser diode thermal desorption (LDTD).

In some embodiments, the extraction column of step (i) is a solid-phase extraction (SPE) column; preferably, the extraction column of step (i) is a turbulent flow liquid chromatography (TFLC) column. In some embodiments, the analytical column of step (i) is a high performance liquid chromatography (HPLC) column.

In some embodiments, the methods include the steps of: (i) subjecting the sample to turbulent flow liquid chromatography (TFLC); (ii) ionizing one or more Cookson-type vitamin D metabolite derivatives in the sample to generate one or more ions detectable by mass spectrometry; (iii) determining the amount of one or more of the Cookson-type vitamin D metabolite derivative ions by mass spectrometry; and (iv) relating the amount of Cookson-type vitamin D metabolite derivative ions determined in step (iv) to the amount of a vitamin D metabolite in the sample. In these embodiments, the sample is subjected to a Cookson-type derivatizing reagent under conditions sufficient to generate one or more Cookson-type vitamin D metabolite derivatives prior to step (i). In some embodiments, the sample is subjected to high performance liquid chromatography (HPLC) after step (i) but prior to step (ii). In some related embodiments, the TFLC of step (i), the HPLC, and the ionization of step (ii) are conducted in an on-line fashion.

Cookson-type derivatizing reagents useful for these methods may be selected from the group consisting of 4-phenyl-1,2,4-triazoline-3,5-dione (PTAD), 4-[2-(6,7-dimethoxy-4-methyl-3-oxo-3,4-dihydroquinoxalyl)ethyl]-1,2,4-triazoline-3,5-dione (DMEQTAD), 4-(4-nitrophenyl)-1,2,4-triazoline-3,5-dione (NPTAD), and 4-ferrocenylmethyl-1,2,4-triazoline-3,5-dione (FMTAD), and isotopically labeled variants thereof. In preferred embodiments, the Cookson-type derivatizing reagent is 4-phenyl-1,2,4-triazoline-3,5-dione (PTAD) or an isotopically labeled variant thereof.

In some embodiments, the methods include the steps of: (i) subjecting the sample to 4-phenyl-1,2,4-triazoline-3,5-dione (PTAD) under conditions sufficient to generate one or more PTAD-vitamin D metabolite derivatives; (ii) ionizing one or more PTAD-vitamin D metabolite derivatives in the sample with laser diode thermal desorption to generate one or more ions detectable by mass spectrometry; (iii) determining the amount of one or more of the PTAD-vitamin D metabolite derivative ions by mass spectrometry; and (v) relating the amount of PTAD-vitamin D metabolite derivative ions determined in step (iv) to the amount of a vitamin D metabolite in the sample; wherein the one or more vitamin D metabolite derivatives are selected from the group consisting of 25-hydroxyvitamin $D_2$ (25OHD$_2$), 25-hydroxyvitamin $D_3$ (25OHD$_3$), 1α,25-dihydroxyvitamin $D_2$ (1α,25(OH)$_2D_2$), and 1α,25-dihydroxyvitamin $D_3$ (1α,25(OH)$_2D_3$). In some embodiments, the one or more vitamin D metabolite derivatives comprise two or more selected from the group consisting of 25-hydroxyvitamin $D_2$ (25OHD$_2$), 25-hydroxyvitamin $D_3$ (25OHD$_3$), 1α,25-dihydroxyvitamin $D_2$ (1α,25(OH)$_2D_2$), and 1α,25-dihydroxyvitamin $D_3$ (1α,25(OH)$_2D_3$). In related embodiments, the two or more vitamin D metabolite derivatives are ionized simultaneously. In some embodiments, the sample is not subjected to chromatography. In some embodiments, the sample is not subjected to liquid chromatography.

In the methods described herein, mass spectrometry may be tandem mass spectrometry. In embodiments utilizing tandem mass spectrometry, tandem mass spectrometry may be conducted by any method known in the art, including for example, multiple reaction monitoring, precursor ion scanning, or product ion scanning.

In the methods described herein, the one or more vitamin D metabolites may comprise one or more vitamin D metabolites selected from the group consisting of 25-hydroxyvitamin $D_2$ (25 OHD$_2$), 25-hydroxyvitamin $D_3$ (25 OHD$_3$), 1α,25-dihydroxyvitamin $D_2$ (1α,25(OH)$_2D_2$), and 1α,25-dihydroxyvitamin $D_3$ (1α,25(OH)$_2D_3$); such as comprising 25-hydroxyvitamin $D_2$ (25OHD$_2$) and 25-hydroxyvitamin $D_3$ (25OHD$_3$), or comprising 1α,25-dihydroxyvitamin $D_2$ (1α,25(OH)$_2D_2$) and 1α,25-dihydroxyvitamin $D_3$ (1α,25(OH)$_2D_3$).

Thus, in some embodiments, the one or more Cookson-type derivatized vitamin D metabolites, or the one or more PTAD-derivatized vitamin D metabolites, comprise one or more of the group consisting of PTAD-derivatized 25-hydroxyvitamin $D_2$ (PTAD-25OHD$_2$), PTAD-derivatized 25-hydroxyvitamin $D_3$ (PTAD-25OHD$_3$), PTAD-derivatized 1α,25-dihydroxyvitamin $D_2$ (PTAD-1α,25(OH)$_2D_2$), and PTAD-derivatized 1α,25-dihydroxyvitamin $D_3$ (PTAD-1α25(OH)$_2D_3$).

In embodiments where the one or more Cookson-type derivatized vitamin D metabolites, or the one or more PTAD-derivatized vitamin D metabolites, comprise PTAD-derivatized 25-hydroxyvitamin $D_2$ (PTAD-25OHD$_2$), the one or more Cookson-type or PTAD-derivatized vitamin D metabolite ions comprise ions selected from the group consisting of ions with a mass/charge ratio (m/z) of 570.3±0.5 and 298.1±0.5. In some embodiments, the one or more Cookson-type or PTAD-derivatized vitamin D metabolite ions comprise a parent ion with a mass/charge ratio (m/z) of 570.3±0.5 and a fragment ion with a mass/charge ratio (m/z) of 298.1±0.5.

In embodiments where the one or more Cookson-type derivatized vitamin D metabolites, or the one or more PTAD-derivatized vitamin D metabolites, comprise PTAD-derivatized 25-hydroxyvitamin $D_3$ (PTAD-25OHD$_3$), the one or more Cookson-type or PTAD-derivatized vitamin D metabolite ions comprise ions selected from the group consisting of ions with a mass/charge ratio (m/z) of 558.3±0.5 and 298.1±0.5. In some embodiments, the one or more Cookson-type or PTAD-derivatized vitamin D metabolite ions comprise a parent ion with a mass/charge ratio (m/z) of 558.3±0.5 and a fragment ion with a mass/charge ratio (m/z) of 298.1±0.5.

In embodiments where the one or more Cookson-type derivatized vitamin D metabolites, or the one or more PTAD-derivatized vitamin D metabolites, comprise PTAD-derivatized 1α,25-dihydroxyvitamin $D_2$ (PTAD-1α,25(OH)$_2$ $D_2$), the one or more Cookson-type or PTAD-derivatized vitamin D metabolite ions comprise ions selected from the group consisting of ions with a mass/charge ratio (m/z) of 550.4±0.5, 568.4±0.5, 277.9±0.5, and 298.0±0.5. In some embodiments, the one or more Cookson-type or PTAD-derivatized vitamin D metabolite ions comprise a parent ion with a mass/charge ratio (m/z) of 550.4±0.5 and a fragment ion with a mass/charge ratio (m/z) of 277.9±0.5. In some embodiments, the one or more Cookson-type or PTAD-derivatized vitamin D metabolite ions comprise a parent ion with a mass/charge ratio (m/z) of 568.4±0.5 and a fragment ion with a mass/charge ratio (m/z) of 298.0±0.5.

In embodiments where the one or more Cookson-type derivatized vitamin D metabolites, or the one or more PTAD-derivatized vitamin D metabolites, comprise PTAD-derivatized 1α,25-dihydroxyvitamin $D_3$ (PTAD-1α,25(OH)$_2$ $D_3$), the one or more Cookson-type or PTAD-derivatized vitamin D metabolite ions comprise ions selected from the group consisting of ions with a mass/charge ratio (m/z) of 538.4±0.5, 556.4±0.5, 278.1±0.5, and 298.0±0.5. In some embodiments, the one or more Cookson-type or PTAD-derivatized, vitamin D metabolite ions comprise a parent ion with a mass/charge ratio (m/z) of 538.4±0.5 and a fragment ion with a mass/charge ratio (m/z) of 278.1±0.5. In some embodiments, the one or more Cookson-type or PTAD-derivatized vitamin D metabolite ions comprise a parent ion with a mass/charge ratio (m/z) of 556.4±0.5 and a fragment ion with a mass/charge ratio (m/z) of 298.0±0.5.

In embodiments which utilize two or more of an extraction column, an analytical column, and an ionization source, two or more of these components may be connected in an on-line fashion to allow for automated sample processing and analysis.

As used herein, the term "vitamin D metabolite" refers to any vitamin D analog or any chemical species related to vitamin D generated by a biotransformation of vitamin D, such as intermediates and products of vitamin D metabolism. Vitamin D metabolites may include chemical species generated by biotransformation of analogs of, or a chemical species related to, vitamin $D_2$ or vitamin $D_3$. Vitamin D metabolites may be found in the circulation of an animal and/or may be generated by a biological organism, such as an animal. Vitamin D metabolites may be metabolites of naturally occurring forms of vitamin D or may be metabolites of synthetic vitamin D analogs. In certain embodiments a vitamin D metabolite is one or more compounds selected from the group consisting of 25-hydroxyvitamin $D_3$, 25-hydroxyvitamin $D_2$, $1\alpha,25$-dihydroxyvitamin $D_3$ and $1\alpha,25$-dihydroxyvitamin $D_2$.

As used herein, "derivatizing" means reacting two molecules to form a new molecule. Thus, a derivatizing agent is an agent that may be reacted with another substance to derivatize the substance. For example, 4-phenyl-1,2,4-triazoline-3,5-dione (PTAD) is a derivatizing reagent that may be reacted with a vitamin D metabolite to form a PTAD-derivatized vitamin D metabolite.

As used here, the names of derivatized forms vitamin D metabolites include an indication as to the nature of derivatization. For example, the PTAD derivative of 25-hydroxyvitamin $D_2$ is indicated as PTAD-25-hydroxyvitamin $D_2$ (or PTAD-25OHD$_2$).

As used herein, a "Cookson-type derivatizing agent" is a 4-substituted 1,2,4-triazoline-3,5-dione compound. Exemplary Cookson-type derivatizing agents include 4-phenyl-1,2,4-triazoline-3,5-dione (PTAD), 4-[2-(6,7-dimethoxy-4-methyl-3-oxo-3,4-dihydroquinoxalyl)ethyl]-1,2,4-triazoline-3,5-dione (DMEQTAD), 4-(4-nitrophenyl)-1,2,4-triazoline-3,5-dione (NPTAD), and 4-ferrocenylmethyl-1,2,4-triazoline-3,5-dione (FMTAD). Additionally, isotopically labeled variants of Cookson-type derivatizing agents may be used in some embodiments. For example, the $^{13}C_6$-PTAD isotopic variant is 6 mass units heavier than normal PTAD and may be used in some embodiments. Derivatization of vitamin D metabolites by Cookson-type reagents can be conducted by any appropriate method. See, e.g., Holmquist, et al., U.S. patent application Ser. No. 11/946,765, filed Dec. 28, 2007; Yeung B, et al., J Chromatogr. 1993, 645(1):115-23; Higashi T, et al., Steroids. 2000, 65(5):281-94; Higashi T, et al., Biol Pharm Bull. 2001, 24(7):738-43; Higashi T, et al., J Pharm Biomed Anal. 2002, 29(5):947-55; Higashi T, et al., Anal. Biochanal Chem, 2008, 391:229-38; and Aronov, et al., Anal Bioanal Chem, 2008, 391:1917-30.

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI), laser diode thermal desorption (LDTD), or electrospray ionization (ESI), may be used in embodiments of the present invention. In certain preferred embodiments, vitamin D metabolites are measured using APCI or LDTD in positive ion mode.

In preferred embodiments, one or more separately detectable internal standards are provided in the sample, the amount of which are also determined in the sample. In these embodiments, all or a portion of both the analyte(s) of interest and the internal standard(s) present in the sample are ionized to produce a plurality of ions detectable in a mass spectrometer, and one or more ions produced from each are detected by mass spectrometry. Preferably, the internal standard(s) are one or more of 25OHD$_2$-[6, 19, 19]-$^2H_3$, 25OHD$_2$-[26, 26, 26, 27, 27, 27]-$^2H_6$, 25OHD$_3$-[6, 19, 19]-$^2H_3$, 25OHD$_3$-[26, 26, 26, 27, 27, 27]-$^2H_6$, $1\alpha,25$(OH)$_2$D$_2$-[6, 19, 19]-$^2H_3$, $1\alpha,25$(OH)$_2$D$_2$-[26, 26, 26, 27, 27, 27]-$^2H_6$, $1\alpha,25$(OH)$_2$D$_3$-[6, 19, 19]-$^2H_3$, and $1\alpha,25$(OH)$_2$D$_3$-[26, 26, 26, 27, 27, 27]-$^2H_6$.

One or more separately detectable internal standards may be provided in the sample prior to treatment of the sample with a Cookson-type derivatizing reagent. In these embodiments, the one or more internal standards may undergo derivatization along with the endogenous vitamin D metabolites, in which case ions of the derivatized internal standards are detected by mass spectrometry. In these embodiments, the presence or amount of ions generated from the analyte of interest may be related to the presence or amount of analyte of interest in the sample. In some embodiments, the internal standards may be isotopically labeled versions of vitamin D metabolites, such as 25OHD$_2$-[6, 19, 19]-$^2H_3$, 25OHD$_2$-[26, 26, 26, 27, 27, 27]-$^2H_6$, 25OHD$_3$-[6, 19, 19]-$^2H_3$, 25OHD$_3$-[26, 26, 26, 27, 27, 27]-$^2H_6$, $1\alpha,25$(OH)$_2$D$_2$-[6, 19, 19]-$^2H_3$, $1\alpha,25$(OH)$_2$D$_2$-[26, 26, 26, 27, 27, 27]-$^2H_6$, $1\alpha,25$(OH)$_2$D$_3$-[6, 19, 19]-$^2H_3$, and $1\alpha,25$(OH)$_2$D$_3$-[26, 26, 26, 27, 27, 27]-$^2H_6$.

Ions detectable in a mass spectrometer may be generated for each of the above identified exemplary internal standards, as demonstrated in Examples 14 and 15, and FIGS. 7-8, 10-11, 13, and 15-16.

As used herein, an "isotopic label" produces a mass shift in the labeled molecule relative to the unlabeled molecule when analyzed by mass spectrometric techniques. Examples of suitable labels include deuterium ($^2H$), $^{13}C$, and $^{15}N$. For example, 25OHD$_2$-[6, 19, 19]-$^2H_3$ and 25OHD$_3$-[6, 19, 19]-$^2H_3$ have masses about 3 mass units higher than native 25OHD$_2$ and 25OHD$_3$. The isotopic label can be incorporated at one or more positions in the molecule and one or more kinds of isotopic labels can be used on the same isotopically labeled molecule.

In other embodiments, the amount of the vitamin D metabolite ion or ions may be determined by comparison to one or more external reference standards. Exemplary external reference standards include blank plasma or serum spiked with one or more of 25OHD$_2$-[6, 19, 19]-$^2H_3$, 25OHD$_2$-[26, 26, 26, 27, 27, 27]-$^2H_6$, 25OHD$_3$-[6, 19, 19]-$^2H_3$, 25OHD$_3$-[26, 26, 26, 27, 27, 27]-$^2H_6$, $1\alpha,25$(OH)$_2$D$_2$-[6, 19, 19]-$^2H_3$, $1\alpha,25$(OH)$_2$D$_2$-[26, 26, 26, 27, 27, 27]-$^2H_6$, $1\alpha,25$(OH)$_2$D$_3$-[6, 19, 19]-$^2H_3$, and $1\alpha,25$(OH)$_2$D$_3$-[26, 26, 26, 27, 27, 27]-$^2H_6$. External standards typically will undergo the same treatment and analysis as any other sample to be analyzed, including treatment with one or more Cookson-type reagents prior to mass spectrometry.

In certain preferred embodiments, the limit of quantitation (LOQ) of 25OHD$_2$ is within the range of 1.9 ng/mL to 10 ng/mL, inclusive; preferably within the range of 1.9 ng/mL to 5 ng/mL, inclusive; preferably about 1.9 ng/mL. In certain preferred embodiments, the limit of quantitation (LOQ) of 25OHD$_3$ is within the range of 3.3 ng/mL to 10 ng/mL, inclusive; preferably within the range of 3.3 ng/mL to 5 ng/mL, inclusive; preferably about 3.3 ng/mL.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis. SPE, including TFLC, may operate via a unitary or mixed mode mechanism. Mixed mode mechanisms utilize ion exchange and hydrophobic retention in the same column; for example, the solid phase of a mixed-mode SPE column may exhibit strong anion exchange and hydrophobic retention; or may exhibit column exhibit strong cation exchange and hydrophobic retention.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 µm.

As used herein, the term "analytical column" refers to a chromatography column having sufficient chromatographic plates to effect a separation of materials in a sample that elute from the column sufficient to allow a determination of the presence or amount of an analyte. In a preferred embodiment the analytical column contains particles of about 5 µm in diameter. Such columns are often distinguished from "extraction columns", which have the general purpose of separating or extracting retained material from non-retained materials in order to obtain a purified sample for further analysis.

As used herein, the terms "on-line" and "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z"). See, e.g., U.S. Pat. Nos. 6,204,500, entitled "Mass Spectrometry From Surfaces;" 6,107,623, entitled "Methods and Apparatus for Tandem Mass Spectrometry;" 6,268,144, entitled "DNA Diagnostics Based On Mass Spectrometry;" 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser diode thermal desorption (LDTD) is a technique wherein a sample containing the analyte is thermally desorbed into the gas phase by a laser pulse. The laser hits the back of a specially made 96-well plate with a metal base. The laser pulse heats the base and the heat causes the sample to transfer into the gas phase. The gas phase sample may then be drawn into an ionization source, where the gas phase sample is ionized in preparation for analysis in the mass spectrometer. When using LDTD, ionization of the gas phase sample may be accomplished by any suitable technique known in the art, such as by ionization with a corona discharge (for example by APCI).

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "lower limit of quantification", "lower limit of quantitation" or "LLOQ" refers to the point where measurements become quantitatively meaningful. The analyte response at this LOQ is identifiable, discrete and reproducible with a relative standard deviation (RSD %) of less than 20% and an accuracy of 80% to 120%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

BRIEF DESCRIPTION OF THE DRAWINGS

FIG. 7B shows an exemplary product ion spectra (covering the m/z range of about 200 to 400) for fragmentation of the PTAD-25-hydroxyvitamin D$_2$-[6, 19, 19]-$^2H_3$ precursor ion with m/z of about 573.3. Details are described in Example 14.

FIG. 8B shows an exemplary product ion spectra (covering the m/z range of about 200 to 400) for fragmentation of the PTAD-25-hydroxyvitamin D$_2$-[26, 26, 26, 27, 27, 27]-$^2H_6$ precursor ion with m/z of about 576.3. Details are described in Example 14.

Figure 14A:
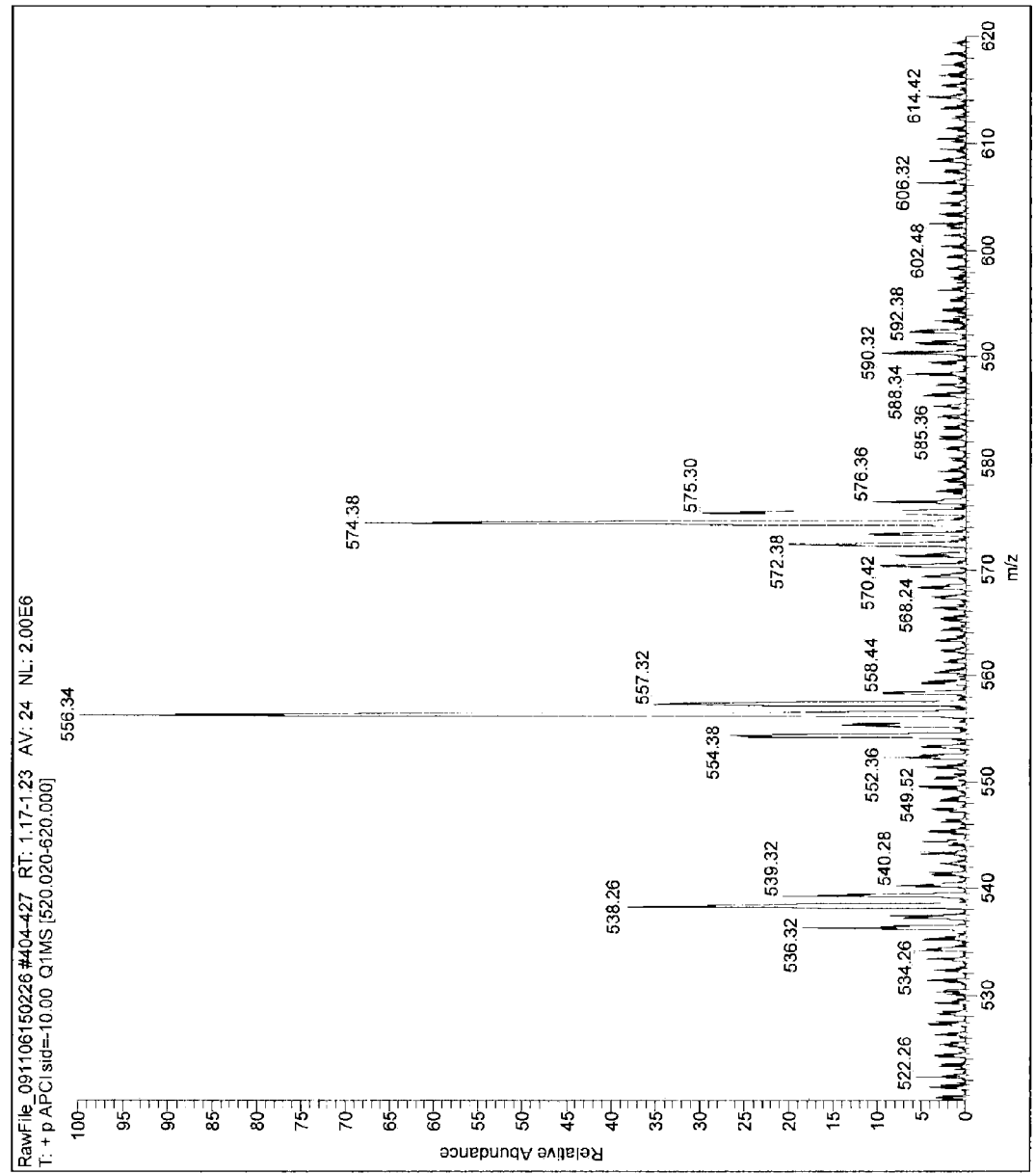
Figure 14B:
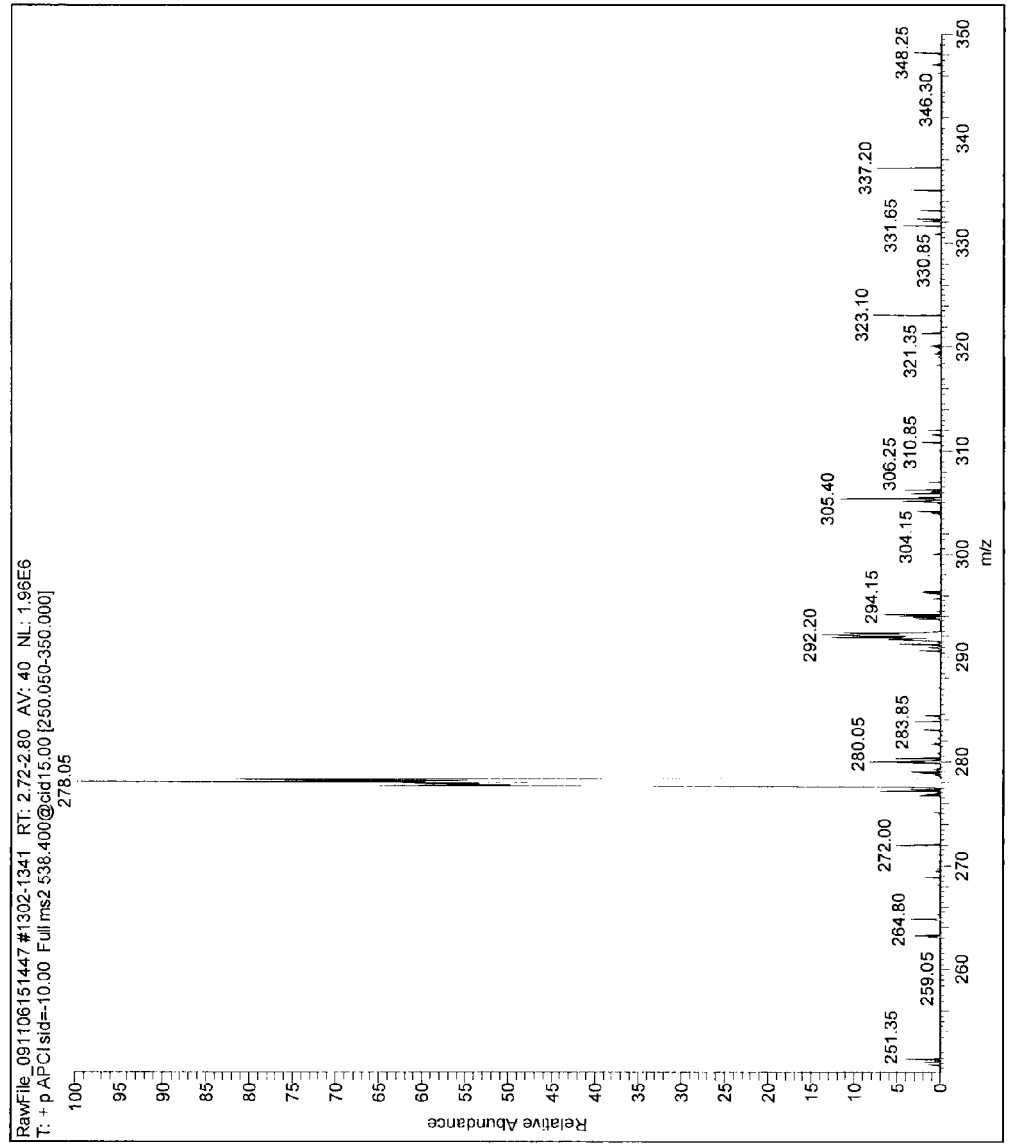
Figure 14C:
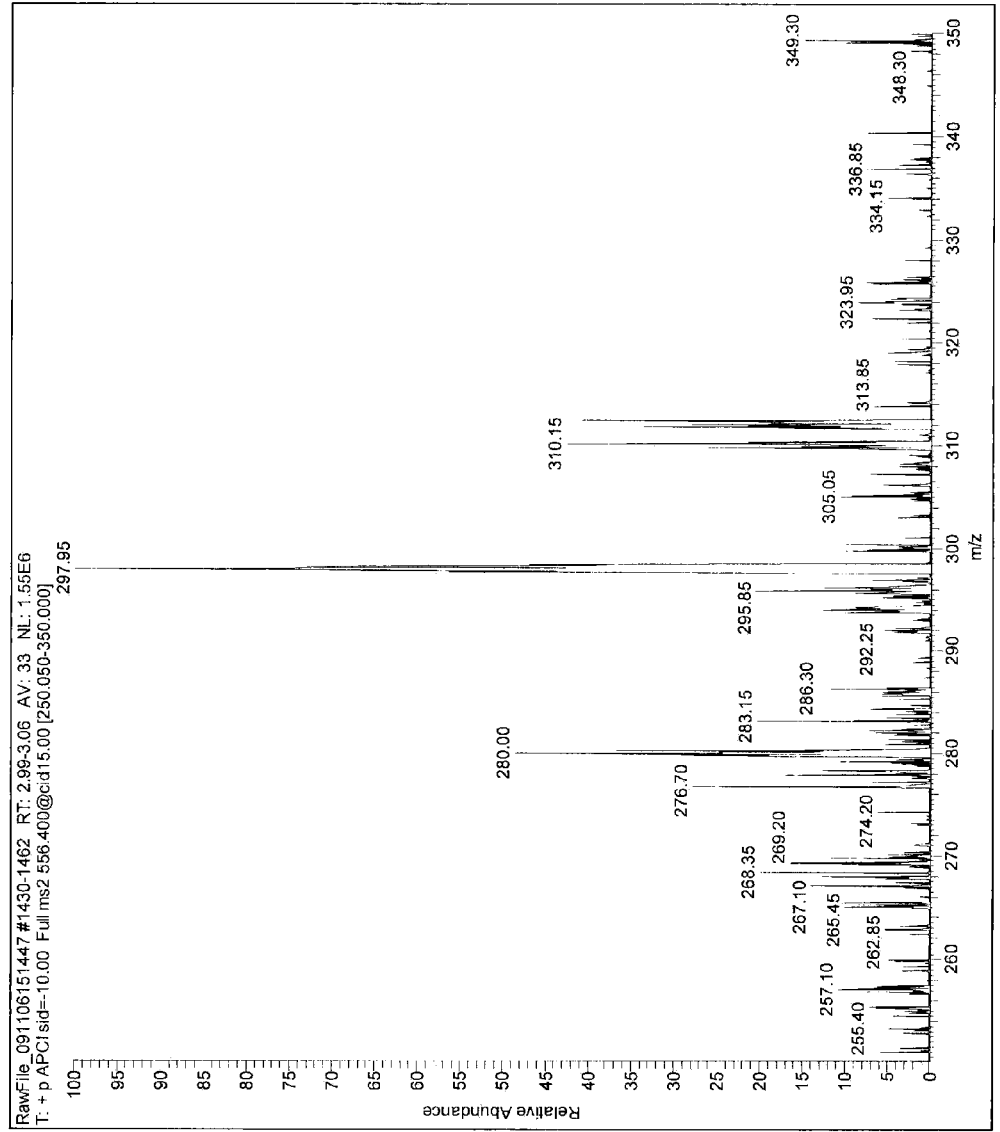
Figure 14D:
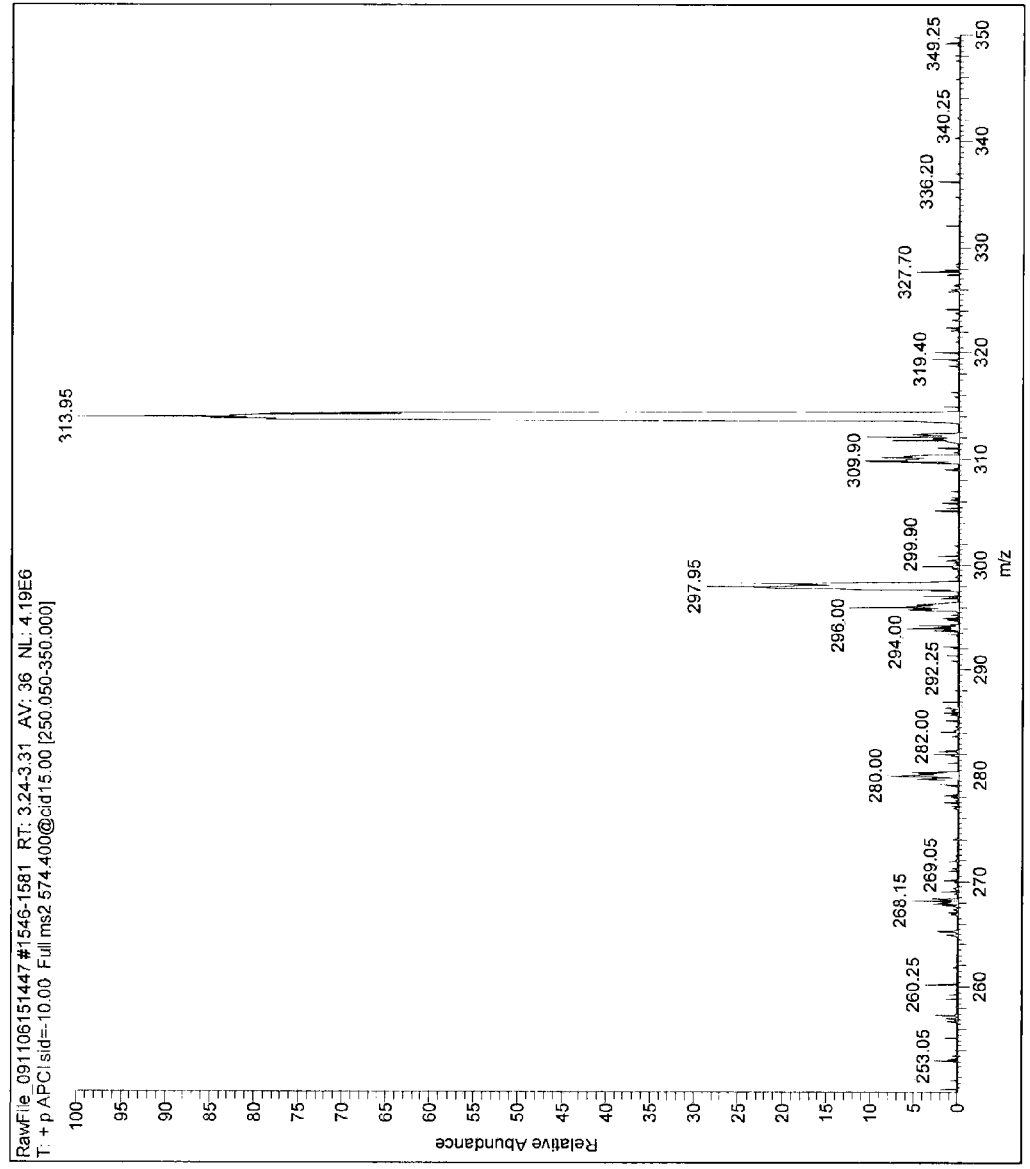

FIG. 14A shows an exemplary Q1 scan spectrum (covering the m/z range of about 520 to 620) for PTAD-1α,25-hydroxyvitamin D$_3$ ions. FIG. 14B shows an exemplary product ion spectra (covering the m/z range of about 250 to 350) for fragmentation of the PTAD-1α,25-dihydroxyvitamin D$_3$ precursor ion with m/z of about 538.4. FIG. 14C shows an exemplary product ion spectra (covering the m/z range of about 250 to 350) for fragmentation of the PTAD-1α,25-dihydroxyvitamin D$_3$ precursor ion with m/z of about 556.4. FIG. 14D shows an exemplary product ion spectra (covering the m/z range of about 250 to 350) for fragmentation of the PTAD-1α,25-dihydroxyvitamin D$_3$ precursor ion with m/z of about 574.4. Details are described in Example 15.

Figure 15A:
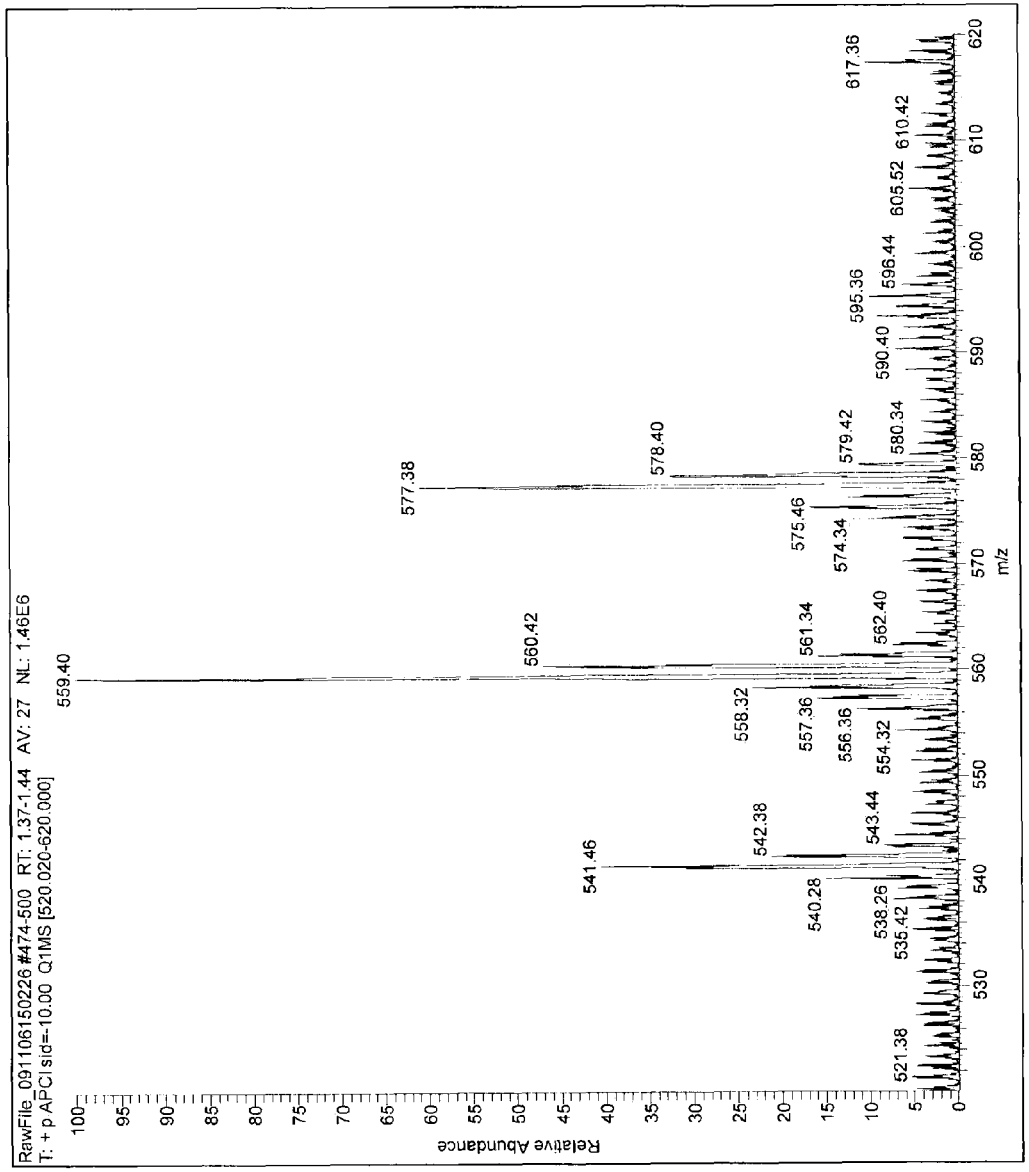
Figure 15B:
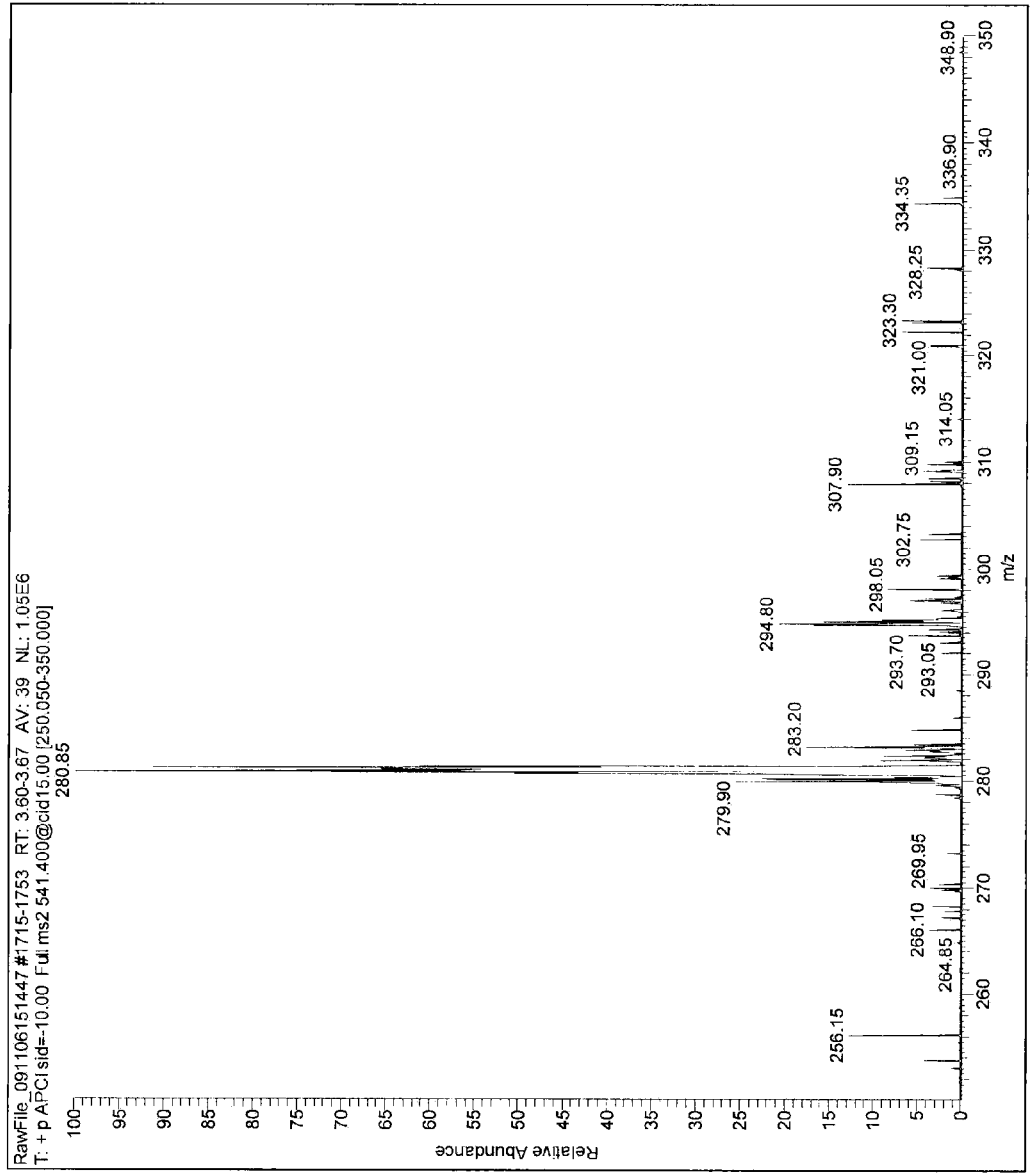
Figure 15C:
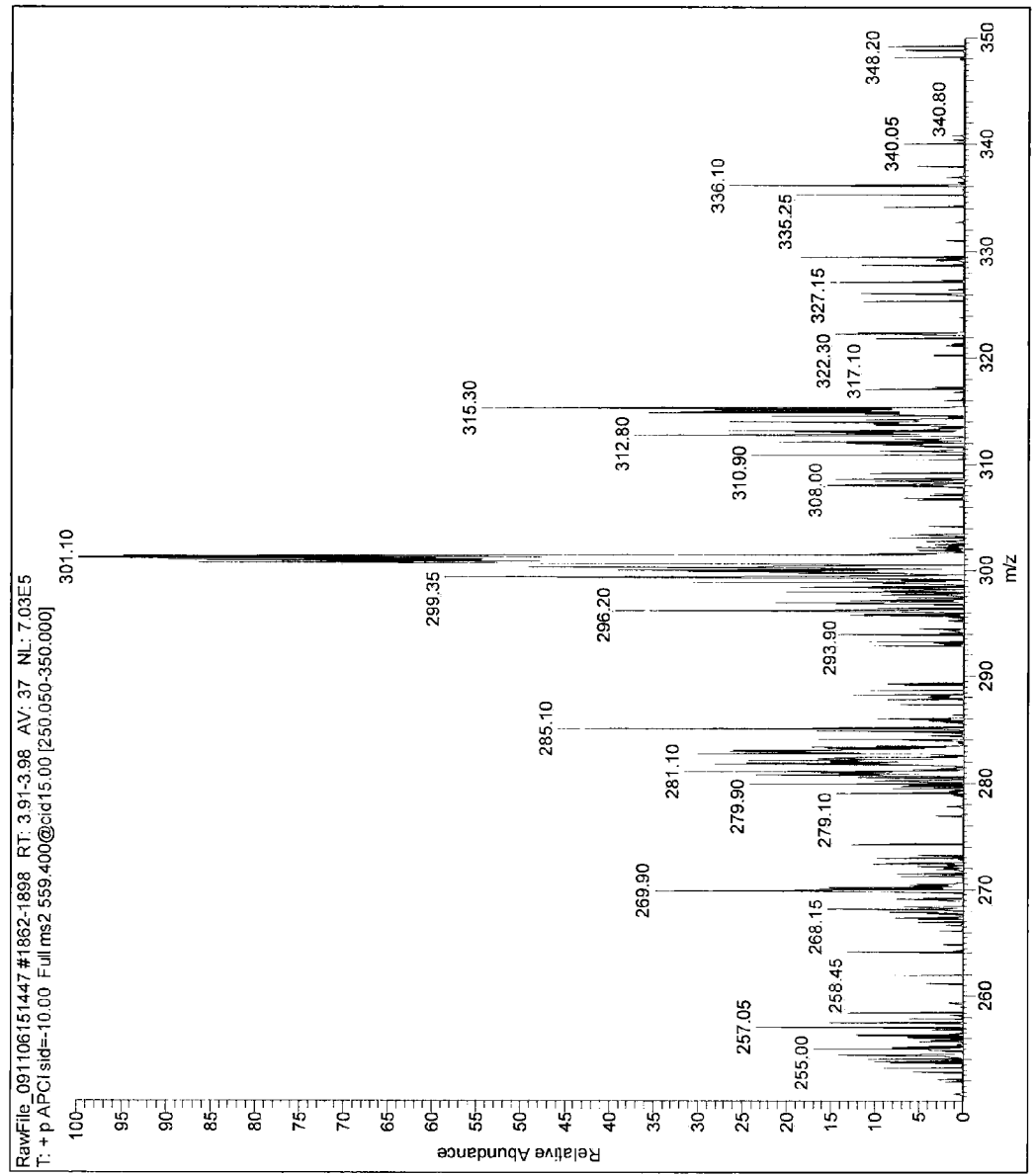
Figure 15D:
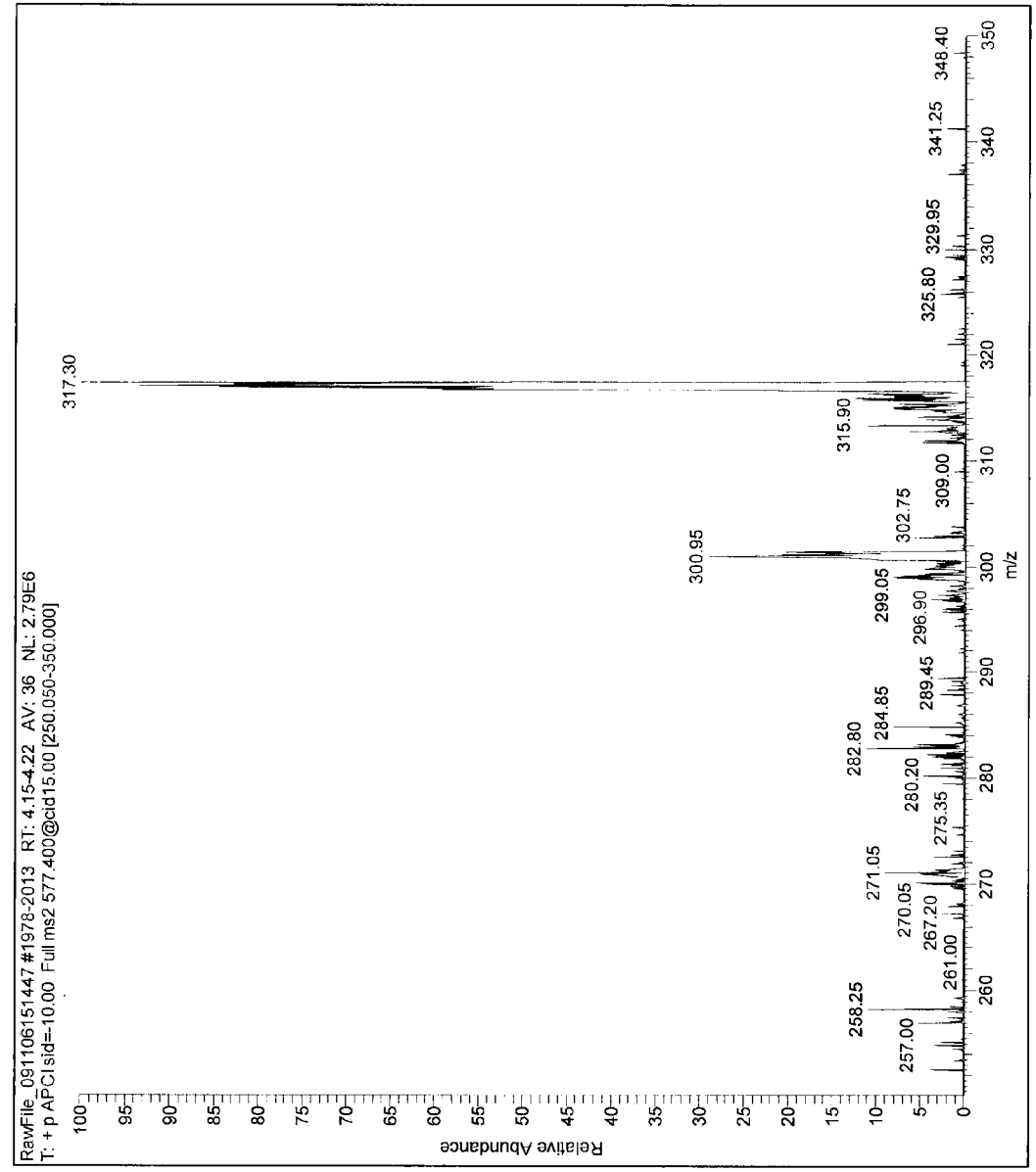

FIG. 15A shows an exemplary Q1 scan spectrum (covering the m/z range of about 520 to 620) for PTAD-1α,25-dihydroxyvitamin D$_3$-[6, 19, 19]-$^2$H$_3$ ions. FIG. 15B shows an exemplary product ion spectra (covering the m/z range of about 250 to 350) for fragmentation of the PTAD-1α,25-dihydroxyvitamin D$_3$-[6, 19, 19]-$^2$H$_3$ precursor ion with m/z of about 541.4. FIG. 15C shows an exemplary product ion spectra (covering the m/z range of about 250 to 350) for fragmentation of the PTAD-1α,25-dihydroxyvitamin D$_3$-[6, 19, 19]-$^2$H$_3$ precursor ion with m/z of about 559.4. FIG. 15D shows an exemplary product ion spectra (covering the m/z range of about 250 to 350) for fragmentation of the 1,25-dihydroxyvitamin D$_3$-[6, 19, 19]-$^2$H$_3$—PTAD precursor ion with m/z of about 577.4. Details are described in Example 15.

Figure 16A:
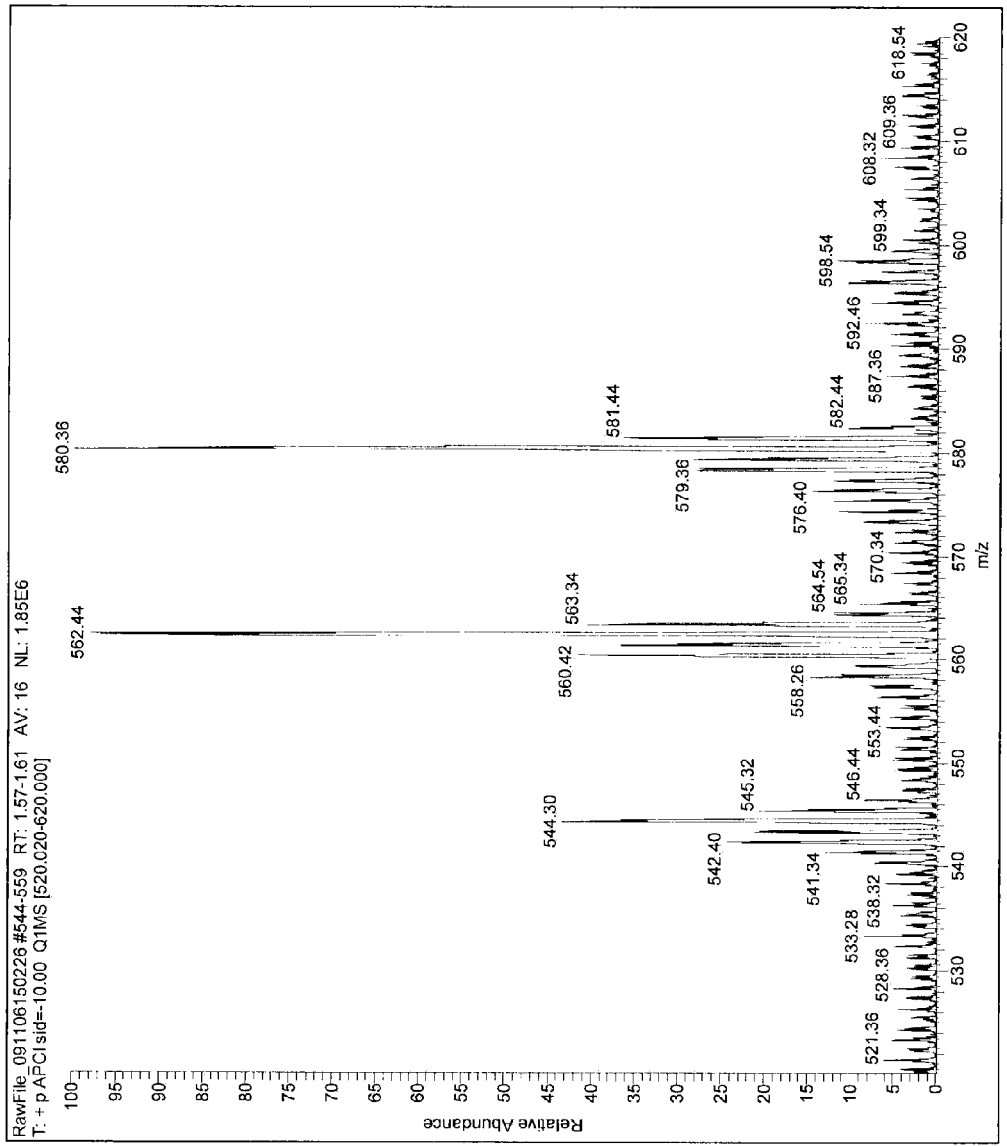
Figure 16B:
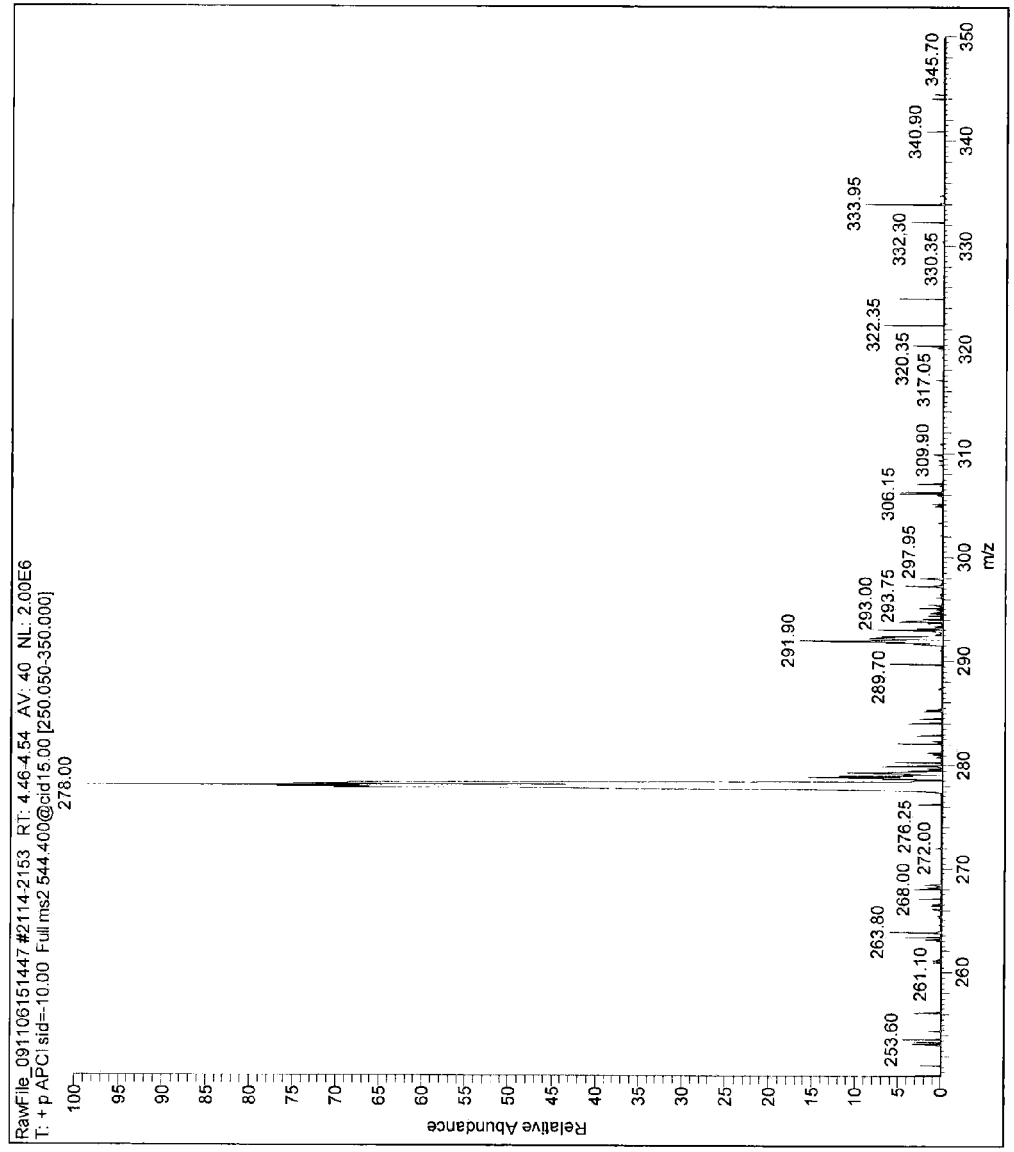
Figure 16C:
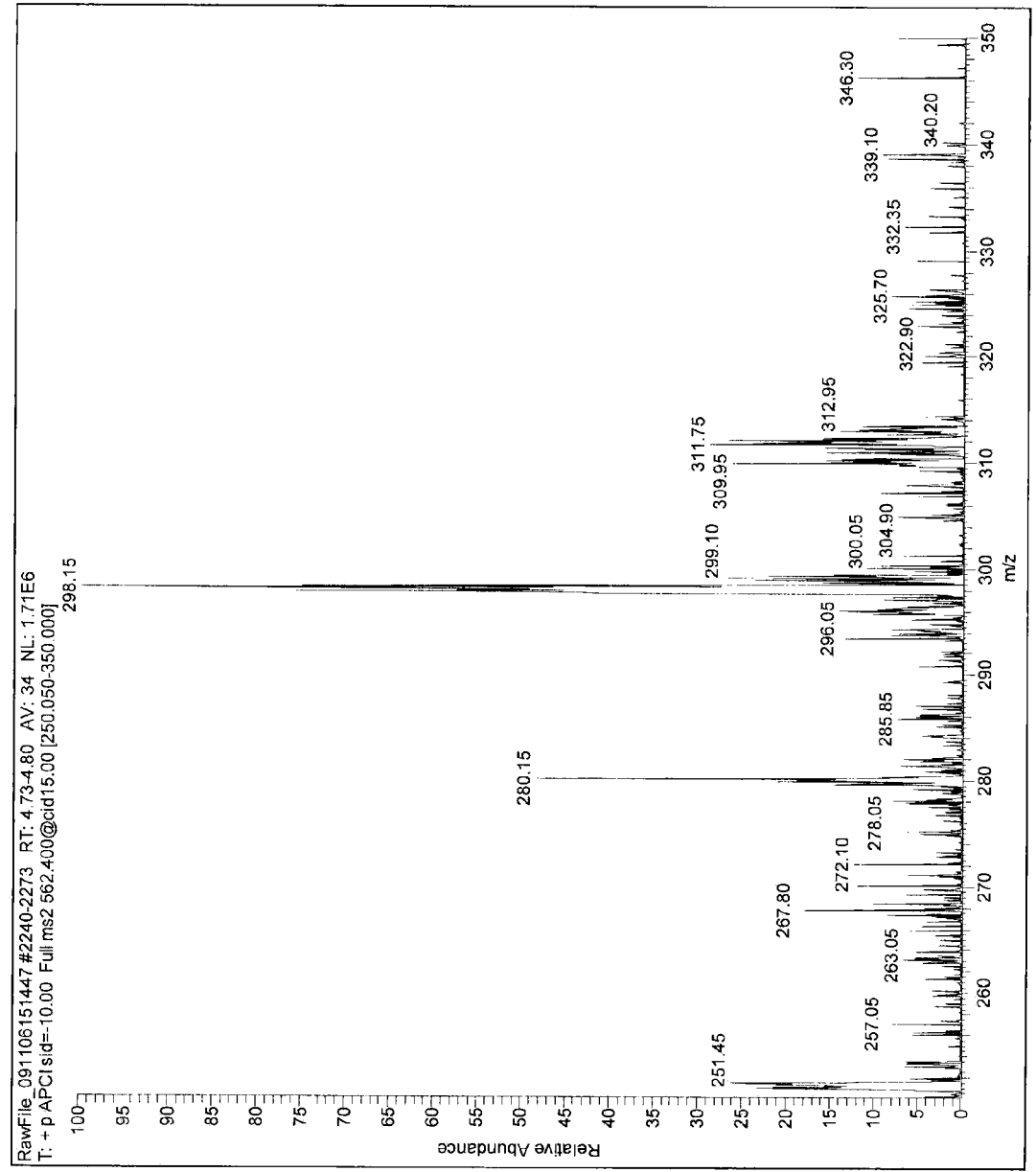
Figure 16D:
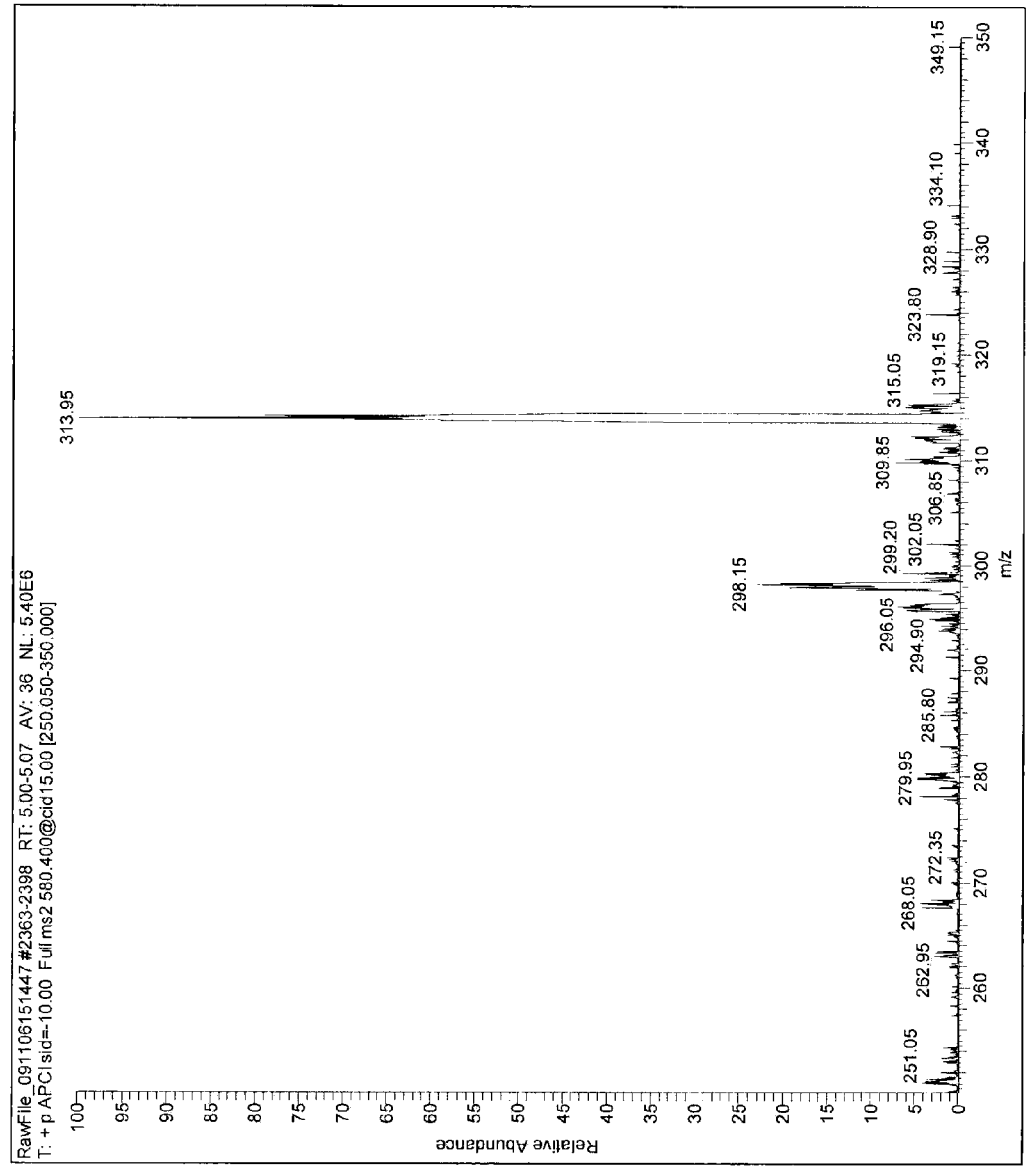

FIG. 16A shows an exemplary Q1 scan spectrum (covering the m/z range of about 520 to 620) for PTAD-1α,25-dihydroxyvitamin D$_3$-[26, 26, 26, 27, 27, 27]-$^2$H$_6$ ions. FIG. 16B shows an exemplary product ion spectra (covering the m/z range of about 250 to 350) for fragmentation of the PTAD-1α,25-dihydroxyvitamin D$_3$-[26, 26, 26, 27, 27, 27]-$^2$H$_6$ precursor ion with m/z of about 544.4. FIG. 16C shows an exemplary product ion spectra (covering the m/z range of about 250 to 350) for fragmentation of the PTAD-1α,25-dihydroxyvitamin D$_3$-[26, 26, 26, 27, 27, 27]-$^2$H$_6$ precursor ion with m/z of about 562.4. FIG. 16D shows an exemplary product ion spectra (covering the m/z range of about 250 to 350) for fragmentation of the PTAD-1α,25-dihydroxyvitamin D$_3$-[26, 26, 26, 27, 27, 27]-$^2$H$_6$ precursor ion with m/z of about 580.4. Details are described in Example 15.

DETAILED DESCRIPTION OF THE INVENTION

Methods are described for measuring vitamin D metabolites in a sample. More specifically, mass spectrometric methods are described for detecting and quantifying vitamin D metabolites in a sample. The methods utilize Cookson-type reagents, such as PTAD, to generate derivatized vitamin D metabolites, and may use an extraction chromatography technique, such as turbulent flow liquid chromatography (TFLC), to perform a purification of the derivatized analytes, combined with methods of mass spectrometry (MS), thereby providing a high-throughput assay system for detecting and quantifying vitamin D metabolites in a sample. In some methods, no chromatography, including extraction chromatography, is necessary for sample analysis. In these methods, the derivatized vitamin D metabolites are ionized with LDTD. Preferred embodiments are particularly well suited for application in large clinical laboratories for automated vitamin D metabolite quantification.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as blood, plasma, serum, saliva, cerebrospinal fluid, or tissue samples; preferably plasma (including EDTA and heparin plasma) and serum; most preferably serum. Such samples may be obtained, for example, from a patient; that is, a living person, male or female, presenting oneself in a clinical setting for diagnosis, prognosis, or treatment of a disease or condition.

The present invention also contemplates kits for a vitamin D metabolite quantitation assay. A kit for a vitamin D metabolite quantitation assay may include a kit comprising the compositions provided herein. For example, a kit may include packaging material and measured amounts of a Cookson-type reagent and an isotopically labeled internal standard, in amounts sufficient for at least one assay. Typically, the kits will also include instructions recorded in a tangible form (e.g., contained on paper or an electronic medium) for using the packaged reagents for use in a vitamin D metabolite quantitation assay.

Calibration and QC pools for use in embodiments of the present invention are preferably prepared using a matrix similar to the intended sample matrix. If no appropriate biological matrix is commercially available with an endogenous concentration of 25OHD$_3$ sufficiently low to act as a blank, a solution of 5% bovine serum albumin in phosphate buffered saline (with an estimated 1.5 ng/mL 25OHD$_3$) may be used for calibration and QC pools.

Sample Preparation for Mass Spectrometric Analysis

In preparation for mass spectrometric analysis, vitamin D metabolites may be enriched relative to one or more other components in the sample (e.g. protein) by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a test sample, especially a biological test sample, such as serum or plasma. Protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving vitamin D metabolites in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to liquid chromatography and subsequent mass spectrometry analysis. In certain embodiments, samples, such as plasma or serum, may be purified by a hybrid protein precipitation/liquid-liquid extraction method. In these embodiments, a sample is mixed with methanol, ethyl acetate, and water, and the resulting mixture is vortexed and centrifuged. The resulting supernatant is removed, dried to completion and reconstituted in acetonitrile. The purified vitamin D metabolites may then be derivatized with any Cookson-type reagent, preferably PTAD or an isotopically labeled variant thereof.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select LC, including HPLC, instruments and columns that are suitable for use with derivatized vitamin D metabolites. The chromatographic column typically includes a medium (i.e., a packing material) to facilitate separation of chemical moieties (i.e., fractionation). The medium may include minute particles, or may include a monolithic material with porous channels. A surface of the medium typically includes a bonded surface that interacts with the various chemical moieties to facilitate separation of the chemical moieties. One suitable bonded surface is a hydrophobic bonded surface such as an alkyl bonded, cyano bonded surface, or highly pure silica surface. Alkyl bonded surfaces may include C-4, C-8, C-12, or C-18 bonded alkyl groups. In preferred embodiments, the column is a highly pure silica column (such as a Thermo Hypersil Gold Aq column). The chromatographic column includes an inlet port for receiving a sample and an outlet port for discharging an effluent that includes the fractionated sample. The sample may be supplied to the inlet port directly, or from an extraction column, such as an on-line SPE cartridge or a TFLC extraction column.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with an alkyl bonded analytical column chromatographic system. In certain preferred embodiments, a highly pure silica column (such as a Thermo Hypersil Gold Aq column) is used. In certain preferred embodiments. HPLC and/or TFLC are performed using HPLC Grade water as mobile phase A and HPLC Grade ethanol as mobile phase B.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, an extraction column may be used for purification of vitamin D metabolites prior to mass spectrometry. In such embodiments, samples may be extracted using a extraction column which captures the analyte, then eluted and chromatographed on a second extraction column or on an analytical HPLC column prior to ionization. For example, sample extraction with a TFLC extraction column may be accomplished with a large particle size (50 µm) packed column. Sample eluted off of this column may then be transferred to an HPLC analytical column for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error.

In some embodiments, protein precipitation is accomplished with a hybrid protein precipitation/liquid-liquid extraction method which includes methanol protein precipitation and ethyl acetate/water extraction from serum. The resulting vitamin D metabolites may be derivatized prior to being subjected to an extraction column. Preferably, the hybrid protein precipitation/liquid-liquid extraction method and the extraction column are connected in an on-line fashion. In preferred embodiments, the extraction column is a C-8 extraction column, such as a Cohesive Technologies C8XL online extraction column (50 µm particle size, 0.5×50 mm) or equivalent. The eluent from the extraction column may then be applied to an analytical LC column, such as a HPLC column in an on-line fashion, prior to mass spectrometric analysis. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation by Mass Spectrometry

In various embodiments, derivatized vitamin D metabolites may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), Laser diode thermal desorption (LDTD), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

Derivatized vitamin D metabolites may be ionized in positive or negative mode. In preferred embodiments, derivatized vitamin D metabolites are ionized by APCI or LDTD in positive ion mode.

In mass spectrometry techniques generally, after the sample has been ionized, the positively or negatively charged ions thereby created may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, mass transitions resulting from collision induced dissociation or neutral loss may be monitored, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

Alternate modes of operating a tandem mass spectrometric instrument include product ion scanning and precursor ion scanning. For a description of these modes of operation, see, e.g., E. Michael Thurman, et al., Chromatographic-Mass Spectrometric Food Analysis for Trace Determination of Pesticide Residues, Chapter 8 (Amadeo R. Fernandez-Alba, ed., Elsevier 2005) (387).

The results of an analyte assay may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of vitamin D metabolites. Methods of generating and using such standard curves are well known in the art and one of ordinary skill is capable of selecting an appropriate internal standard. For example, in preferred embodiments one or more isotopically labeled vitamin D metabolites (e.g., 25OHD$_2$-[6, 19, 19]-$^2$H$_3$ and 25OHD$_3$-[6, 19, 19]-$^2$H$_3$) may be used as internal standards. Numerous other methods for relating the amount of an ion to the amount of the original molecule will be well known to those of ordinary skill in the art.

As used herein, an "isotopic label" produces a mass shift in the labeled molecule relative to the unlabeled molecule when analyzed by mass spectrometric techniques. Examples of suitable labels include deuterium ($^2$H), $^{13}$C, and $^{15}$N. For example, 25OHD$_2$-[6, 19, 19]-$^2$H$_3$ has a mass about three units higher than 25OHD$_2$. The isotopic label can be incorporated at one or more positions in the molecule and one or more kinds of isotopic labels can be used on the same isotopically labeled molecule.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activated dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In particularly preferred embodiments, vitamin D metabolites in a sample are detected and/or quantified using MS/MS as follows. The samples are first purified by protein precipitation or a hybrid protein precipitation/liquid-liquid extraction. Then, one or more vitamin D metabolites in the purified sample are derivatized with a Cookson-type reagent, such as PTAD. The purified samples are then subjected to liquid chromatography, preferably on an extraction column (such as a TFLC column) followed by an analytical column (such as a HPLC column); the flow of liquid solvent from a chromatographic column enters the nebulizer interface of an MS/MS analyzer; and the solvent/analyte mixture is converted to vapor in the heated charged tubing of the interface. The analyte(s) (e.g., derivatized vitamin D metabolites), contained in the solvent, are ionized by applying a large voltage to the solvent/analyte mixture. As the analytes exit the charged tubing of the interface, the solvent/analyte mixture nebulizes and the solvent evaporates, leaving analyte ions. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of derivatized vitamin D metabolites of interest. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. The fragment ions generated are passed into quadrupole 3 (Q3), where the fragment ions of derivatized vitamin D metabolites of interest are selected while other ions are eliminated.

The methods may involve MS/MS performed in either positive or negative ion mode; preferably positive ion mode. Using standard methods well known in the art, one of ordinary skill is capable of identifying one or more fragment ions of a particular precursor ion of derivatized vitamin D metabolites that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of a particular vitamin D metabolite. As described above, the relative abundance of a given ion may be converted into an absolute amount of the original analyte using calibration standard curves based on peaks of one or more ions of an internal molecular standard.

EXAMPLES

Example 1

Hybrid Protein Precipitation/Liquid-Liquid Extraction and Cookson-Type Derivatization The following automated hybrid protein precipitation/liquid-liquid extraction technique was conducted on patient serum samples. Gel Barrier Serum (i.e., serum collected in Serum Separator Tubes) as well as EDTA plasma and Heparin Plasma have also been established as acceptable for this assay.

A Perkin-Elmer Janus robot and a TomTec Quadra Tower robot was used to automate the following procedure. For each sample, 50 µL of serum was added to a well of a 96 well plate. Then 25 µL of internal standard cocktail (containing isotopically labeled 25OHD$_2$-[6, 19, 19]-$^2$H$_3$ and 25OHD$_3$-[6, 19, 19]-$^2$H$_3$) was added to each well, and the plate vortexed. Then 75 µL of methanol was added, followed by additional vortexing. 300 µL of ethyl acetate and 75 µL of water was then added, followed by additional vortexing, centrifugation, and transfer of the resulting supernatant to a new 96-well plate.

The transferred liquid in the second 96-well plate from Example 1 was dried to completion under a flowing nitrogen gas manifold. Derivatization was accomplished by adding 100 µL of a 0.1 mg/mL solution of the Cookson-type derivatization agent PTAD in acetonitrile to each well. The derivatization reaction was allowed to proceed for approximately one hour, and was quenched by adding 100 µL of water to the reaction mixture.

Example 2

Extraction of Vitamin D Metabolites with Liquid Chromatography

Sample injection was performed with a Cohesive Technologies Aria TX-4 TFLC system using Aria OS V 1.5.1 or newer software.

The TFLC system automatically injected an aliquot of the above prepared samples into a Cohesive Technologies C8XL online extraction column (50 µm particle size, 005× 50 mm, from Cohesive Technologies, Inc.) packed with large particles. The samples were loaded at a high flow rate to create turbulence inside the extraction column. This turbulence ensured optimized binding of derivatized vitamin D metabolites to the large particles in the column and the passage of excess derivatizing reagent and debris to waste.

Following loading, the sample was eluted off to the analytical column, a Thermo Hypersil Gold Aq analytical column (5 µm particle size, 50×2.1 mm), with a water/ethanol elution gradient. The HPLC gradient was applied to the analytical column, to separate vitamin D metabolites from other analytes contained in the sample. Mobile phase A was water and mobile phase B was ethanol. The HPLC gradient started with a 35% organic gradient which was ramped to 99% in approximately 65 seconds.

Example 3

Detection and Quantitation of Derivatized Vitamin D Metabolites by MS/MS

MS/MS was performed using a Finnigan TSQ Quantum Ultra MS/MS system (Thermo Electron Corporation). The following software programs, all from Thermo Electron, were used in the Examples described herein: Quantum Tune Master V 1.5 or newer, Xcalibur V 2.07 or newer, LCQuan V 2.56 (Thermo Finnigan) or newer, and ARIA OS v1.5.1 (Cohesive Technologies) or newer. Liquid solvent/analyte exiting the analytical column flowed to the nebulizer interface of the MS/MS analyzer. The solvent/analyte mixture was converted to vapor in the tubing of the interface. Analytes in the nebulized solvent were ionized by ESI.

Ions passed to the first quadrupole (Q1), which selected ions for a derivatized vitamin D metabolite. Ions with a m/z of 570.32±0.50 were selected for PTAD-25OHD$_2$; ions with a m/z of 558.32±0.50 were selected for PTAD-25OHD$_3$. Ions entering quadrupole 2 (Q2) collided with argon gas to generate ion fragments, which were passed to quadrupole 3 (Q3) for further selection. Mass spectrometer settings are shown in Table 1. Simultaneously, the same process using isotope dilution mass spectrometry was carried out with internal standards, PTAD-25OHD$_2$-[6, 19, 19]-$^2$H$_3$ and PTAD-25OHD$_3$-[6, 19, 19]-$^2$H$_3$. The following mass transitions were used for detection and quantitation during validation on positive polarity.

TABLE 1

Mass Spectrometer Settings for Detection of PTAD-25OHD$_2$ and PTAD-25OHD$_3$
Mass Spectrometric Instrument Settings

| | |
|---|---|
| Discharge Current | 4.0 µA |
| Vaporizer Temperature | 300 C. |

TABLE 1-continued

Mass Spectrometer Settings for Detection of PTAD-25OHD$_2$ and PTAD-25OHD$_3$
Mass Spectrometric Instrument Settings

| Setting | Value |
| --- | --- |
| Sheath Gas Pressure | 15 |
| Ion Sweep Gas Pressure | 0.0 |
| Aux Gas Pressure | 5 |
| Capillary Temperature | 300 C. |
| Skimmer Offset | −10 V |
| Collision Pressure | 1.5 mTorr |
| Collision Cell Energy | 15 V |

TABLE 2

Mass Transitions for PTAD-25OHD$_2$, PTAD-25OHD$_2$-[6,19,19]-$^2$H$_3$ (IS), PTAD-25OHD$_3$, and PTAD-25OHD$_3$-[6,19,19]-$^2$H$_3$ (IS) (Positive Polarity)

| Analyte | Precursor Ion (m/z) | Product Ion (m/z) |
| --- | --- | --- |
| PTAD-25OHD$_2$ | 570.32 | 298.09 |
| PTAD-25OHD$_2$-[6,19,19]-$^2$H$_3$ (IS) | 573.32 | 301.09 |
| PTAD-25OHD$_3$ | 558.32 | 298.09 |
| PTAD-25OHD$_3$-[6,19,19]-$^2$H$_3$ (IS) | 561.32 | 301.09 |

Exemplary chromatograms for PTAD-25OHD$_3$, PTAD-25OHD$_3$-[6, 19, 19]-$^2$H$_3$ (internal standard), PTAD-25OHD$_2$, and PTAD-25OHD$_2$-[6, 19, 19]-$^2$H$_3$ (internal standard), are shown in FIGS. 1A, 1B, 1C, and 1D, respectively.

Figure 1:
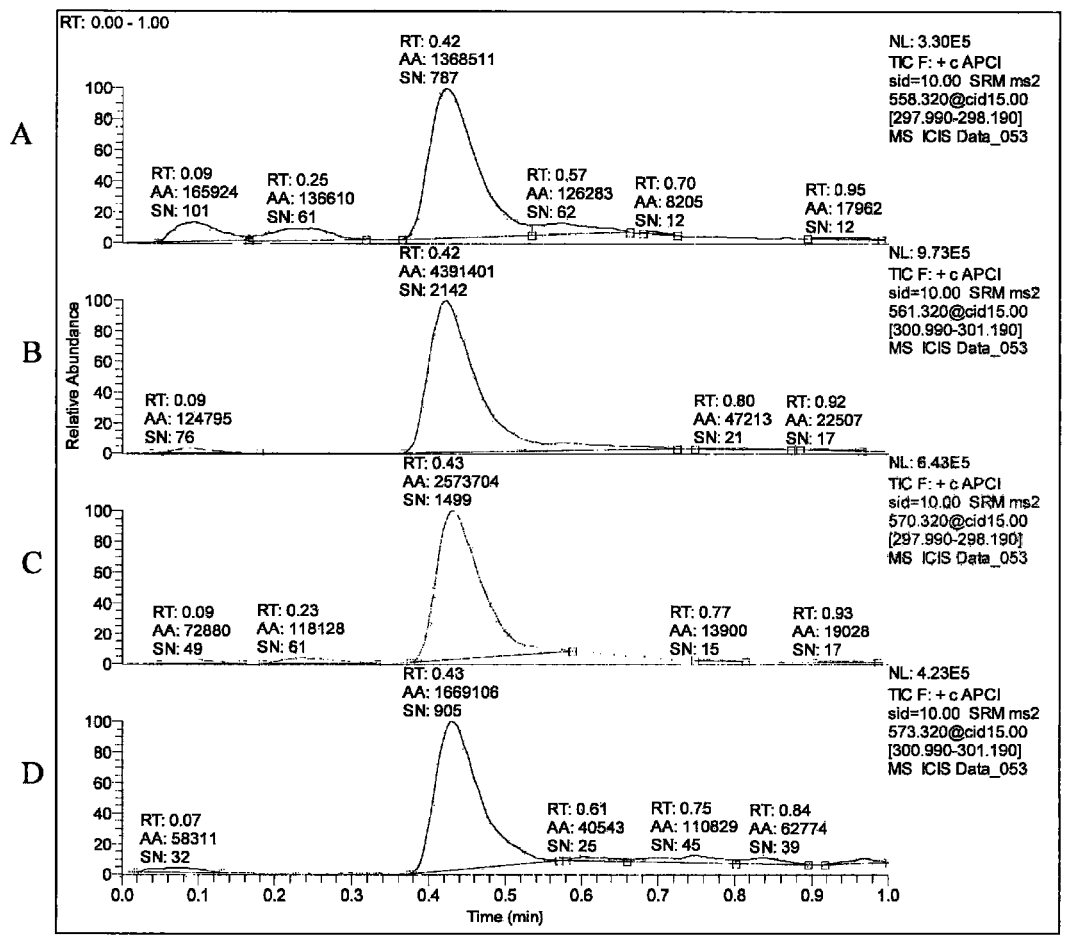
FIGS. 1A-D show exemplary chromatograms for 25OH-$D_3$-PTAD, [6, 19, 19]-$^2H_3$-25OHD$_3$-PTAD (internal standard), 25OHD$_2$-PTAD, and [6, 19, 19]-$^2H_3$-25OHD$_2$-PTAD (internal standard), respectively. Details are discussed in Example 3.
Figure 2A:
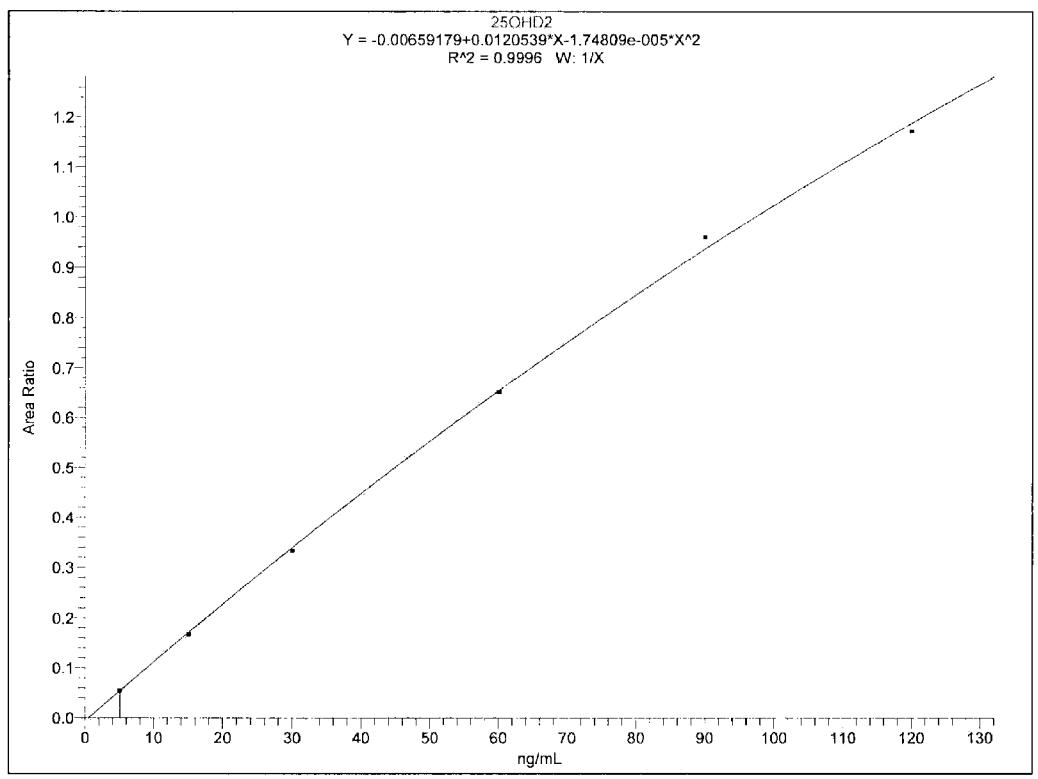
FIGS. 2A and 2B show exemplary calibration curves for 25OHD$_2$ and 25OHD$_3$ in serum samples determined by methods described in Example 3.
Figure 2B:
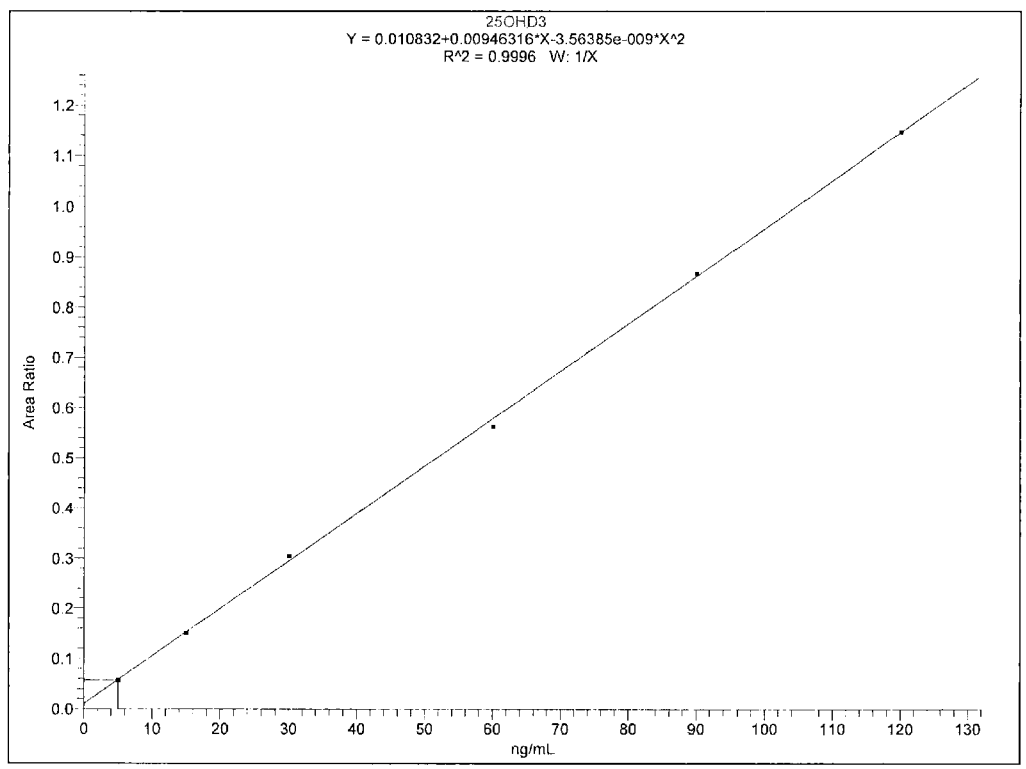

Exemplary calibration curves for the determination of 25OHD$_2$ and 25OHD$_3$ in serum specimens are shown in FIGS. 2A and 2B, respectively.

Example 4

Analytical Sensitivity: Lower Limit of Quantitation (LLOQ) and Limit of Detection (LOD)

Figure 3A:
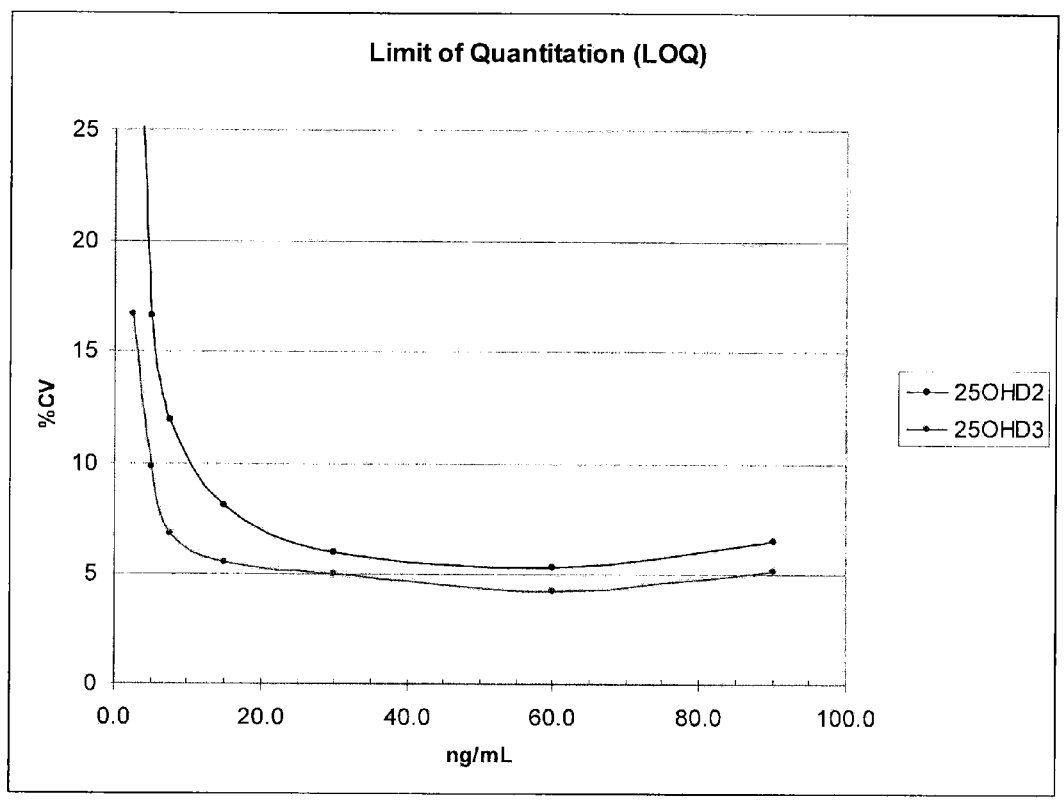
FIG. 3A shows a plots of coefficient of variation versus concentration for 25OHD$_2$ and 25OHD$_3$.
Figure 3B:
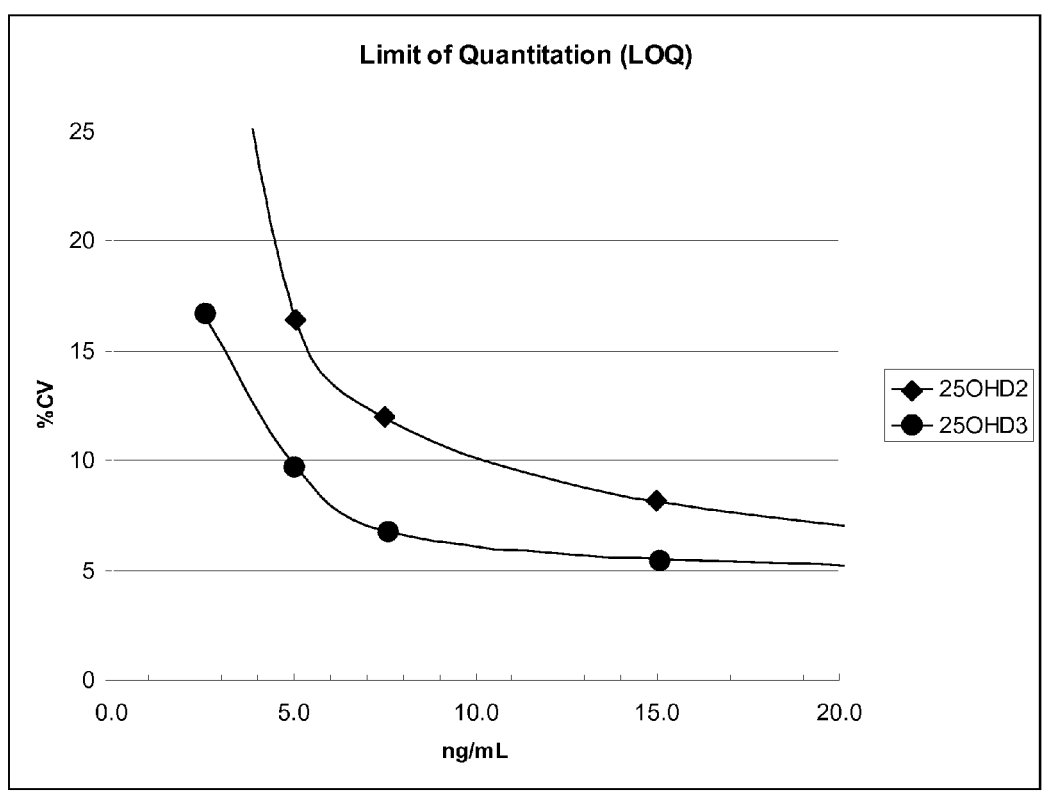
FIG. 3B shows the same plot expanded near the LLOQ. Details are described in Example 4.

The LLOQ is the point where measurements become quantitatively meaningful. The analyte response at this LLOQ is identifiable, discrete and reproducible with a precision (i.e., coefficient of variation (CV)) of greater than 20% and an accuracy of 80% to 120%. The LLOQ was determined by assaying five different human serum samples spiked with PTAD-25OHD$_2$ and PTAD-25OHD$_3$ at levels near the expected LLOQ and evaluating the reproducibility. Analysis of the collected data indicates that samples with concentrations of about 4 ng/mL yielded CVs of about 20%. Thus, the LLOQ of this assay for both PTAD-25OHD$_2$ and PTAD-25OHD$_3$ was determined to be 4 ng/mL. The graphical representations of CV versus concentration for both analytes are shown in FIGS. 3A-B (FIG. 3A shows the plots over an expanded concentration range, while FIG. 3B shows the same plot expanded near the LOQ).

The LOD is the point at which a value is beyond the uncertainty associated with its measurement and is defined as three standard deviations from the zero concentration. To determine the LOD, generally, blank samples of the appropriate matrix are obtained and tested for interferences. However, no appropriate biological matrix could be obtained where the endogenous concentration of 25OHD$_3$ is zero, so a solution of 5% bovine serum albumin in phosphate buffered saline (with an estimated 1.5 ng/mL 25OHD$_3$) was used for LOD studies. The standard was run in 20 replicates each and the resulting area rations were statistically analyzed to determine that the LOD for 25OHD$_2$ and 25OHD$_3$ are 1.9 and 3.3 ng/mL, respectively. Raw data from these studies is presented in Table 3, below

TABLE 3

Limit of Detection Raw Data and Analysis

| Replicate | 25OHD$_2$ (ng/mL) | 25OHD$_3$ (ng/mL) |
| --- | --- | --- |
| 1 | 0.0 | 0.0 |
| 2 | 1.1 | 2.0 |
| 3 | 0.1 | 2.4 |
| 4 | 0.3 | 1.1 |
| 5 | 0.5 | 1.9 |
| 6 | 0.4 | 1.8 |
| 7 | 0.2 | 1.9 |
| 8 | 0.5 | 2.3 |
| 9 | 1.1 | 2.3 |
| 10 | 0.5 | 2.1 |
| 11 | 0.4 | 1.5 |
| 12 | 1.2 | 1.9 |
| 13 | 0.4 | 1.8 |
| 14 | 0.3 | 1.6 |
| 15 | 0.0 | 1.3 |
| 16 | 0.9 | 1.3 |
| 17 | 0.8 | 1.5 |
| 18 | 0.1 | 1.9 |
| 19 | 0.5 | 1.7 |
| 20 | 0.4 | 1.8 |
| Mean | 0.4 | 1.7 |
| SD | 0.5 | 0.5 |
| LOD (Mean + 3SD) | 1.9 | 3.3 |

Example 5

Reportable Range and Linearity

Linearity of derivatized vitamin D metabolite detection in the assay was determined by diluting four pools serum with high endogenous concentration of either 25OHD$_2$ or 25OHD$_3$ and analyzing undiluted specimens and diluted specimens at 1:2, 1:4, and 1:8, in quadruplicate. Quadratic regression of the data was performed yielding correlation coefficients across the concentration range tested of $R^2$=0.97. These studies demonstrated that specimens may be diluted at 1:4 with average recovery of 101%, permitting a reportable range of about 4 to about 512 ng/mL. Average measured values for each of the specimen dilution levels and correlation values from linear regression analysis are presented in Table 4A, below. Percent recoveries for each of the specimen dilution levels are presented in Table 4B, below.

TABLE 4A

Linearity Data and Linear Regression Analysis over Reportable Range

| Dilution Level | 25OHD$_2$ (ng/mL) | | 25OHD$_3$ (ng/mL) | |
| --- | --- | --- | --- | --- |
| | Pool 1 | Pool 2 | Pool 1 | Pool 2 |
| Undiluted | 110.0 | 75.6 | 73.3 | 60.6 |
| 1:2 | 55.5 | 39.3 | 35.7 | 28.7 |
| 1:4 | 26.2 | 19.4 | 18.1 | 16.3 |
| 1:8 | 14.3 | 10.9 | 9.7 | 8.3 |
| $R^2$ | 0.9744 | 0.9721 | 0.9705 | 0.9601 |

TABLE 4B

Percent Recovery at Various Specimen Dilution Levels

| Dilution Level | 25OHD$_2$ (ng/mL) Pool 1 | 25OHD$_2$ (ng/mL) Pool 2 | 25OHD$_3$ (ng/mL) Pool 1 | 25OHD$_3$ (ng/mL) Pool 2 |
|---|---|---|---|---|
| Undiluted | (100%) | (100%) | (100%) | (100%) |
| 1:2 | 100.9 | 104 | 97.4 | 94.8 |
| 1:4 | 95.5 | 102.7 | 98.6 | 107.3 |
| 1:8 | 104.2 | 115.0 | 106.0 | 109.0 |

Example 6

Analyte Specificity

The specificity of the assay against similar analytes was determined to have no cross reactivity for any vitamin D metabolite tested with the exception of 3-epi-25OHD$_3$, which behaves similarly to 25OHD$_3$ in the assay. The side-chain labeled stable isotopes of 25OHD2 and 25OHD$_3$ also showed cross-reactivity owning to hydrogen exchange that occurs in the ion source. Thus, side-chain labeled stable isotopes of 25OHD$_2$ and 25OHD$_3$ should not be used as internal standards. Table 5, below, shows the compounds tested and the results of the cross-reactivity studies.

TABLE 5

Cross-Reactivity Studies (Compounds tested and results)

| Analyte | 25OHD$_2$ | 25OHD$_3$ | Cross-Reactivity |
|---|---|---|---|
| 1,25(OH)$_2$D$_3$ | — | — | No |
| 1,25(OH)$_2$D$_2$ | — | — | No |
| 1,25(OH)$_2$D$_3$-[6,19,19']-$^2$H | — | — | No |
| 1,25(OH)$_2$D$_3$-[26,26,26,27,27,27]-$^2$H | — | — | No |
| 1,25(OH)$_2$D$_2$-[26,26,26,27,27,27]-$^2$H | — | — | No |
| 25OHD$_3$ | — | (100%) | — |
| 25OHD$_2$ | (100%) | — | — |
| 25OHD$_3$-IS-[6,19,19']-$^2$H | — | — | No |
| 25OHD$_2$-IS-[6,19,19']-$^2$H | — | — | No |
| 25OHD$_3$-IS-[26,26,26,27,27,27]-$^2$H | — | 13.8% | Yes |
| 25OHD$_2$-IS-[26,26,26,27,27,27]-$^2$H | 2.7% | — | Yes |
| vitamin D$_3$ | — | — | No |
| vitamin D$_2$ | — | — | No |
| vitamin D$_3$-[6,19,19']-$^2$H | — | — | No |
| vitamin D$_2$-[6,19,19']-$^2$H | — | — | No |
| vitamin D$_3$-[26,26,26,27,27,27]-$^2$H | — | — | No |
| vitamin D$_2$-[26,26,26,27,27,27]-$^2$H | — | — | No |
| 1-OH-D$_3$ (Alfacalcidiol) | — | — | No |
| 1-OH-D$_2$ (Hectoral) | — | — | No |
| 24,25(OH)$_2$D$_3$ | — | — | No |
| 25,26(OH)$_2$D$_3$ | — | — | No |
| 3-epi-25OHD$_3$ | — | — | No |
| 3-epi-1,25(OH)$_2$D$_3$ | — | 33.3% | Yes |
| Dihydrotachysterol | — | — | No |
| 1,25(OH)$_2$D$_3$-26,23-lactone | — | — | No |
| Paracalcitol (Zemplar) | — | — | No |
| Calcipotriene (Dovonex) | — | — | No |
| 7-Dehydrocholesterol | — | — | No |

Example 7

Reproducibility

Six standards at 5, 15, 30, 60, 90, and 120 ng/mL for each analyte were run in every assay as a means as quantitating reproducibility. The day-to-day reproducibility was determined using calibration curves from 19 assays. The data from these 19 assays are presented in Tables 6A (for 25OHD$_2$) and 6B (for 25OHD$_3$).

TABLE 6A

Standard curves demonstrate reproducibility of PTAD-25OHD$_2$ determination

| Assay | 5 ng/mL | 15 ng/mL | 30 ng/mL | 60 ng/mL | 90 ng/mL | 120 ng/mL |
|---|---|---|---|---|---|---|
| 1 | 0.06 | 0.16 | 0.36 | 0.68 | 0.92 | 1.23 |
| 2 | 0.08 | 0.17 | 0.36 | 0.61 | 0.94 | 1.18 |
| 3 | 0.07 | 0.17 | 0.32 | 0.66 | 0.92 | 1.19 |
| 4 | 0.06 | 0.19 | 0.29 | 0.69 | 0.98 | 1.16 |
| 5 | 0.07 | 0.15 | 0.37 | 0.60 | 0.85 | 1.13 |
| 6 | 0.07 | 0.16 | 0.32 | 0.64 | 0.95 | 1.20 |
| 7 | 0.07 | 0.16 | 0.35 | 0.63 | 0.99 | 1.18 |
| 8 | 0.06 | 0.16 | 0.35 | 0.60 | 0.98 | 1.31 |
| 9 | 0.06 | 0.18 | 0.32 | 0.66 | 0.96 | 1.10 |
| 10 | 0.06 | 0.15 | 0.35 | 0.62 | 0.89 | 1.22 |
| 11 | 0.05 | 0.17 | 0.33 | 0.65 | 0.96 | 1.17 |
| 12 | 0.04 | 0.17 | 0.32 | 0.61 | 0.97 | 1.12 |
| 13 | 0.05 | 0.16 | 0.34 | 0.62 | 0.97 | 1.30 |
| 14 | 0.06 | 0.17 | 0.31 | 0.61 | 0.95 | 1.21 |
| 15 | 0.07 | 0.16 | 0.34 | 0.70 | 0.94 | 1.30 |
| 16 | 0.08 | 0.17 | 0.39 | 0.70 | 1.06 | 1.27 |
| 17 | 0.06 | 0.15 | 0.36 | 0.65 | 1.03 | 1.20 |
| 18 | 0.05 | 0.18 | 0.34 | 0.81 | 0.91 | 1.33 |
| 19 | 0.06 | 0.17 | 0.30 | 0.62 | 1.06 | 1.21 |
| Avg | 0.06 | 0.16 | 0.34 | 0.65 | 0.96 | 1.21 |
| SD | 0.01 | 0.01 | 0.02 | 0.05 | 0.05 | 0.07 |
| CV % | 15.4 | 6.3 | 7.4 | 8.0 | 5.6 | 5.4 |

TABLE 6B

Standard curves demonstrate reproducibility of PTAD-25OHD$_3$ determination

| Assay | 5 ng/mL | 15 ng/mL | 30 ng/mL | 60 ng/mL | 90 ng/mL | 120 ng/mL |
|---|---|---|---|---|---|---|
| 1 | 0.07 | 0.16 | 0.36 | 0.61 | 0.95 | 1.19 |
| 2 | 0.07 | 0.17 | 0.32 | 0.66 | 1.01 | 1.12 |
| 3 | 0.06 | 0.16 | 0.32 | 0.60 | 1.00 | 1.16 |
| 4 | 0.06 | 0.17 | 0.31 | 0.60 | 0.94 | 1.09 |
| 5 | 0.05 | 0.16 | 0.33 | 0.65 | 0.96 | 1.11 |
| 6 | 0.07 | 0.17 | 0.34 | 0.65 | 0.87 | 1.13 |
| 7 | 0.07 | 0.17 | 0.31 | 0.61 | 0.95 | 1.21 |
| 8 | 0.06 | 0.15 | 0.29 | 0.58 | 0.90 | 1.21 |
| 9 | 0.07 | 0.17 | 0.32 | 0.65 | 0.88 | 1.15 |
| 10 | 0.06 | 0.14 | 0.30 | 0.57 | 1.05 | 1.16 |
| 11 | 0.06 | 0.15 | 0.30 | 0.56 | 0.87 | 1.15 |
| 12 | 0.05 | 0.15 | 0.31 | 0.64 | 0.85 | 1.06 |
| 13 | 0.06 | 0.16 | 0.33 | 0.60 | 0.88 | 1.08 |
| 14 | 0.06 | 0.17 | 0.31 | 0.61 | 0.91 | 1.22 |
| 15 | 0.06 | 0.18 | 0.34 | 0.66 | 0.96 | 1.18 |
| 16 | 0.06 | 0.17 | 0.35 | 0.65 | 0.94 | 1.21 |
| 17 | 0.06 | 0.17 | 0.36 | 0.64 | 0.94 | 1.17 |
| 18 | 0.07 | 0.17 | 0.34 | 0.66 | 0.98 | 1.18 |
| 19 | 0.07 | 0.16 | 0.34 | 0.68 | 0.84 | 1.27 |
| Avg | 0.06 | 0.16 | 0.33 | 0.63 | 0.93 | 1.16 |
| SD | 0.00 | 0.01 | 0.02 | 0.03 | 0.06 | 0.05 |
| CV % | 7.9 | 5.8 | 5.9 | 5.5 | 6.1 | 4.6 |

Example 8

Intra-Assay and Inter-Assay Variation Studies

Intra-assay variation is defined as the reproducibility of results for a sample within a single assay. To assess intra-assay variation, twenty replicates from each of four quality control (QC) pools covering the reportable range of the assay were prepared and measured from pooled serum with 25OHD$_2$ and 25OHD$_3$ at arbitrary ultralow, low, medium, and high concentrations for each analyte. Acceptable levels for the coefficient of variation (CV) are less then 15% for the three higher concentration, and less than 20% for the lowest concentration (at or near the LOQ for the assay).

The results of the intra-assay variation studies indicate that the CV for the four QC pools are 9.1%, 6.4%, 5.0%, and 5.9% with mean concentrations of 13.7 ng/mL, 30.0 ng/mL, 52.4 ng/mL, and 106.9 ng/mL, respectively, for PTAD-25OHD$_2$, and 3.5%, 4.9%, 5.1%, and 3.3% with mean concentrations of 32.8 ng/mL, 15.0 ng/mL, 75.4 ng/mL, and 102.3 ng/mL, respectively, for PTAD-25OHD$_3$. The data from analysis of these replicates is shown in Tables 7A and 7B.

Five aliquots of each of the same four QC pools were assayed over six days to determine the coefficient of variation (CV) between assays. The results of the intra-assay variation studies indicate that the inter-assay CV for the four QC pools are 8.3%, 6.2%, 8.1%, and 6.4% with mean concentrations of 13.1 ng/mL, 29.8 ng/mL, 51.9 ng/mL, and 107.8 ng/mL, respectively, for PTAD-25OHD$_2$, and 4.8%, 6.7%, 4.7%, and 6.7% with mean concentrations of 31.1 ng/mL, 14.5 ng/mL, 75.1 ng/mL, and 108.4 ng/mL, respectively, for PTAD-25OHD$_3$. The data from analysis of these replicates is shown in Tables 8A and 8B.

TABLE 7A

PTAD-25OHD$_2$ Intra-assay variation studies

| Replicate | QC (U) Lot # 090837 ng/mL | QC (L) Lot # 090838 ng/mL | QC (M) Lot # 090839 ng/mL | QC (H) Lot # 090840 ng/mL |
|---|---|---|---|---|
| 1 | 15.2 | 31.4 | 49.5 | 108.9 |
| 2 | 12.3 | 29.7 | 53.2 | 109.3 |
| 3 | 13.8 | 30.8 | 50.9 | 98.9 |
| 4 | 12.4 | 30.1 | 50.4 | 111.5 |
| 5 | 14.6 | 27.2 | 49.7 | 109.0 |
| 6 | 14.6 | 29.1 | 47.6 | 110.3 |
| 7 | 13.6 | 33.0 | 53.3 | 95.6 |
| 8 | 11.4 | 29.9 | 53.3 | 98.5 |
| 9 | 14.0 | 31.5 | 55.2 | 110.7 |
| 10 | 13.7 | 29.1 | 49.0 | 113.5 |
| 11 | 13.7 | 29.5 | 56.8 | 100.4 |
| 12 | 13.0 | 25.5 | 54.1 | 105.4 |
| 13 | 15.6 | 34.2 | 53.6 | 102.0 |
| 14 | 11.7 | 28.7 | 52.9 | 103.2 |
| 15 | 13.5 | 28.1 | 49.4 | 121.0 |
| 16 | 13.6 | 29.8 | 52.0 | 102.9 |
| 17 | 13.1 | 29.4 | 56.8 | 113.4 |
| 18 | 14.4 | 30.6 | 54.5 | 103.3 |
| 19 | 16.2 | 31.6 | 53.1 | 110.8 |
| 20 | 12.7 | 30.7 | — | 110.4 |
| Avg | 0.06 | 0.16 | 0.33 | 0.63 |
| SD | 0.00 | 0.01 | 0.02 | 0.03 |
| CV % | 7.9 | 5.8 | 5.9 | 5.5 |

TABLE 7B

PTAD-25OHD$_3$ Intra-assay variation studies

| Replicate | QC (U) Lot # 090837 ng/mL | QC (L) Lot # 090838 ng/mL | QC (M) Lot # 090839 ng/mL | QC (H) Lot # 090840 ng/mL |
|---|---|---|---|---|
| 1 | 34.4 | 13.7 | 75.7 | 101.7 |
| 2 | 35.0 | 14.2 | 78.7 | 101.8 |
| 3 | 33.2 | 14.7 | 73.1 | 103.2 |
| 4 | 34.4 | 14.9 | 83.7 | 104.1 |
| 5 | 32.4 | 14.5 | 72.7 | 107.0 |
| 6 | 33.3 | 14.3 | 73.6 | 107.6 |
| 7 | 33.8 | 15.0 | 79.1 | 97.5 |
| 8 | 32.1 | 15.8 | 73.1 | 98.7 |
| 9 | 32.4 | 15.5 | 74.2 | 106.5 |
| 10 | 31.4 | 15.4 | 74.5 | 106.1 |
| 11 | 31.8 | 14.7 | 69.3 | 105.9 |
| 12 | 31.2 | 16.8 | 73.5 | 97.7 |
| 13 | 34.1 | 15.4 | 72.7 | 104.9 |
| 14 | 33.8 | 15.3 | 75.1 | 99.8 |
| 15 | 32.0 | 15.7 | 76.2 | 102.2 |
| 16 | 33.2 | 14.7 | 74.2 | 102.2 |
| 17 | 32.6 | 14.7 | 85.0 | 100.5 |
| 18 | 31.6 | 13.9 | 75.5 | 101.8 |
| 19 | 31.3 | 15.6 | 73.6 | 99.9 |
| 20 | 32.5 | 15.3 | — | 96.3 |
| Avg | 32.8 | 15.0 | 75.4 | 102.3 |
| SD | 1.1 | 0.7 | 3.8 | 3.4 |
| CV % | 3.5 | 4.9 | 5.1 | 3.3 |

TABLE 8A

PTAD-25OHD$_2$ Inter-assay variation studies

| Assay | QC (U) Lot # 090837 ng/mL | QC (L) Lot # 090838 ng/mL | QC (M) Lot # 090839 ng/mL | QC (H) Lot # 090840 ng/mL |
|---|---|---|---|---|
| 1 | 13.6 | 28.1 | 51.7 | 119.6 |
|   | 12.8 | 30.1 | 49.4 | 117.9 |
|   | 14.6 | 32.0 | 49.7 | 105.1 |
|   | 13.0 | 30.8 | 52.3 | 100.2 |
|   | 13.0 | 29.2 | 56.6 | 110.3 |
| 2 | 12.9 | 31.3 | 46.3 | 108.1 |
|   | 13.5 | 30.3 | 52.1 | 117.8 |
|   | 10.9 | 29.7 | 46.9 | 105.8 |
|   | 11.2 | 30.6 | 43.6 | 105.2 |
|   | 12.8 | 28.7 | 50.3 | 104.9 |
| 3 | 12.6 | 28.8 | 56.5 | 115.3 |
|   | 16.4 | 29.3 | 63.8 | 103.0 |
|   | 13.2 | 26.2 | 45.5 | 103.2 |
|   | 11.5 | 30.8 | 53.8 | 113.2 |
|   | 12.4 | 33.7 | 51.6 | 106.9 |
| 4 | 12.1 | 28.5 | 58.5 | 97.0 |
|   | 13.9 | 26.2 | 51.8 | 115.1 |
|   | 14.4 | 29.6 | 48.9 | 112.2 |
|   | 13.1 | 32.1 | 52.3 | 97.9 |
|   | 12.6 | 30.5 | 52.2 | 104.2 |
| 5 | 12.7 | 29.9 | 54.5 | 101.3 |
|   | 14.3 | 28.3 | 46.3 | 102.2 |
|   | 13.9 | 30.0 | 56.1 | 111.4 |
|   | 13.1 | 32.6 | 51.2 | 123.1 |
|   | 12.4 | 26.2 | 51.2 | 98.3 |
| 6 | 12.5 | 30.6 | 50.1 | 104.6 |
|   | 12.9 | 32.6 | 51.8 | 104.8 |
|   | 14.0 | 28.6 | 53.7 | 108.9 |
|   | 14.3 | 29.1 | 51.0 | 113.8 |
|   | 12.9 | 29.1 | 56.4 | 102.2 |
| Avg | 13.1 | 29.8 | 51.9 | 107.8 |
| SD | 1.1 | 1.8 | 4.2 | 6.8 |
| CV % | 8.3 | 6.2 | 8.1 | 6.4 |

TABLE 8B

PTAD-25OHD$_3$ Inter-assay variation studies

| Assay | QC (U) Lot # 090837 ng/mL | QC (L) Lot # 090838 ng/mL | QC (M) Lot # 090839 ng/mL | QC (H) Lot # 090840 ng/mL |
|---|---|---|---|---|
| 1 | 32.6 | 13.4 | 76.7 | 104.9 |
|   | 30.0 | 12.7 | 77.6 | 107.0 |
|   | 34.1 | 15.4 | 78.4 | 107.1 |
|   | 34.0 | 14.8 | 76.6 | 105.1 |
|   | 30.2 | 15.5 | 74.8 | 110.2 |
| 2 | 33.5 | 13.2 | 69.8 | 109.8 |
|   | 32.4 | 14.3 | 75.0 | 106.4 |
|   | 30.2 | 16.2 | 73.4 | 112.1 |
|   | 31.4 | 16.1 | 71.9 | 97.0 |
|   | 31.4 | 13.7 | 75.2 | 117.5 |
| 3 | 31.5 | 13.3 | 70.2 | 112.4 |
|   | 32.1 | 14.6 | 82.6 | 101.5 |
|   | 31.0 | 15.4 | 70.8 | 99.8 |

TABLE 8B-continued

PTAD-25OHD$_3$ Inter-assay variation studies

| Assay | QC (U) Lot # 090837 ng/mL | QC (L) Lot # 090838 ng/mL | QC (M) Lot # 090839 ng/mL | QC (H) Lot # 090840 ng/mL |
|---|---|---|---|---|
|  | 28.7 | 15.6 | 74.3 | 103.6 |
|  | 30.7 | 15.1 | 79.8 | 99.1 |
| 4 | 31.9 | 14.5 | 76.3 | 124.2 |
|  | 27.5 | 14.0 | 70.5 | 113.6 |
|  | 27.9 | 14.8 | 74.5 | 112.5 |
|  | 32.1 | 16.1 | 74.3 | 108.8 |
|  | 31.0 | 14.4 | 74.5 | 110.1 |
| 5 | 31.2 | 13.1 | 76.7 | 96.5 |
|  | 31.5 | 13.5 | 82.9 | 106.1 |
|  | 31.5 | 14.7 | 70.9 | 112.9 |
|  | 30.9 | 14.5 | 77.6 | 117.7 |
|  | 31.0 | 13.9 | 73.1 | 101.9 |
| 6 | 29.8 | 15.6 | 73.3 | 110.1 |
|  | 30.5 | 13.5 | 71.5 | 99.3 |
|  | 31.0 | 13.9 | 72.6 | 120.5 |
|  | 30.5 | 14.6 | 74.2 | 109.4 |
|  | 30.7 | 13.6 | 81.8 | 115.9 |
| Avg | 31.1 | 14.5 | 75.1 | 108.4 |
| SD | 1.5 | 1.0 | 3.6 | 6.9 |
| CV % | 4.8 | 6.7 | 4.7 | 6.4 |

Example 9

Recovery Studies

Two recovery studies were performed. The first was performed using six specimens, spiked with two different concentrations each of 25OHD$_2$ and 25OHD$_3$. These spiked specimens were analyzed in quadruplicate. The spiked concentrations were within the workable range of the assay. The six pools yielded an average accuracy of 89% at spiked levels of grater than 44 ng/mL and 92% at spiked levels of greater than 73 ng/mL. Only two of the 24 experimental recoveries were less than 85%; the remaining 22 assays were within the acceptable accuracy range of 85-115%. The results of the spiked specimen recovery studies are presented in Table 9, below.

TABLE 9

Spiked Specimen Recovery Studies

| | | 25OHD$_2$ | | 25OHD$_3$ | |
|---|---|---|---|---|---|
| Pool | Spike Level | ng/mL | (% Recovery) | ng/mL | (% Recovery) |
| 1 | — | 12.0 | — | 10.8 | — |
|  | 44 ng/ml 25OHD$_2$ | 48.0 | 81.2 | 10.7 | — |
|  | 73 ng/mL 25OHD$_2$ | 79.0 | 91.6 | 10.7 | — |
|  | 44 ng/mL 25OHD$_3$ | 12.7 | — | 51.9 | 92.9 |
|  | 73 ng/mL 25OHD$_3$ | 11.5 | — | 76.5 | 89.9 |
| 2 | — | 11.9 | — | 10.8 | — |
|  | 44 ng/mL 25OHD$_2$ | 48.0 | 81.4 | 10.6 | — |
|  | 73 ng/mL 25OHD$_2$ | 75.6 | 87.1 | 11.0 | — |
|  | 44 ng/mL 25OHD$_3$ | 10.0 | — | 48.8 | 85.6 |
|  | 73 ng/mL 25OHD$_3$ | 11.6 | — | 76.4 | 89.7 |
| 3 | — | 13.6 | — | 6 | — |
|  | 44 ng/mL 25OHD$_2$ | 52.5 | 87.8 | 10.9 | — |
|  | 73 ng/mL 25OHD$_2$ | 76.8 | 86.4 | 10.5 | — |
|  | 44 ng/mL 25OHD$_3$ | 13.2 | — | 49.6 | 88.0 |
|  | 73 ng/mL 25OHD$_3$ | 12.3 | — | 78.0 | 92.2 |
| 4 | — | 9.0 | — | 12.7 | — |
|  | 44 ng/mL 25OHD$_2$ | 50.3 | 93.1 | 13.5 | — |
|  | 73 ng/mL 25OHD$_2$ | 77.6 | 93.8 | 13.2 | — |
|  | 44 ng/mL 25OHD$_3$ | 10.0 | — | 52.1 | 89.0 |
|  | 73 ng/mL 25OHD$_3$ | 9.5 | — | 83.6 | 97.0 |
| 5 | — | 21.8 | — | 14.0 | — |
|  | 44 ng/mL 25OHD$_2$ | 68.0 | 104.2 | 13.3 | — |
|  | 73 ng/mL 25OHD$_2$ | 91.1 | 94.8 | 13.6 | — |
|  | 44 ng/mL 25OHD$_3$ | 23.3 | — | 53.5 | 89.1 |
|  | 73 ng/mL 25OHD$_3$ | 22.2 | — | 86.4 | 99.1 |
| 6 | — | 13.8 | — | 9.3 | — |
|  | 44 ng/mL 25OHD$_2$ | 50.6 | 83.0 | 9.2 | — |
|  | 73 ng/mL 25OHD$_2$ | 83.9 | 95.9 | 9.5 | — |
|  | 44 ng/mL 25OHD$_3$ | 13.5 | — | 48.6 | 88.6 |
|  | 73 ng/mL 25OHD$_3$ | 13.2 | — | 76.5 | 91.9 |

The second recovery study was performed again using six specimens. Of these six specimens, three had high endogenous concentration of 25OHD$_2$ and three had high endogenous concentrations of 25OHD$_3$. The specimens were paired and mixed at ratios of 4:1, 1:1, and 1:4, and the resulting mixtures analyzed in quadruplicate. These experiments yielded an average accuracy of 98% for 25OHD$_2$ and 93% for 25OHD$_3$. All individual results were within the acceptable accuracy range of 85-115%. The results of the mixed specimen recovery studies are presented in Table 10, below.

TABLE 10

Mixed Specimen Recovery Studies

| | 25OHD$_2$ | | | 25OHD$_3$ | | |
|---|---|---|---|---|---|---|
| Specimen Mixture | Measured ng/mL | Expected ng/mL | Recovery (%) | Measured ng/mL | Expected ng/mL | Recovery (%) |
| 100% A | 45.2 | — | — | 5.5 | — | — |
| 4:1 A:B | 37.1 | 37.0 | 100 | 11.6 | 13.1 | 88 |
| 1:1 A:B | 26.4 | 24.6 | 107 | 24.4 | 24.4 | 100 |
| 1:4 A:B | 12.6 | 12.3 | 102 | 33.9 | 35.7 | 95 |
| 100% B | 4.1 | — | — | 43.3 | — | — |
| 100% C | 46.8 | — | — | 8.3 | — | — |
| 4:1 C:D | 38.1 | 38.7 | 98 | 17.7 | 18.3 | 97 |
| 1:1 C:D | 25.0 | 26.6 | 94 | 32.0 | 33.4 | 96 |
| 1:4 C:D | 14.4 | 14.4 | 100 | 46.5 | 48.4 | 96 |
| 100% D | 6.3 | — | — | 58.5 | — | — |
| 100% E | 38.7 | — | — | 7.4 | — | — |
| 4:1 E:F | 33.4 | 34.3 | 97 | 15.7 | 17.5 | 89 |
| 1:1 E:F | 27.1 | 27.7 | 98 | 27.8 | 32.6 | 85 |
| 1:4 E:F | 18.3 | 21.0 | 87 | 44.0 | 47.7 | 92 |
| 100% F | 16.6 | — | — | 57.8 | — | — |

*Measured values are averages of analysis of four aliquots.

Example 10

Method Correlation Study

The method of detecting vitamin D metabolites following PTAD-derivatization was compared to a mass spectrometric method in which the vitamin D metabolites are not derivatized prior to analysis. Such a method is described in the published U.S. Patent Application 2006/0228808 (Caulfield, et al.). Eight specimens were split and analyzed according to both methods. The correlation between the two methods was assessed with linear regression, deming regression, and Bland-Altman analysis for complete data sets (including calibration samples, QC pools, and unknowns), as well as for unknowns only.

Figure 4A:
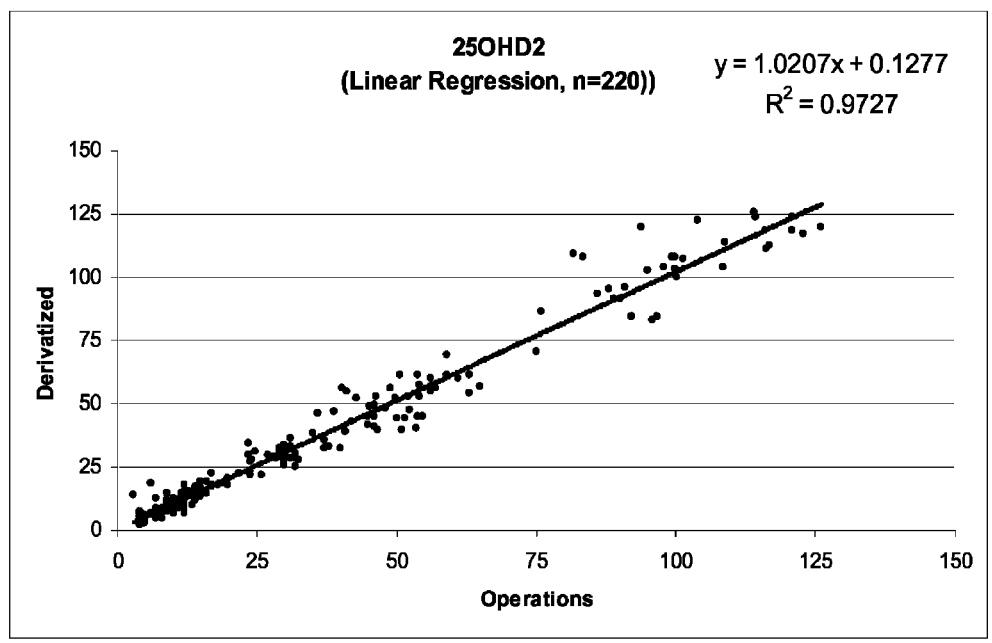
FIGS. 4A-B show linear regression and Deming regression analyses for the comparison of mass spectrometric determination of 25OHD$_2$ with and without PTAD derivatization. Details are described in Example 10.
Figure 4B:
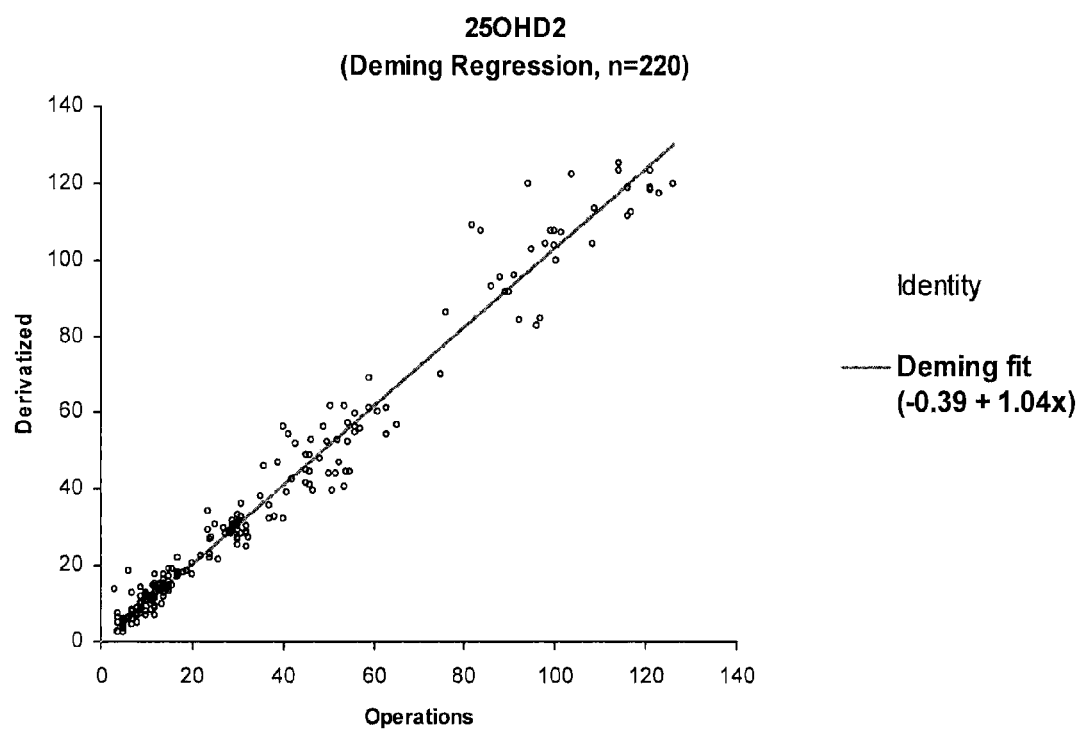
Figure 5A:
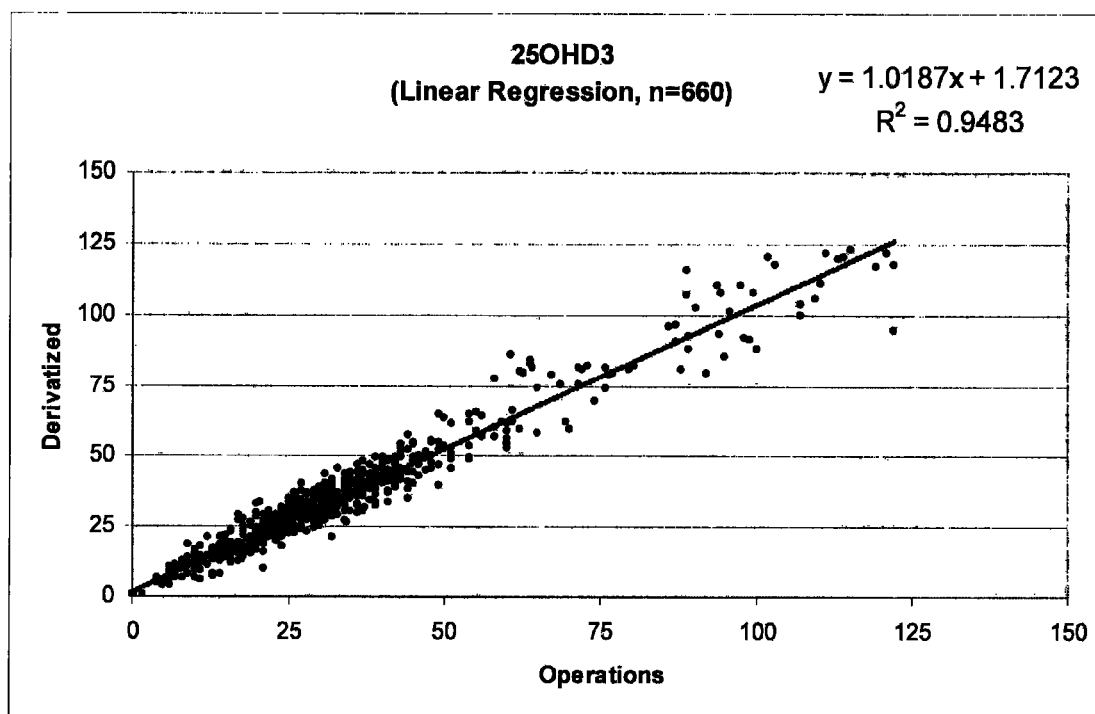
FIGS. 5A-B show linear regression and Deming regression analyses for the comparison of mass spectrometric determination of 25OHD$_3$ with and without PTAD derivatization. Details are described in Example 10.
Figure 5B:
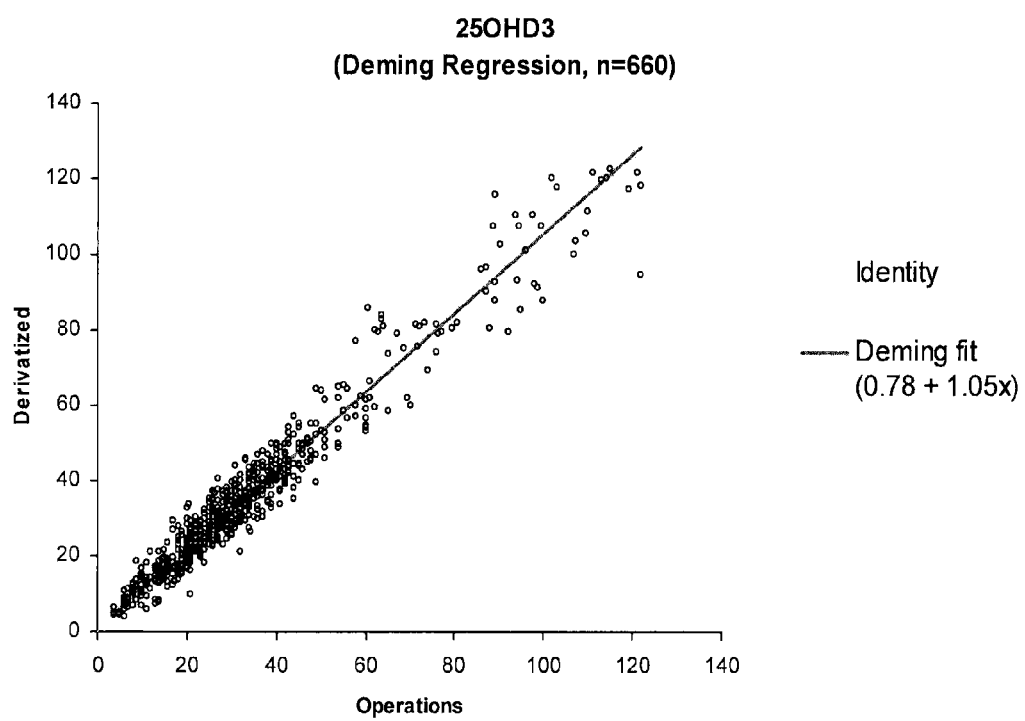

Plots of the linear regression analysis and the Deming regression analysis are shown in FIGS. 4A-B (for 25OHD$_2$) and FIGS. 5A-B (for 25OHD$_3$).

Example 11

Hemolysis, Lipemia, and Icteria Studies

The effect hemolysis, lipemia, and icteria have on the assay was also investigated.

Hemolysis.

The effect of hemolysis was evaluated by pooling patient samples with known endogenous concentrations of both 25OHD$_2$ and 25OHD$_3$ to create five different pools with concentrations across the dynamic range of the assay. Then, lysed whole blood was spiked into the pools to generate lightly and moderately hemolyzed samples.

The lightly and moderately hemolyzed samples were analyzed in quadruplicate and the results were compared to levels of samples without whole blood spikes. The resulting comparison indicated a % difference of less than 15% for both 25OHD$_2$ and 25OHD$_3$. Therefore, light to moderately hemolyzed specimens are acceptable for analysis.

Lipemia.

The effect of lipemia was evaluated by pooling patient samples with known endogenous concentrations of both 25OHD$_2$ and 25OHD$_3$ to create five different pools with concentrations across the dynamic range of the assay. Then, powdered lipid extract was added to the pools to generate lightly and grossly lipemic specimens. Specimens were run in quadruplicate and results were compared to the non-lipemic pool result and the accuracy was calculated. The data shows that determination of 25OHD$_2$ is unaffected by lipemia (all values were within an acceptable accuracy range of 85-115%), however, 25OHD$_3$ is affected by lipemia, resulting in determination in lower than expected values. The degree of variance increased with the degree of lipemia. Therefore, light but not grossly lipemic specimens are acceptable.

Icteria.

The effect of icteria was evaluated by pooling patient samples with known endogenous concentrations of both 25OHD$_2$ and 25OHD$_3$ to create five different pools with concentrations across the dynamic range of the assay. Then, a concentrated solution of Bilirubin was spiked into the pools to generate lightly and grossly icteric specimens. Specimens were run in quadruplicate and results were compared to the non-icteric pool result and the accuracy was calculated. The data showed that 25OHD$_2$ and 25OHD$_3$ are unaffected by icteria (with all values within an acceptable accuracy range of 85-115%). Therefore, icteric specimens are acceptable.

Example 12

Injector Carryover Studies

Blank matrices were run immediately after a specimen with a high concentration of 25OHD$_2$ and 25OHD$_3$ in order to evaluate carryover between samples. These studies indicated that the response at the retention time of analyte or internal standard was not large enough to compromise the integrity of the assay. Data from these studies is presented in Table 11, below.

TABLE 11

Injector Carryover Study Results

| Injection | Specimen Type | 25OHD$_2$ (ng/mL) | 25OHD$_3$ (ng/mL) |
|---|---|---|---|
| 1 | Blank | 0.9 | 1.6 |
| 2 | High | 292.6 | 356.8 |
| 3 | Blank | 1.0 | 0.9 |
| 4 | Blank | −0.1 | 0.5 |
| 5 | High | 290.1 | 360.1 |
| 6 | High | 299.9 | 350.5 |
| 7 | Blank | 1.0 | 1.5 |
| 8 | Blank | 0.6 | 1.4 |
| 9 | Blank | 1.3 | 1.4 |
| 10 | High | 285.8 | 352.1 |
| 11 | High | 303.1 | 312.1 |
| 12 | High | 293.8 | 295.1 |
| 13 | Blank | 0.9 | 0.8 |
| 14 | Blank | 1.0 | 1.8 |
| 15 | Blank | 1.1 | 1.4 |
| 16 | Blank | 1.0 | 1.6 |
| 17 | High | 291.7 | 371.6 |
| 18 | High | 334.2 | 360.1 |
| 19 | High | 301.7 | 328.5 |
| 20 | High | 283.1 | 382.1 |
| 21 | Blank | 0.6 | 1.1 |
| 22 | Blank | 0.6 | 1.3 |
| 23 | Blank | 0.7 | 1.4 |
| 24 | Blank | 0.4 | 1.9 |
| 25 | Blank | 0.4 | 0.9 |
| 26 | High | 300.7 | 311.7 |
| 27 | High | 279.5 | 302.0 |
| 28 | High | 317.5 | 341.0 |
| 29 | High | 261.5 | 403.4 |
| 30 | High | 288.3 | 362.6 |
| 31 | Blank | 2.7 | 1.6 |
| 32 | Blank | 1.7 | 1.2 |
| 33 | Blank | 0.5 | 1.3 |
| 34 | Blank | 1.3 | 1.7 |
| 35 | Blank | 0.3 | 1.6 |
| 36 | Blank | 0.6 | 1.4 |
| 37 | High | 311.7 | 366.2 |
| 38 | High | 314.1 | 342.0 |
| 39 | High | 325.7 | 349.1 |
| 40 | High | 289.6 | 326.6 |
| 41 | High | 291.5 | 322.3 |
| 42 | High | 278.9 | 336.5 |
| 43 | Blank | 2.1 | 2.5 |
| 44 | Blank | 0.6 | 1.6 |
| 45 | Blank | 0.7 | 1.4 |
| 46 | Blank | 0.7 | 1.5 |
| 47 | Blank | 0.1 | 1.0 |
| 48 | Blank | 0.7 | 1.1 |
| 49 | Blank | 1.3 | 1.0 |
| 50 | High | 281.2 | 345.6 |
| 51 | High | 312.5 | 348.3 |
| 52 | High | 304.8 | 329.1 |
| 53 | High | 290.5 | 353.9 |
| 54 | High | 286.4 | 344.9 |
| 55 | High | 302.5 | 330.6 |

TABLE 11-continued

Injector Carryover Study Results

| Injection | Specimen Type | 25OHD$_2$ (ng/mL) | 25OHD$_3$ (ng/mL) |
|---|---|---|---|
| 56 | High | 292.2 | 388.5 |
| 57 | Blank | 0.8 | 1.5 |
| 58 | Blank | 1.3 | 1.4 |
| 59 | Blank | 3.5 | 2.6 |
| 60 | Blank | 0.4 | 1.8 |
| 61 | Blank | 1.0 | 1.4 |
| 62 | Blank | 1.0 | 1.2 |
| 63 | Blank | 0.7 | 1.0 |
| 64 | Blank | 1.1 | 1.4 |
| 65 | High | 285.4 | 355.4 |
| 66 | High | 318.0 | 355.0 |
| 67 | High | 285.5 | 345.7 |
| 68 | High | 303.0 | 317.1 |
| 69 | High | 276.3 | 351.4 |
| 70 | High | 321.8 | 350.4 |
| 71 | High | 279.4 | 329.6 |
| 72 | High | 299.1 | 337.9 |
| 73 | Blank | 0.9 | 1.6 |
| 74 | Blank | 1.7 | 1.6 |
| 75 | Blank | 1.0 | 1.1 |
| 76 | Blank | 1.8 | 2.7 |
| 77 | Blank | 1.0 | 1.9 |
| 78 | Blank | 0.6 | 1.1 |
| 79 | Blank | 0.9 | 0.9 |
| 80 | Blank | 1.2 | 2.2 |

Example 13

Suitable Specimen Types

The assay was conducted on various specimen types. Human serum and Gel-Barrier Serum (i.e., serum from Serum Separator Tubes), as well as EDTA Plasma and Heparin were established as acceptable sample types. In these studies, sets of human serum (serum), Gel-Barrier Serum (SST), EDTA Plasma (EDTA), and heparin (Na Hep) drawn at the same time from the same patient were tested for 25OHD$_2$ (40 specimen sets) and 25OHD$_3$ (6 specimen sets). Due to the limitations with clot detection/sensing in existing automated pipetting systems, plasma was not tested for automated procedures.

The results of the specimen type studies are presented in Tables 12A and B for 25OHD$_2$ and 25OHD$_3$, respectively.

TABLE 12A

Results from Specimen Type Studies for 25OHD$_2$

| Specimen Set | CC ID# | Measured Concentration 25OHD$_2$ (ng/mL) | | | |
|---|---|---|---|---|---|
| | | Serum | SST | EDTA | Na Hep |
| 2 | 5207 | 6.6 | 6.9 | 7.1 | 7.2 |
| 6 | 5339 | 5.8 | 5.2 | 4.5 | 5.6 |
| 11 | 5355 | 7.8 | 8.2 | 8.8 | 8.2 |
| 20 | 5493 | 3.9 | 4.2 | 4.3 | 4.2 |
| 37 | 5650 | 3.7 | 4.5 | 4.6 | 5.2 |
| 39 | 5653 | 4.7 | 5.1 | 4.6 | 4.7 |

TABLE 12B

Results from Specimen Type Studies for 25OHD$_3$

| Specimen Set | CC ID# | Measured Concentration 25OHD$_3$ (ng/mL) | | | |
|---|---|---|---|---|---|
| | | Serum | SST | EDTA | Na Hep |
| 1 | 5804 | 26.8 | 25.7 | 24.3 | 26.8 |
| 2 | 5207 | 16.1 | 17.6 | 16.1 | 16.5 |
| 3 | 5235 | 17.4 | 17.7 | 16.8 | 17.2 |
| 4 | 5333 | 62.9 | 62.7 | 63.7 | 57.4 |
| 5 | 5336 | 33.0 | 32.4 | 28.8 | 28.8 |
| 6 | 5339 | 17.2 | 17.6 | 17.8 | 17.8 |
| 7 | 5340 | 16.7 | 17.1 | 16.8 | 16.5 |
| 8 | 5342 | 28.6 | 27.9 | 26.9 | 30.5 |
| 9 | 5344 | 23.3 | 23.8 | 22.3 | 22.9 |
| 10 | 5351 | 19.4 | 20.0 | 20.4 | 21.4 |
| 11 | 5355 | 17.6 | 16.7 | 19.4 | 18.3 |
| 12 | 5362 | 25.3 | 25.2 | 23.5 | 24.0 |
| 13 | 5365 | 40.9 | 44.7 | 46.8 | 42.9 |
| 14 | 5406 | 23.1 | 20.3 | 21.5 | 20.5 |
| 15 | 5408 | 31.7 | 33.9 | 31.6 | 32.3 |
| 16 | 5414 | 21.1 | 21.8 | 21.2 | 20.4 |
| 17 | 5422 | 44.0 | 47.7 | 45.5 | 47.3 |
| 18 | 5432 | 13.6 | 14.2 | 12.3 | 13.8 |
| 19 | 5463 | 15.1 | 15.4 | 15.6 | 14.5 |
| 20 | 5493 | 38.6 | 42.2 | 40.1 | 36.8 |
| 21 | 5366 | 47.5 | 48.1 | 46.7 | 45.1 |
| 22 | 5368 | 23.0 | 23.6 | 22.3 | 22.3 |
| 23 | 5392 | 34.1 | 33.4 | 34.4 | 27.6 |
| 24 | 5451 | 36.4 | 42.1 | 40.0 | 38.3 |
| 25 | 5455 | 27.3 | 29.9 | 25.1 | 27.9 |
| 26 | 5476 | 16.7 | 17.9 | 15.8 | 16.6 |
| 27 | 5483 | 30.4 | 28.2 | 26.5 | 28.1 |
| 28 | 5484 | 38.2 | 37.7 | 37.2 | 36.0 |
| 29 | 5537 | 30.5 | 30.3 | 27.2 | 27.0 |
| 30 | 5547 | 9.2 | 9.0 | 8.7 | 8.2 |
| 31 | 5560 | 9.4 | 10.9 | 9.8 | 8.6 |
| 32 | 5571 | 30.9 | 31.7 | 29.6 | 29.2 |
| 33 | 5572 | 47.6 | 50.3 | 47.7 | 48.6 |
| 34 | 5577 | 11.2 | 11.7 | 10.4 | 9.2 |
| 35 | 5606 | 39.3 | 38.8 | 41.0 | 37.7 |
| 36 | 5611 | 21.9 | 25.3 | 20.7 | 21.1 |
| 37 | 5650 | 38.0 | 34.3 | 34.6 | 36.2 |
| 38 | 5651 | 34.8 | 32.8 | 32.4 | 32.4 |
| 39 | 5653 | 29.4 | 32.3 | 28.1 | 27.0 |
| 40 | 5668 | 11.4 | 12.8 | 14.2 | 13.1 |

Example 14

Exemplary Spectra from LDTD-MS/MS Analysis of PTAD Derivatized 25-Hydroxyvitamin D$_7$ and PTAD Derivatized 25-Hydroxyvitamin PTAD derivatives of 25-hydroxyvitamin D$_2$, 25-hydroxyvitamin D$_2$-[6, 19, 19]-$^2$H$_3$, 25-hydroxyvitamin D$_2$-[26, 26, 26, 27, 27, 27]-$^2$H$_6$ 25-hydroxyvitamin D$_3$, 25-hydroxyvitamin D$_3$-[6, 19, 19]-$^2$H$_3$, and 25-hydroxyvitamin D$_3$-[26, 26, 26, 27, 27, 27]-$^2$H$_6$ were prepared as described above. The resulting solutions were analyzed by LDTD-MS/MS. Results of these analyses are presented below.

Figure 6A:
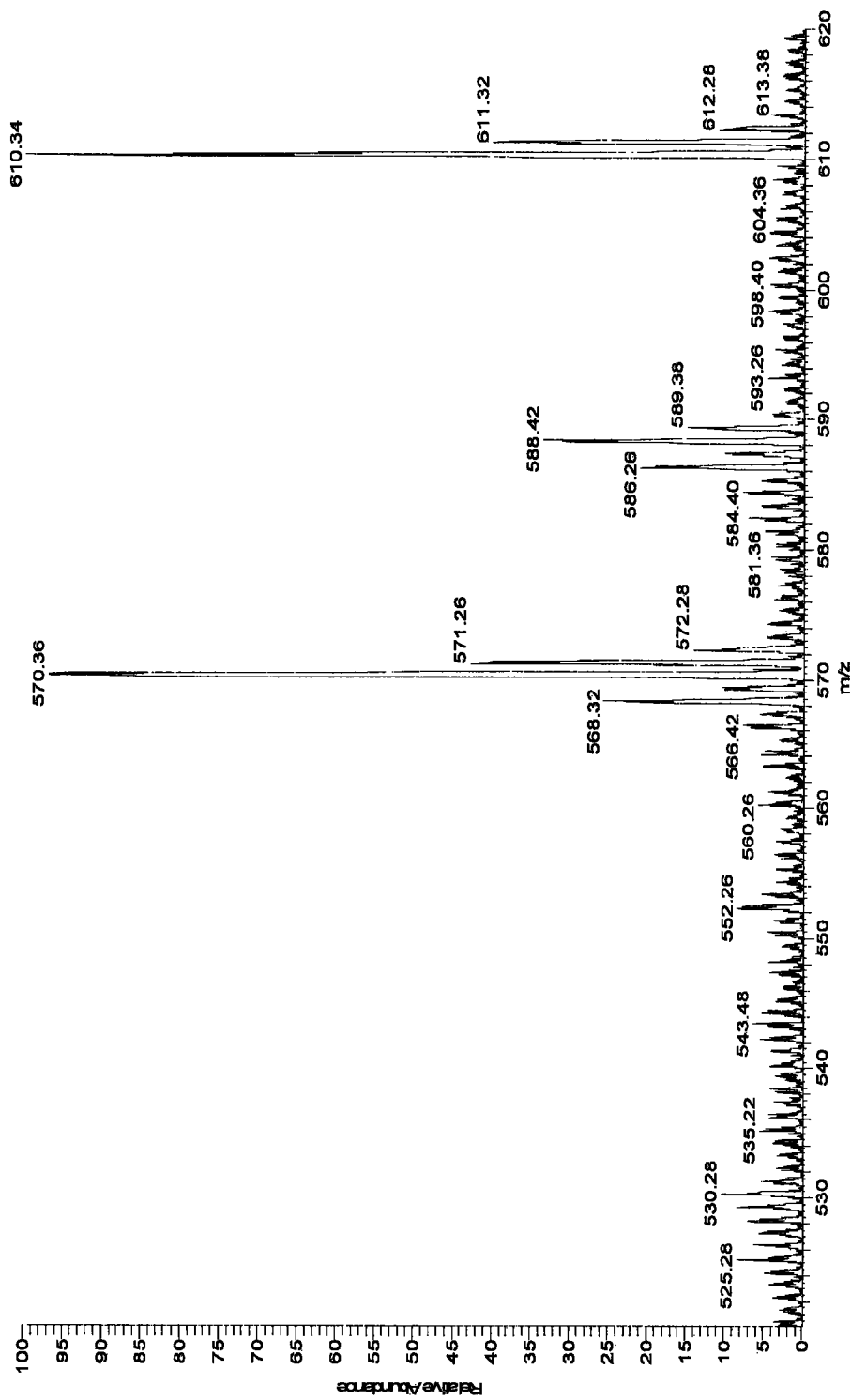
FIG. 6A shows an exemplary Q1 scan spectrum (covering the m/z range of about 520 to 620) for PTAD-25-hydroxyvitamin D$_2$ ions.
Figure 7A:
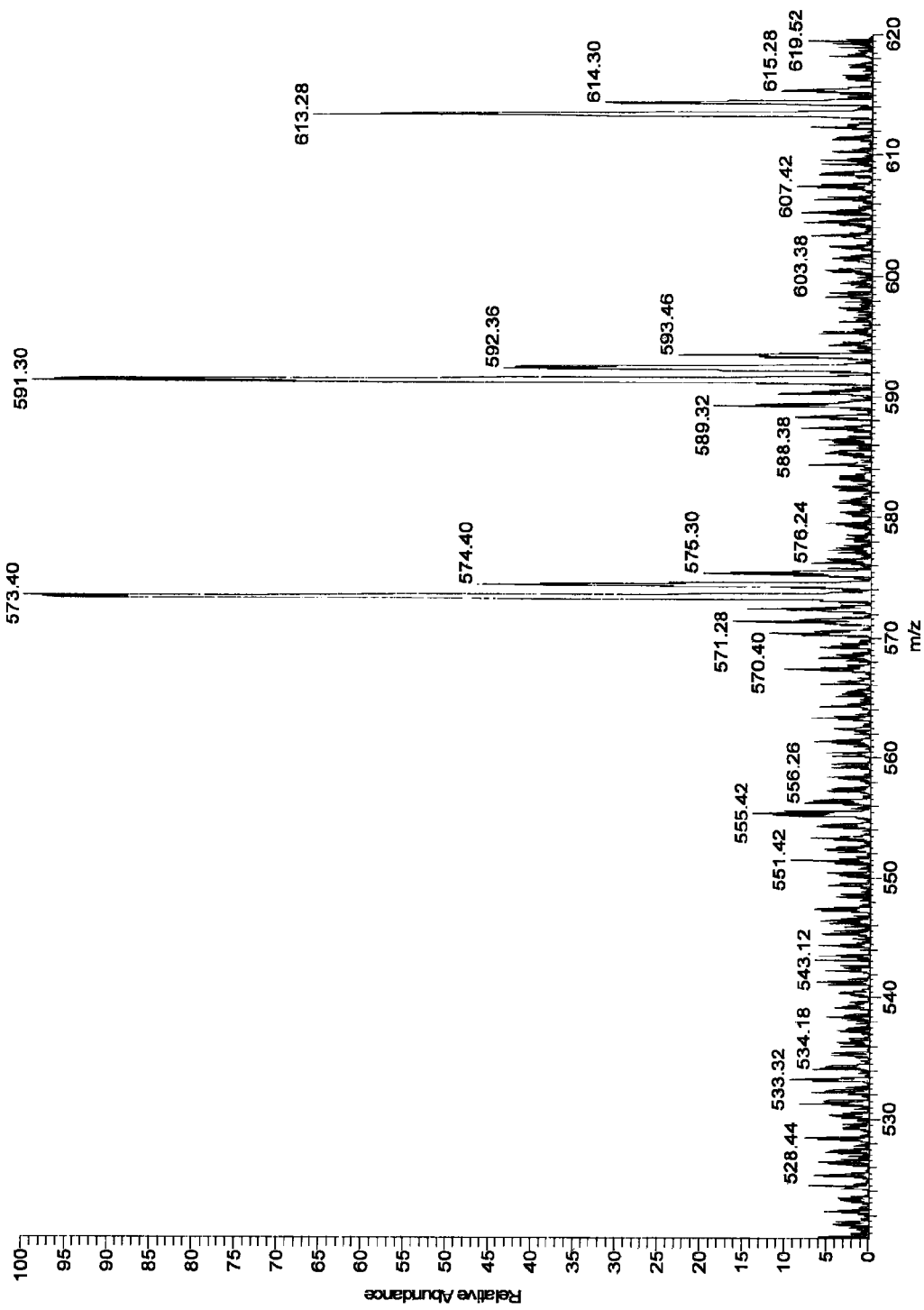
FIG. 7A shows an exemplary Q1 scan spectrum (covering the m/z range of about 520 to 620) for PTAD-25-hydroxyvitamin D$_2$-[6, 19, 19]-$^2H_3$ ions.
Figure 8A:
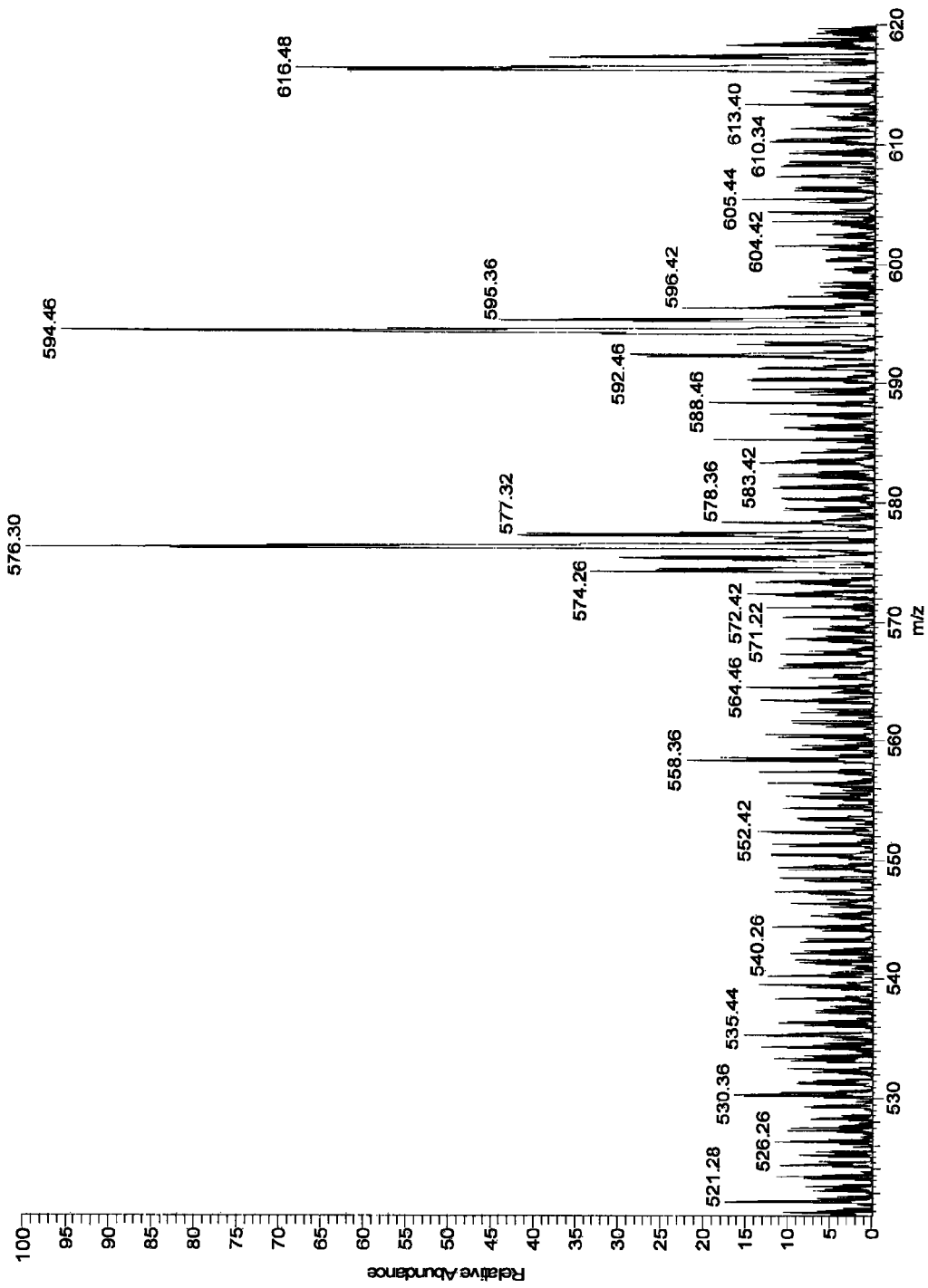
FIG. 8A shows an exemplary Q1 scan spectrum (covering the m/z range of about 520 to 620) for PTAD-25-hydroxyvitamin D$_2$-[26, 26, 26, 27, 27, 27]-$^2H_6$ ions.

Exemplary Q1 scan spectra from the analysis of samples containing PTAD-25-hydroxyvitamin D$_2$, PTAD-25-hydroxyvitamin D$_2$-[6, 19, 19]-$^2$H$_3$, and PTAD-25-hydroxyvitamin D$_2$-[26, 26, 26, 27, 27, 27]-$^2$H$_6$ are shown in FIGS. 6A, 7A, and 8A, respectively. These spectra were collected by scanning Q1 across a m/z range of about 520 to 620.

Figure 6B:
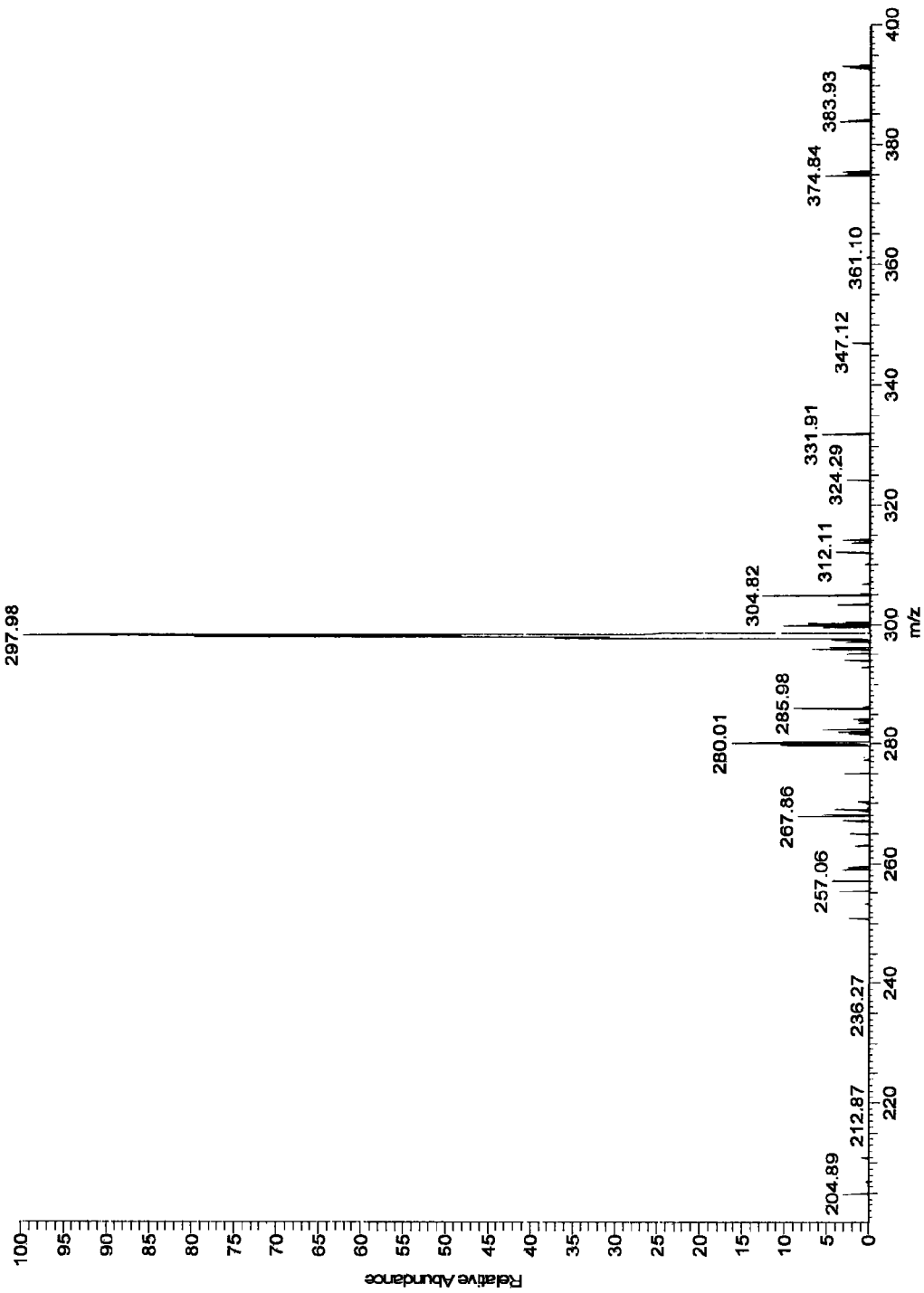
FIG. 6B shows an exemplary product ion spectra (covering the m/z range of about 200 to 400) for fragmentation of the PTAD-25-hydroxyvitamin D$_2$ precursor ion with m/z of about 570.3. Details are described in Example 14.

Exemplary product ion scans from each of these species are presented in FIGS. 6B, 7B, and 8B, respectively. The precursor ions selected in Q1, and collision energies used in fragmenting the precursors are indicated in Table 13.

A preferred MRM transition for the quantitation of PTAD-25-hydroxyvitamin D$_2$ is fragmenting a precursor ion with a m/z of about 570.3 to a product ion with a m/z of about 298.1. A preferred MRM transition for the quantitation of PTAD-25-hydroxyvitamin $D_2$-[6, 19, 19]-$^2H_3$ is fragmenting a precursor ion with a m/z of about 573.3 to a product ion with a m/z of about 301.1. A preferred MRM transition for the quantitation of PTAD-25-hydroxyvitamin $D_2$-[26, 26, 26, 27, 27, 27]-$^2H_6$ is fragmenting a precursor ion with a m/z of about 576.3 to a product ion with a m/z of about 298.1. However, as can be seen in the product ion scans in FIGS. 6B, 7B, and 8B, additional product ions may be selected to replace or augment the preferred fragment ion.

TABLE 13

Precursor Ions and Collision Cell Energies for Fragmentation of PTAD-25-hydroxyvitamin $D_2$, PTAD-25-hydroxyvitamin $D_2$-[6,19,19]-$^2H_3$, and PTAD-25-hydroxyvitamin $D_2$-[26,26,26,27,27,27]-$^2H_6$

| Analyte | Precursor Ion (m/z) | Collision Cell Energy (V) |
|---|---|---|
| PTAD-25-hydroxyvitamin $D_2$ | 570.3 | 15 |
| PTAD-25-hydroxyvitamin $D_2$-[6,19,19]-$^2H_3$ | 573.3 | 15 |
| PTAD-25-hydroxyvitamin $D_2$-[26,26,26,27,27,27]-$^2H_6$ | 576.3 | 15 |

Figure 9A:
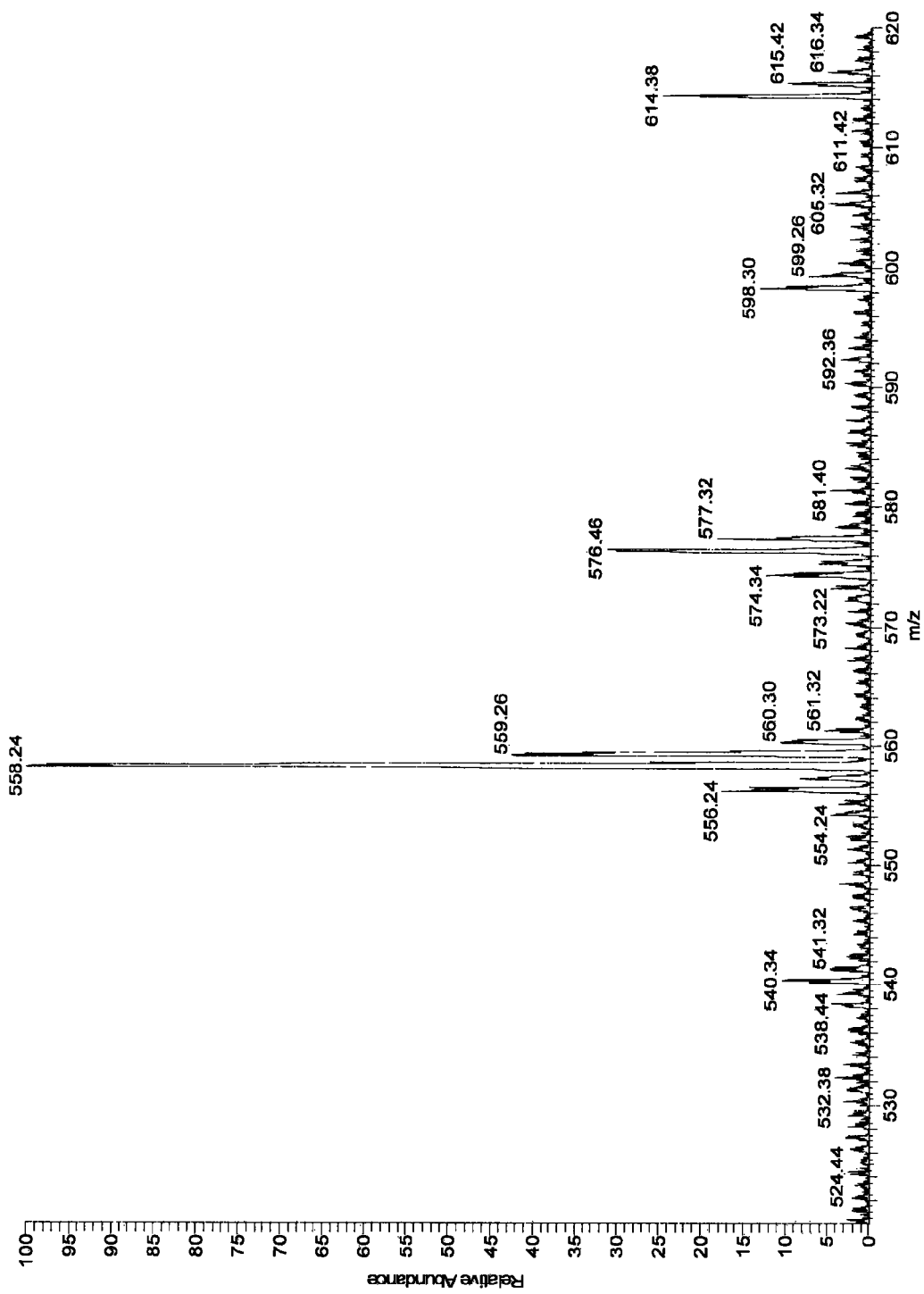
FIG. 9A shows an exemplary Q1 scan spectrum (covering the m/z range of about 520 to 620) for PTAD-25-hydroxyvitamin D$_3$ ions.
Figure 10A:
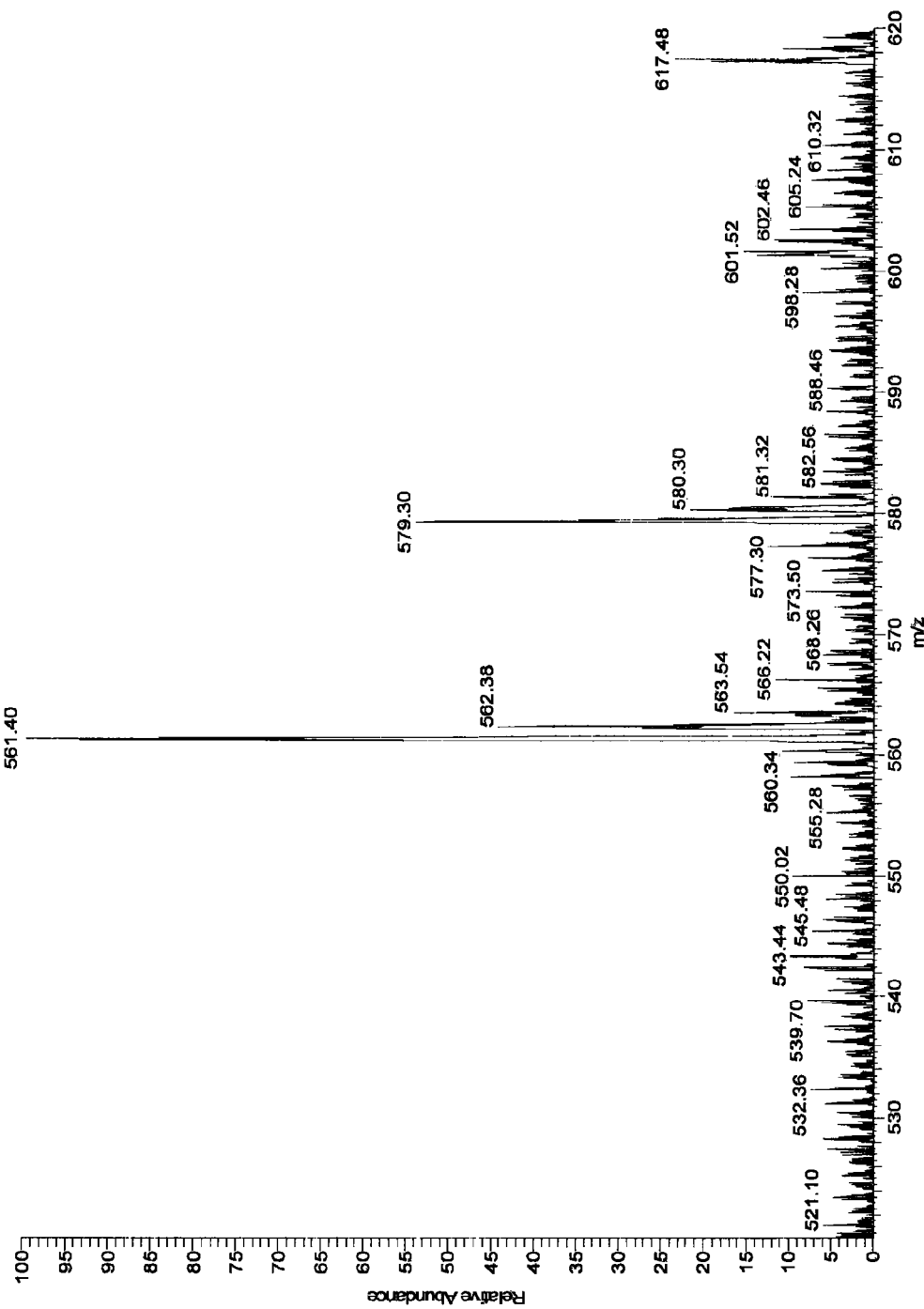
FIG. 10A shows an exemplary Q1 scan spectrum (covering the m/z range of about 520 to 620) for PTAD-25-hydroxyvitamin D$_3$-[6, 19, 19]-$^2H_3$ ions.
Figure 11A:
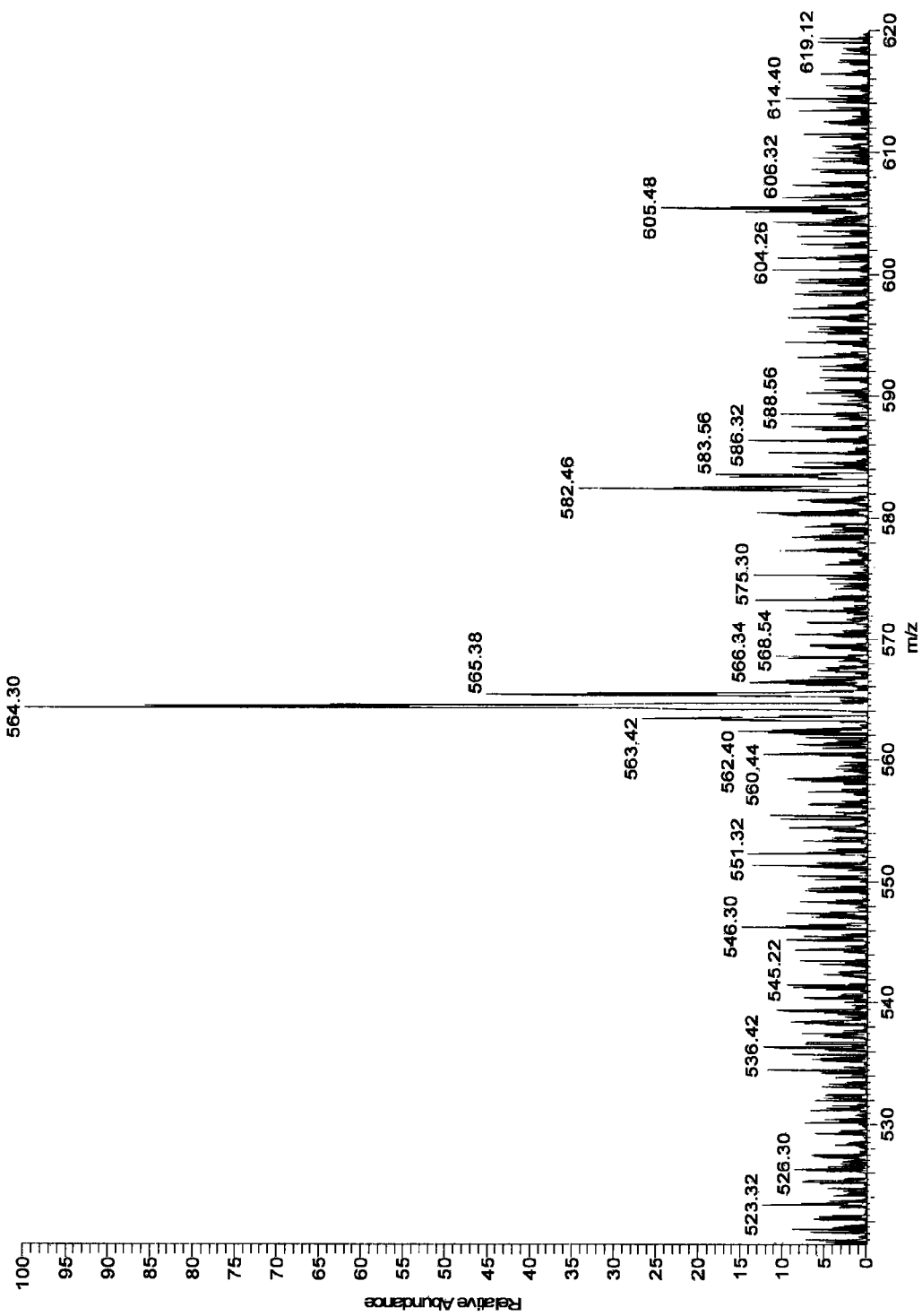
FIG. 11A shows an exemplary Q1 scan spectrum (covering the m/z range of about 520 to 620) for PTAD-25-hydroxyvitamin D$_3$-[26, 26, 26, 27, 27, 27]-$^2H_6$ ions.

Exemplary Q1 scan spectra from the analysis of PTAD-25-hydroxyvitamin $D_3$, PTAD-25-hydroxyvitamin $D_3$-[6, 19, 19]-$^2H_3$, and PTAD-25-hydroxyvitamin $D_3$-[26, 26, 26, 27, 27, 27]-$^2H_6$ are shown in FIGS. 9A, 10A, and 11A, respectively. These spectra were collected by scanning Q1 across a m/z range of about 520 to 620.

Figure 9B:
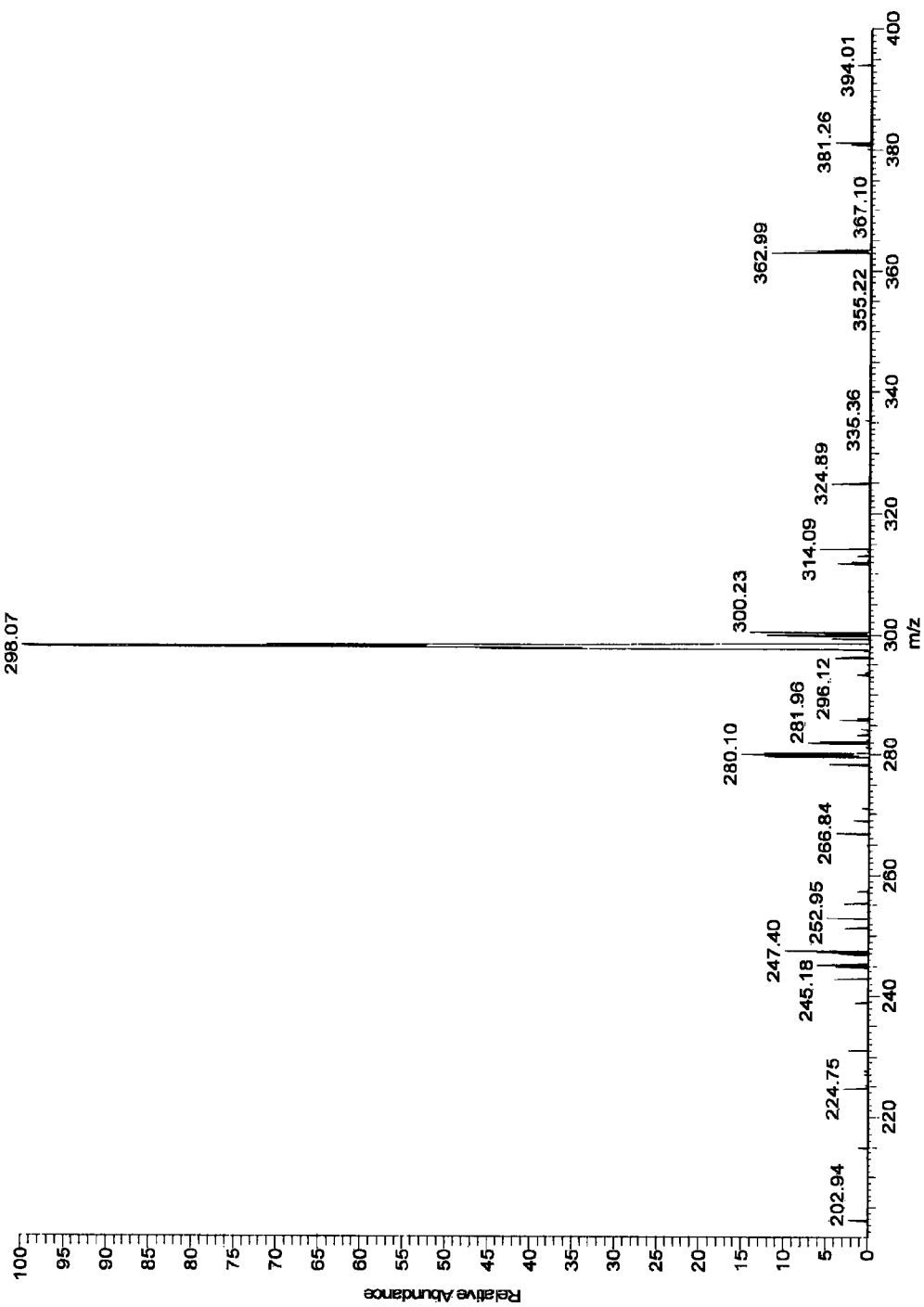
FIG. 9B shows an exemplary product ion spectra (covering the m/z range of about 200 to 400) for fragmentation of the PTAD-25-hydroxyvitamin D$_3$ precursor ion with m/z of about 558.3. Details are described in Example 14.
Figure 10B:
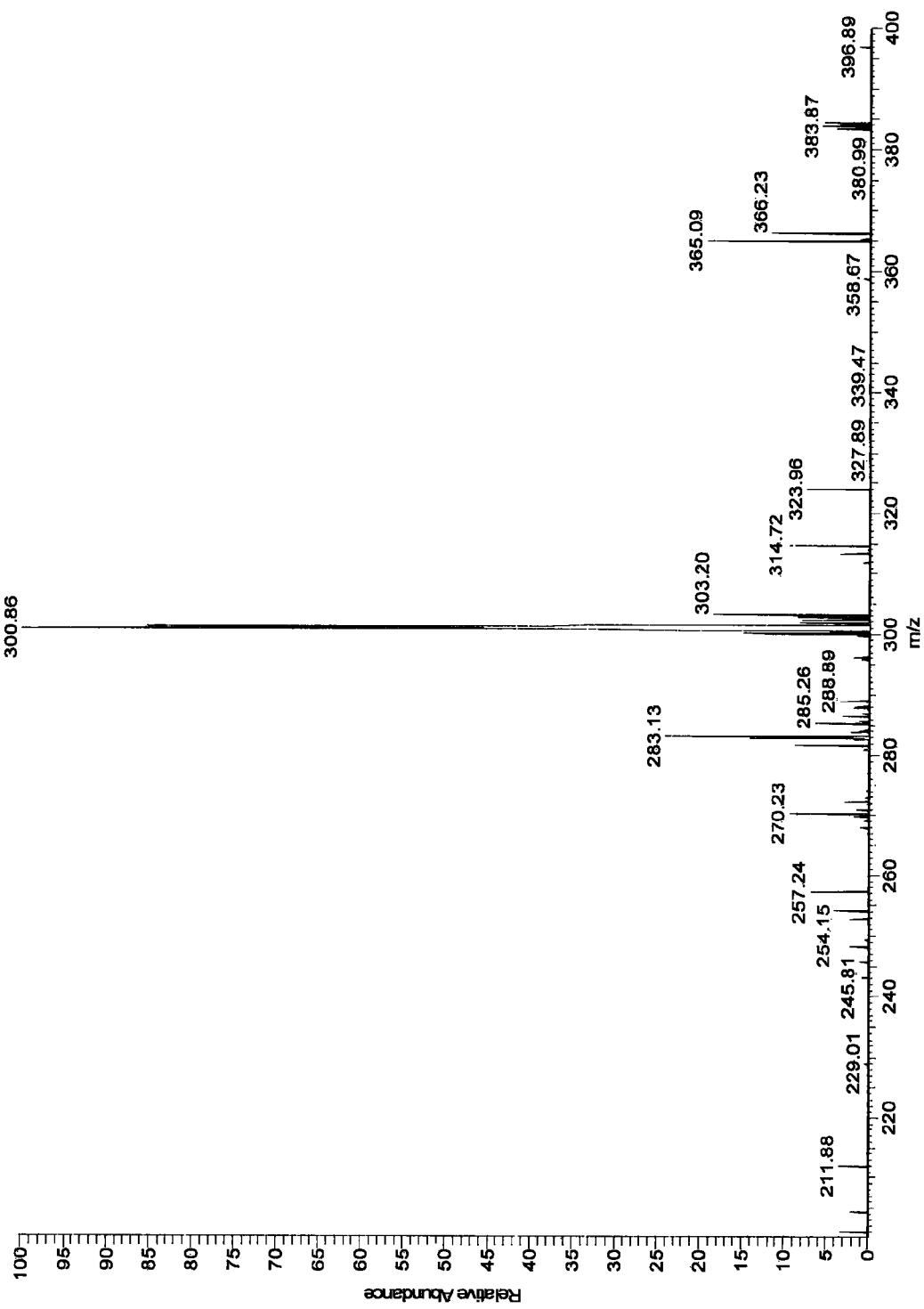
FIG. 10B shows an exemplary product ion spectra (covering the m/z range of about 200 to 400) for fragmentation of the PTAD-25-hydroxyvitamin D$_3$-[6, 19, 19]-$^2H_3$ precursor ion with m/z of about 561.3. Details are described in Example 14.
Figure 11B:
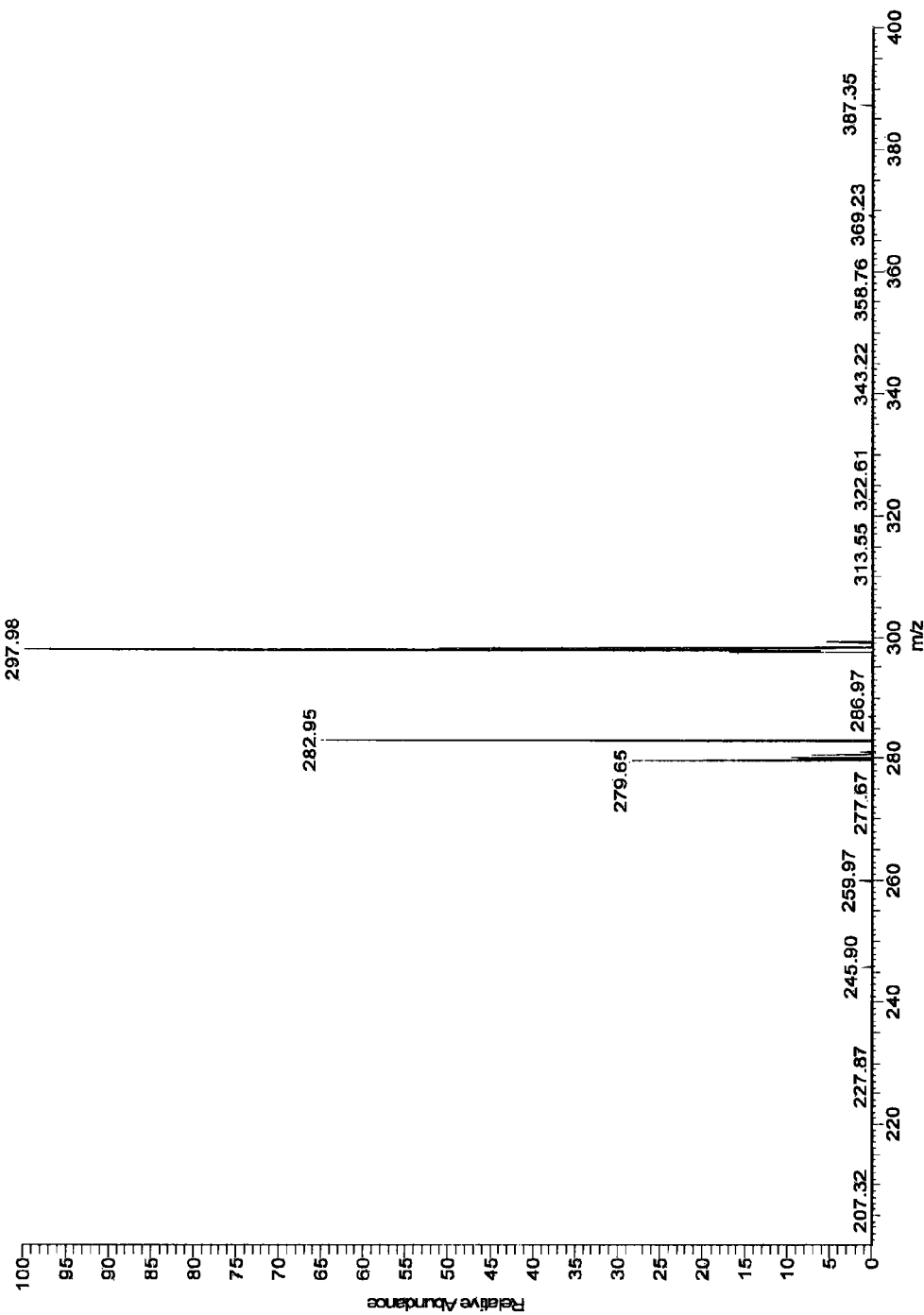
FIG. 11B shows an exemplary product ion spectra (covering the m/z range of about 200 to 400) for fragmentation of the PTAD-25-hydroxyvitamin D$_3$-[26, 26, 26, 27, 27, 27]-$^2H_6$ precursor ion with m/z of about 564.3. Details are described in Example 14.

Exemplary product ion scans from each of these species are presented in FIGS. 9B, 10B, and 11B, respectively. The precursor ions selected in Q1 and the collision energies used to generate these product ion spectra are indicated in Table 14.

A preferred MRM transition for the quantitation of PTAD-25-hydroxyvitamin $D_3$ is fragmenting a precursor ion with a m/z of about 558.3 to a product ion with a m/z of about 298.1. A preferred MRM transition for the quantitation of PTAD-25-hydroxyvitamin $D_3$-[6, 19, 19]-$^2H_3$ is fragmenting a precursor ion with a m/z of about 561.3 to a product ion with a m/z of about 301.1. A preferred MRM transition for the quantitation of PTAD-25-hydroxyvitamin $D_3$-[26, 26, 26, 27, 27, 27]-$^2H_6$ is fragmenting a precursor ion with a m/z of about 564.3 to a product ion with a m/z of about 298.1. However, as can be seen in the product ion scans in FIGS. 9B, 10B, and 11B, additional product ions may be selected to replace or augment the preferred fragment ion.

TABLE 14

Precursor Ions and Collision Cell Energies for Fragmentation of PTAD-25-hydroxyvitamin $D_3$, PTAD-25-hydroxyvitamin $D_3$-[6,19,19]-$^2H_3$, and PTAD-25-hydroxyvitamin $D_3$-[26,26,26,27,27,27]-$^2H_6$

| Analyte | Precursor Ion (m/z) | Collision Cell Energy (V) |
|---|---|---|
| PTAD-25-hydroxyvitamin $D_3$ | 558.3 | 15 |
| PTAD-25-hydroxyvitamin $D_3$-[6,19,19]-$^2H_3$ | 561.3 | 15 |
| PTAD-25-hydroxyvitamin $D_3$-[26,26,26,27,27,27]-$^2H_6$ | 564.3 | 15 |

Example 15

Exemplary Spectra from LDTD-MS/MS Analysis of PTAD Derivatized 1α,25-Dihydroxyvitamin $D_2$ and 1α,25-Dihydroxyvitamin $D_3$ PTAD derivatives of 1α,25-dihydroxyvitamin $D_2$, 1α,25-dihydroxyvitamin $D_2$-[26, 26, 26, 27, 27, 27]-$^2H_6$, 1α,25-dihydroxyvitamin $D_3$, 1α,25-dihydroxyvitamin $D_3$-[6, 19, 19]-$^2H_3$, and 1α,25-dihydroxyvitamin $D_3$-[26, 26, 26, 27, 27, 27]-$^2H_6$ were prepared by treating aliquots of stock solutions of each analyte with PTAD in acetonitrile. The derivatization reactions was allowed to proceed for approximately one hour, and were quenched by adding water to the reaction mixture. The derivatized analytes were then analyzed according to the procedure outlined above in Example 1.

Figure 12A:
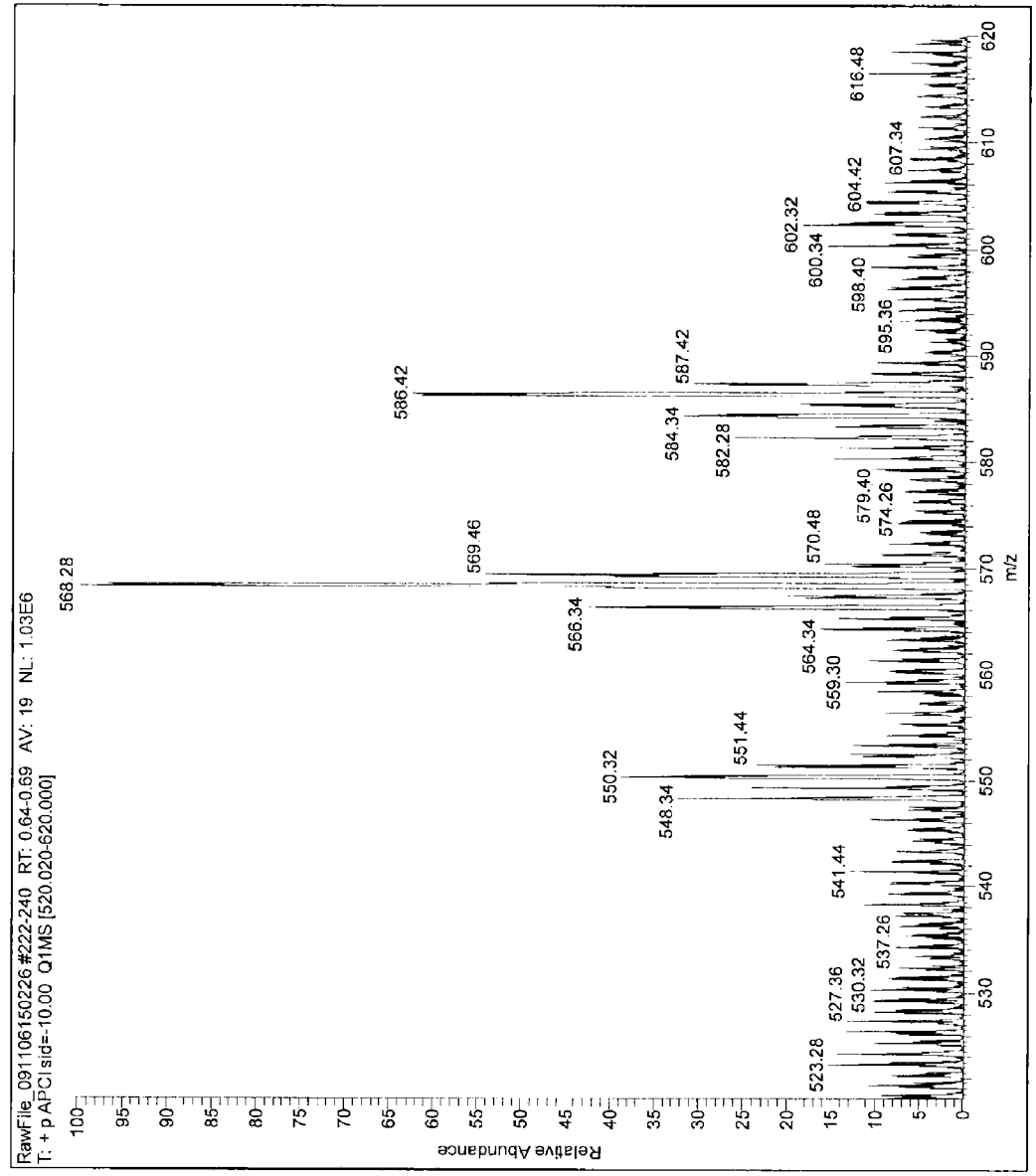
FIG. 12A shows an exemplary Q1 scan spectrum (covering the m/z range of about 520 to 620) for PTAD-1α,25-dihydroxyvitamin D$_2$ ions.
Figure 12B:
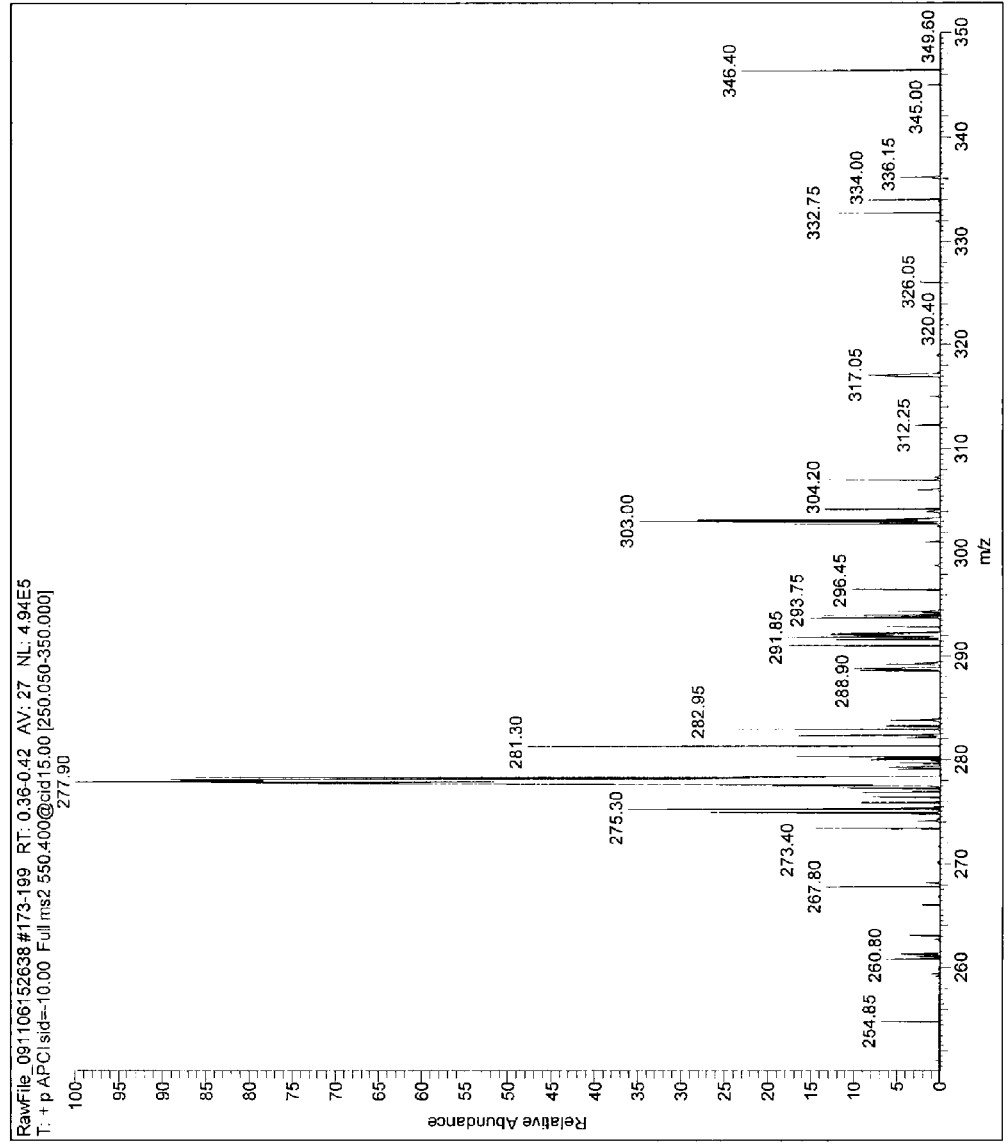
FIG. 12B shows an exemplary product ion spectra (covering the m/z range of about 250 to 350) for fragmentation of the PTAD-1α,25-dihydroxyvitamin D$_2$ precursor ion with m/z of about 550.4.
Figure 12C:
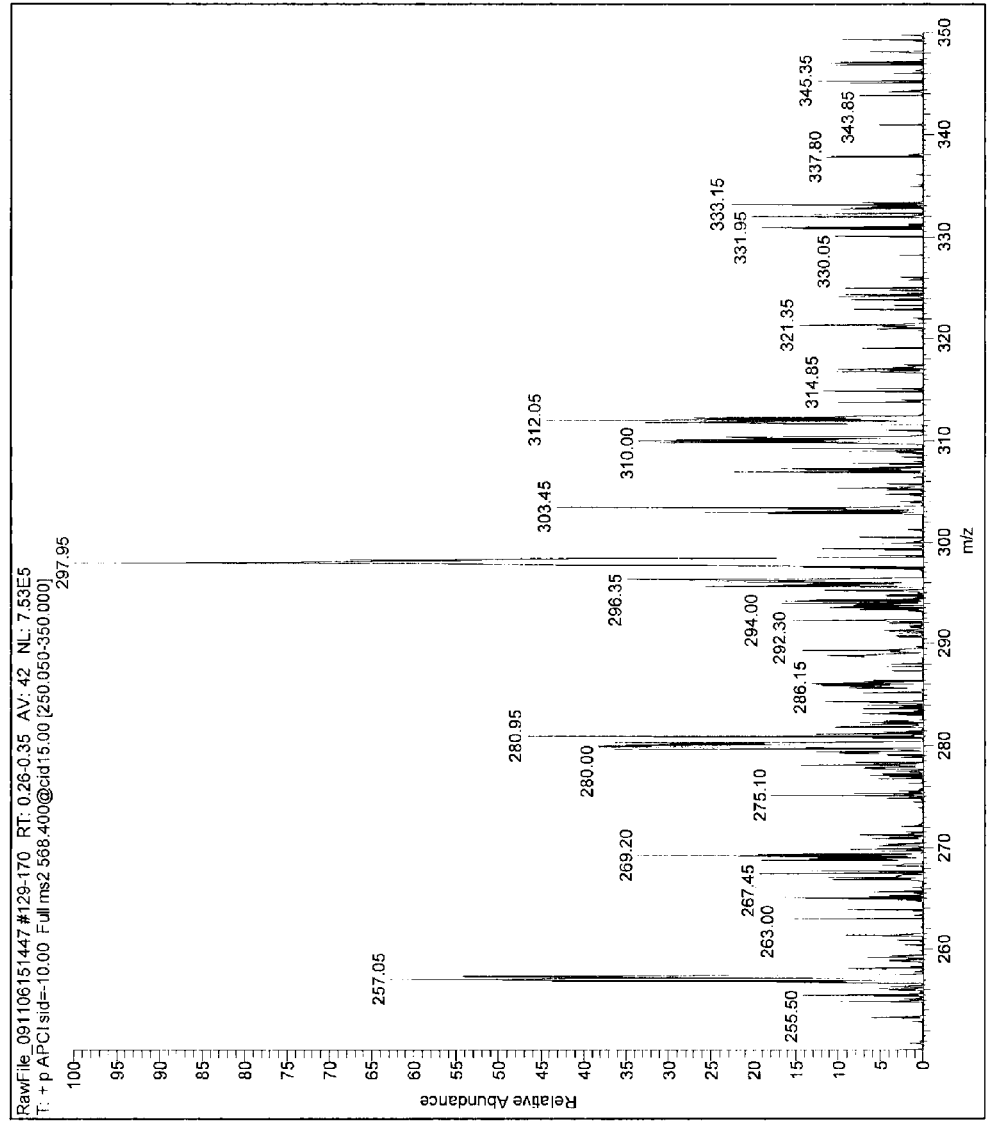
FIG. 12C shows an exemplary product ion spectra (covering the m/z range of about 250 to 350) for fragmentation of the PTAD-1α,25-dihydroxyvitamin D$_2$ precursor ion with m/z of about 568.4.
Figure 12D:
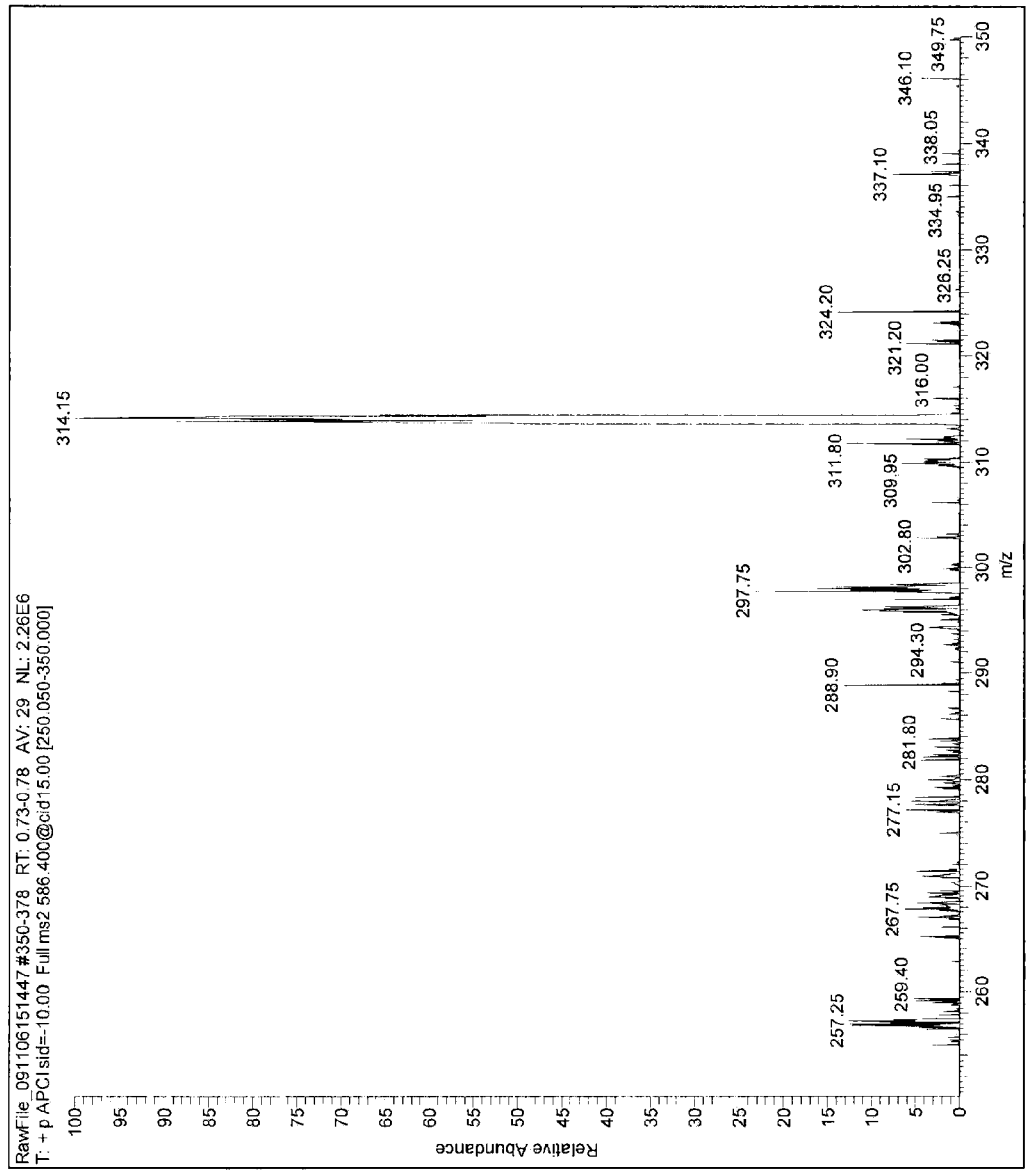
FIG. 12D shows an exemplary product ion spectra (covering the m/z range of about 250 to 350) for fragmentation of the PTAD-1α,25-dihydroxyvitamin D$_2$ precursor ion with m/z of about 586.4. Details are described in Example 15.
Figure 13A:
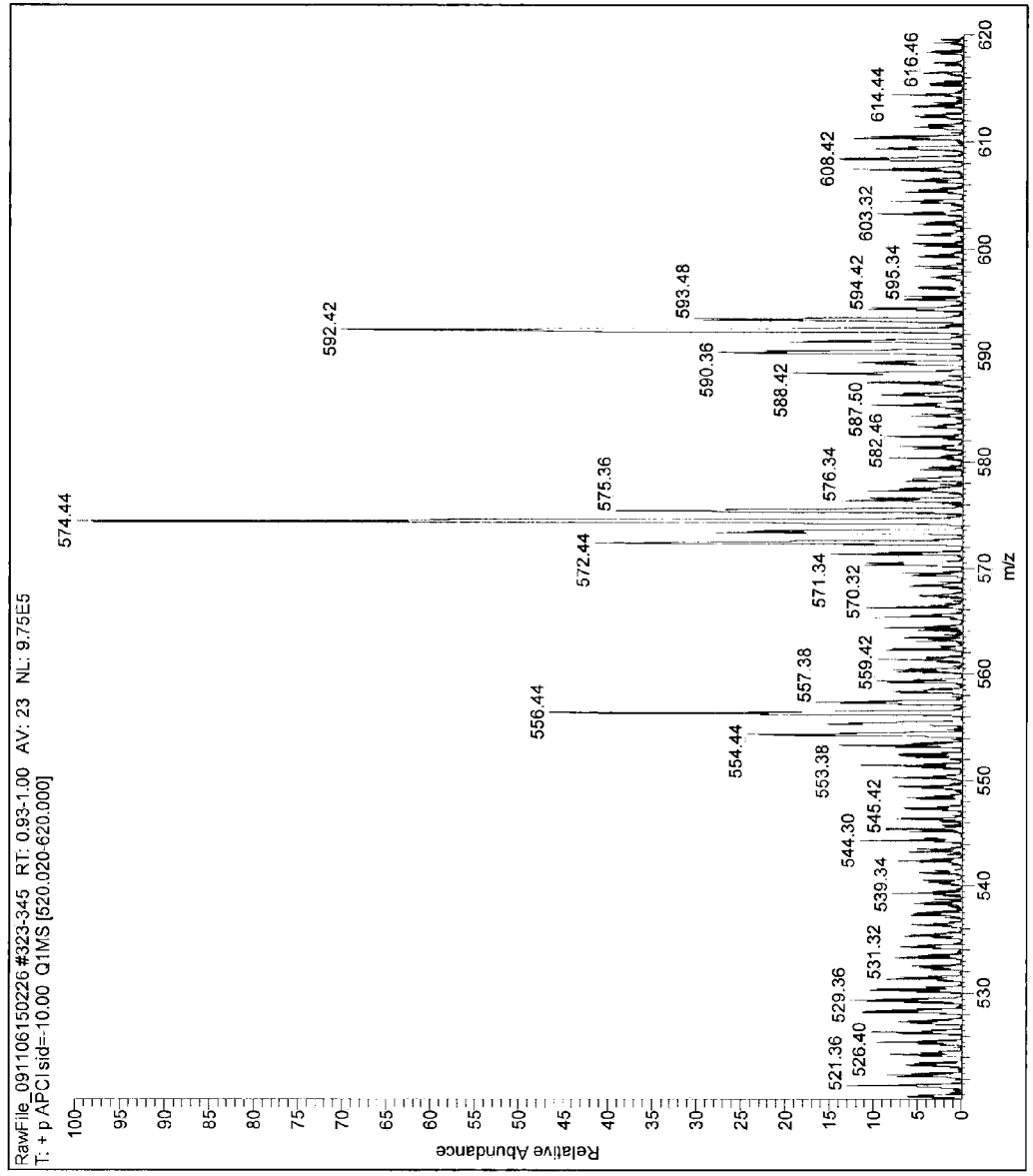
FIG. 13A shows an exemplary Q1 scan spectrum (covering the m/z range of about 520 to 620) for PTAD-1α,25-dihydroxyvitamin D$_2$-[26, 26, 26, 27, 27, 27]-$^2H_6$ ions.
Figure 13B:
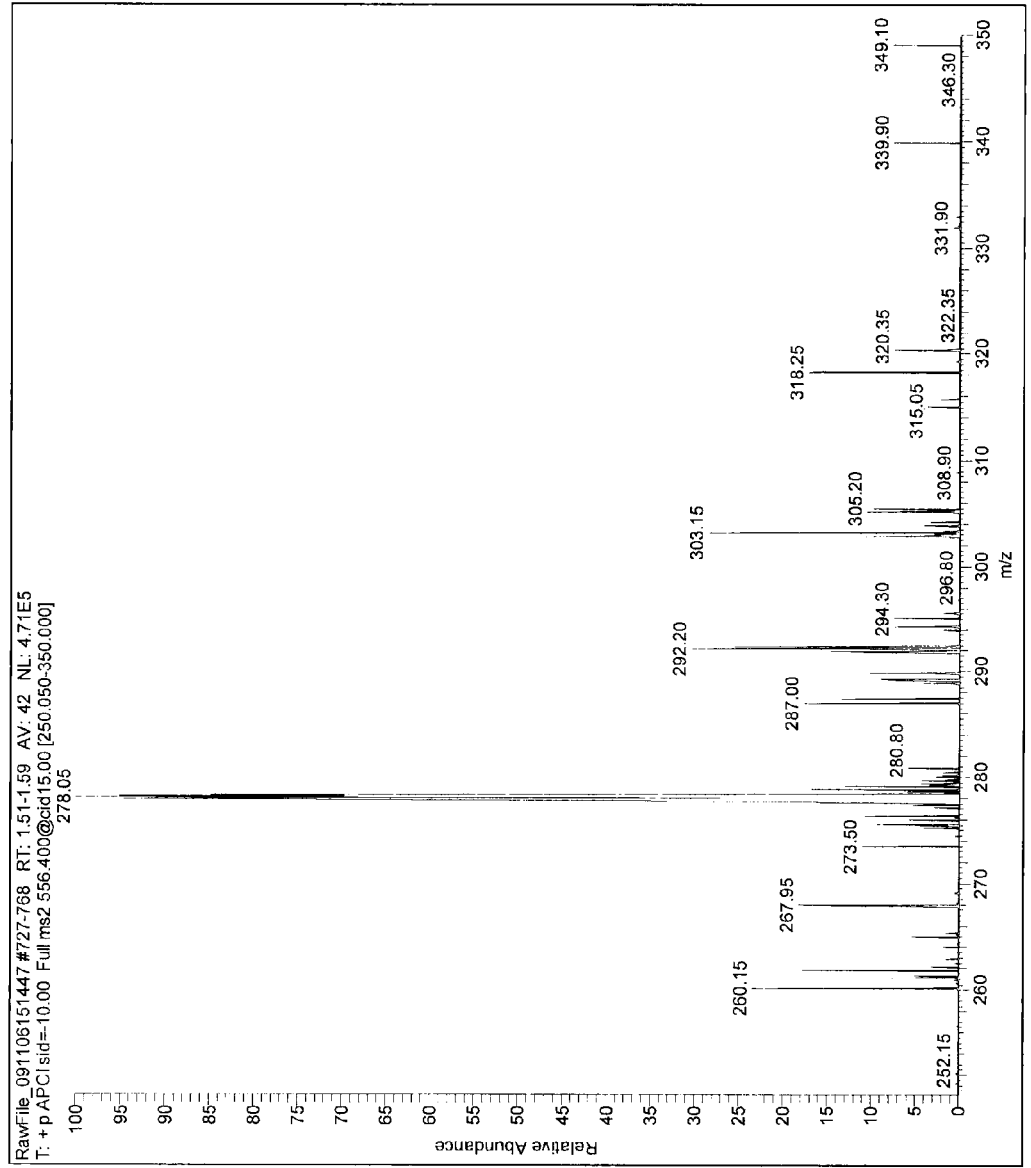
FIG. 13B shows an exemplary product ion spectra (covering the m/z range of about 250 to 350) for fragmentation of the PTAD-1α,25-dihydroxyvitamin D$_2$-[26, 26, 26, 27, 27, 27]-$^2H_6$ precursor ion with m/z of about 556.4.
Figure 13C:
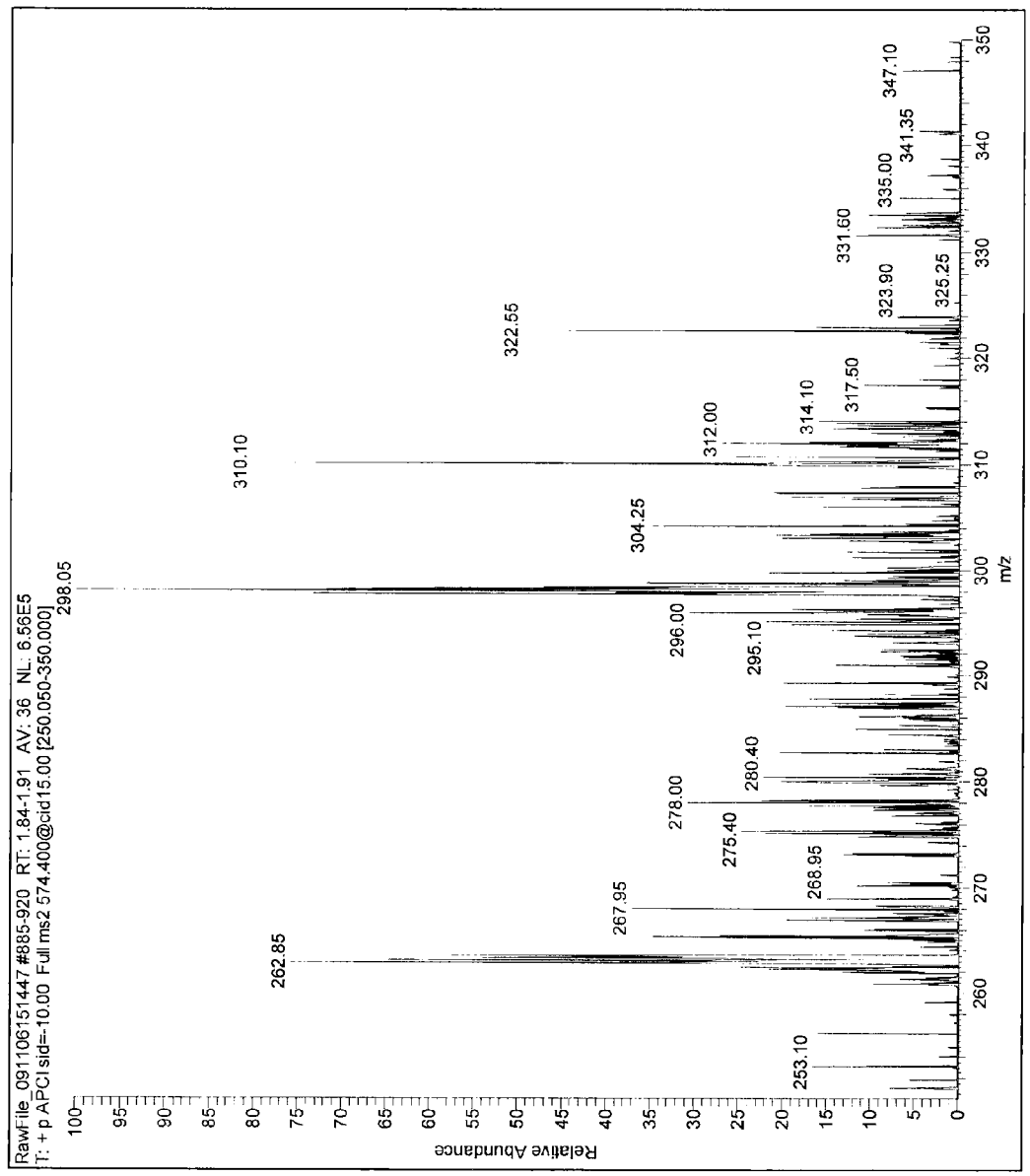
FIG. 13C shows an exemplary product ion spectra (covering the m/z range of about 250 to 350) for fragmentation of the PTAD-1α,25-dihydroxyvitamin D$_2$-[26, 26, 26, 27, 27, 27]-$^2H_6$ precursor ion with m/z of about 574.4
Figure 13D:
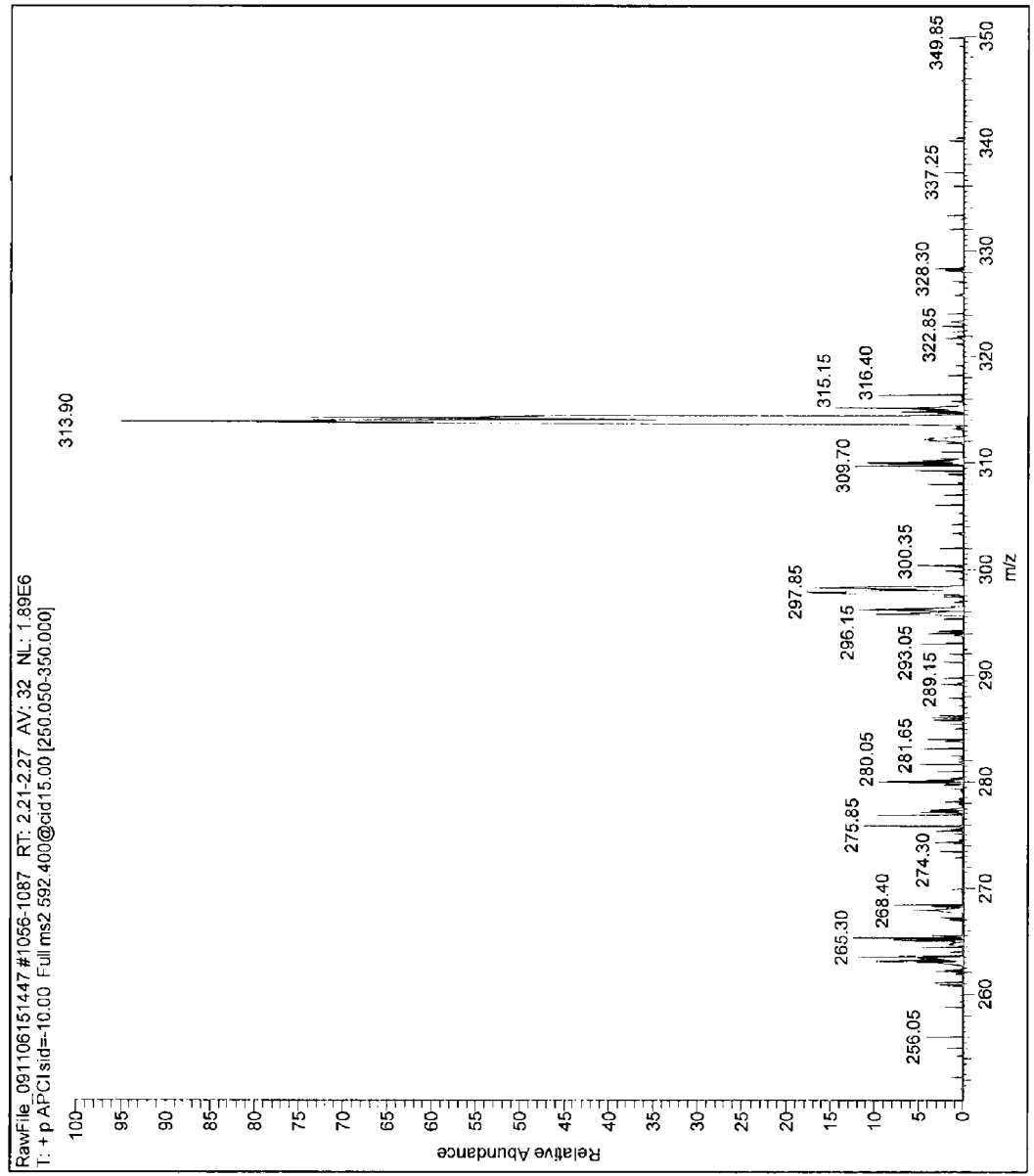
FIG. 13D shows an exemplary product ion spectra (covering the m/z range of about 250 to 350) for fragmentation of the PTAD-1α,25- dihydroxyvitamin D$_2$-[26, 26, 26, 27, 27, 27]-$^2$H$_6$ precursor ion with m/z of about 592.4. Details are described in Example 15.

Exemplary Q1 scan spectra from the analysis of samples containing PTAD-1α,25-dihydroxyvitamin $D_2$ and PTAD-1α,25-dihydroxyvitamin $D_2$-[26, 26, 26, 27, 27, 27]-$^2H_6$ are shown in FIGS. 12A, and 13A, respectively. These spectra were collected by scanning Q1 across a m/z range of about 520 to 620.

Exemplary product ion scans generated from three different precursor ions for each of PTAD-1α,25-dihydroxyvitamin $D_2$ and PTAD-1α,25-dihydroxyvitamin $D_2$-[26, 26, 26, 27, 27, 27]-$^2H_6$ are presented in FIGS. 12B-D, and 13B-D, respectively. The precursor ions selected in Q1 and the collision energies used to generate these product ion spectra are indicated in Table 15.

Exemplary MRM transitions for the quantitation of PTAD-1α,25-dihydroxyvitamin $D_2$ include fragmenting a precursor ion with a m/z of about 550.4 to a product ion with a m/z of about 277.9; fragmenting a precursor ion with a m/z of about 568.4 to a product ion with a m/z of about 298.0; and fragmenting a precursor ion with a m/z of about 586.4 to a product ion with a m/z of about 314.2. Exemplary MRM transitions for the quantitation of PTAD-1α,25-dihydroxyvitamin $D_2$-[26, 26, 26, 27, 27, 27]-$^2H_6$ include fragmenting a precursor ion with a m/z of about 556.4 to a product ion with a m/z of about 278.1; fragmenting a precursor ion with a m/z of about 574.4 to a product ion with a m/z of about 298.1; and fragmenting a precursor ion with a m/z of about 592.4 to a product ion with a m/z of about 313.9. However, as can be seen in the product ion scans in FIGS. 12B-D and 13B-D, several other product ions are generated upon fragmentation of the precursor ions. Additional product ions may be selected from those indicated in FIGS. 12B-D and 13B-D to replace or augment the exemplary fragment ions.

TABLE 15

Precursor Ions and Collision Cell Energies for Fragmentation of PTAD-1α,25-dihydroxyvitamin $D_2$ and PTAD-1α,25-dihydroxyvitamin $D_2$-[26,26,26,27,27,27]-$^2H_6$

| Analyte | Precursor Ion (m/z) | Collision Cell Energy (V) |
|---|---|---|
| PTAD-1α,25-dihydroxyvitamin $D_2$ | 550.4, 568.4, 586.4 | 15 |
| PTAD-1α,25-dihydroxyvitamin $D_2$-[26,26,26,27,27,27]-$^2H_6$ | 556.3, 574.4, 592.4 | 15 |

Exemplary Q1 scan spectra from the analysis of PTAD-1α,25-hydroxyvitamin $D_3$, PTAD-1α,25-dihydroxyvitamin $D_3$-[6, 19, 19]-$^2H_3$, and PTAD-1α,25-dihydroxyvitamin $D_3$-[26, 26, 26, 27, 27, 27]-$^2H_6$ are shown in FIGS. 14A, 15A, and 16A, respectively. These spectra were collected by scanning Q1 across a m/z range of about 520 to 620.

Exemplary product ion scans generated from three different precursor ions for each of PTAD-1α,25-hydroxyvitamin $D_3$, PTAD-1α,25-dihydroxyvitamin $D_3$-[6, 19, 19]-$^2H_3$, and PTAD-1α,25-dihydroxyvitamin $D_3$-[26, 26, 26, 27, 27, 27]-$^2H_6$ are presented in FIGS. 14B-D, 15A-D, and 16B-D, respectively. The precursor ions selected in Q1 and the collision energies used to generate these product ion spectra are indicated in Table 16.

Exemplary MRM transitions for the quantitation of PTAD-1α,25-hydroxyvitamin $D_3$ include fragmenting a precursor ion with a m/z of about 538.4 to a product ion with a m/z of about 278.1; fragmenting a precursor ion with a m/z of about 556.4 to a product ion with a m/z of about 298.0; and fragmenting a precursor ion with a m/z of about 574.4 to a product ion with a m/z of about 313.0. Exemplary MRM transitions for the quantitation of PTAD-1α,25-dihydroxyvitamin $D_3$-[6, 19, 19]-$^2H_3$ include fragmenting a precursor ion with a m/z of about 541.4 to a product ion with a m/z of about 280.9; fragmenting a precursor ion with a m/z of about 559.4 to a product ion with a m/z of about 301.1; and fragmenting a precursor ion with a m/z of about 577.4 to a product ion with a m/z of about 317.3. Exemplary MRM transitions for the quantitation of PTAD-1α,25-dihydroxyvitamin $D_2$-[26, 26, 26, 27, 27, 27]-$^2H_6$ include fragmenting a precursor ion with a m/z of about 544.4 to a product ion with a m/z of about 278.0; fragmenting a precursor ion with a m/z of about 562.4 to a product ion with a m/z of about 298.2; and fragmenting a precursor ion with a m/z of about 580.4 to a product ion with a m/z of about 314.0. However, as can be seen in the product ion scans in FIGS. 14B-D, 15B-D, and 25B-D, several other product ions are generated upon fragmentation of the precursor ions. Additional product ions may be selected from those indicated in FIGS. 14B-D, 15B-D, and 16B-D to replace or augment the exemplary fragment ions.

TABLE 16

Precursor Ions and Collision Cell Energies for Fragmentation of PTAD-1α,25-dihydroxyvitamin $D_3$, PTAD-1α,25-dihydroxyvitamin $D_3$-[6,19,19]-$^2H_3$, and PTAD-1α,25-dihydroxyvitamin $D_3$-[26,26,26,27,27,27]-$^2H_6$

| Analyte | Precursor Ion (m/z) | Collision Cell Energy (V) |
|---|---|---|
| PTAD-1α,25-dihydroxyvitamin $D_3$ | 538.4, 556.4, 574.4 | 15 |
| PTAD-1α,25-dihydroxyvitamin $D_3$-[6,19,19]-$^2H_3$ | 541.4, 559.4, 577.4 | 15 |
| PTAD-1α,25-dihydroxyvitamin $D_3$-[26,26,26,27,27,27]-$^2H_6$ | 544.4, 562.4, 580.4 | 15 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining the amount of one or more vitamin D metabolites in a biological sample when taken from a human, by mass spectrometry, the method comprising the steps of:
    (i) processing a biological sample from a human by one or more methods to generate a processed sample, wherein at least one method used is subjecting said sample to 4-phenyl-1,2,4-triazoline-3,5-dione (PTAD) to generate PTAD-derivatized vitamin D metabolites in the processed sample;
    (ii) subjecting PTAD-derivatized vitamin D metabolites in the processed sample of step (i) to an extraction column under conditions whereby PTAD-derivatized vitamin D metabolites are retained by said extraction column;
    (iii) treating the extraction column with a mobile phase under conditions whereby the retained PTAD-derivatized vitamin D metabolites are eluted from said extraction column;
    (iv) subjecting the eluted PTAD-derivatized vitamin D metabolites from step (iii) to an analytical column under conditions whereby the PTAD-derivatized vitamin D metabolites are eluted from said analytical column;
    (v) subjecting eluted PTAD-derivatized vitamin D metabolites from step (iv) to an ionization source to generate one or more PTAD-derivatized vitamin D metabolite ions detectable by mass spectrometry;
    (vi) determining the amount of one or more of the PTAD-derivatized vitamin D metabolite ions by mass spectrometry; and
    (vii) relating the amount of PTAD-derivatized vitamin D metabolite ions determined in step (vi) to the amount of a vitamin D metabolite in the sample.

2. The method of claim 1, wherein the extraction column of step (ii) is a solid-phase extraction (SPE) column.

3. The method of claim 1, wherein the analytical column of step (iv) is a high performance liquid chromatography (HPLC) column.

4. The method of claim 1, wherein said mass spectrometry is tandem mass spectrometry.

5. The method of claim 4, wherein said tandem mass spectrometry is conducted as multiple reaction monitoring, precursor ion scanning, or product ion scanning.

6. The method of claim 1, wherein said one or more PTAD-derivatized vitamin D metabolites comprises PTAD-derivatized 25-hydroxyvitamin $D_2$ (PTAD-25OHD$_2$).

7. The method of claim 6, wherein said one or more PTAD-derivatized vitamin D metabolite ions comprise ions selected from the group consisting of PTAD-25OHD$_2$ ions with a mass/charge ratio (m/z) of 570.3±0.5 and 298.1±0.5.

8. The method of claim 6, wherein said one or more PTAD-derivatized vitamin D metabolite ions comprise a PTAD-25OHD$_2$ parent ion with a mass/charge ratio (m/z) of 570.3±0.5 and a PTAD-25OHD$_2$ fragment ion with a mass/charge ratio (m/z) of 298.1±0.5.

9. The method of claim 1, wherein said one or more PTAD-derivatized vitamin D metabolites comprises PTAD-derivatized 25-hydroxyvitamin $D_3$ (PTAD-25OHD$_3$).

10. The method of claim 9, wherein said one or more PTAD-derivatized vitamin D metabolite ions comprise ions selected from the group consisting of PTAD-25OHD$_3$ ions with a mass/charge ratio (m/z) of 558.3±0.5 and 298.1±0.5.

11. The method of claim 9, wherein said one or more PTAD-derivatized vitamin D metabolite ions comprise a PTAD-25OHD$_3$ parent ion with a mass/charge ratio (m/z) of 558.3±0.5 and a PTAD-25OHD$_3$ fragment ion with a mass/charge ratio (m/z) of 298.1±0.5.

12. The method of claim 1, wherein said one or more PTAD-derivatized vitamin D metabolites comprises PTAD-derivatized 1,25-dihydroxyvitamin $D_2$ (PTAD-1α,25(OH)$_2$D$_2$).

13. The method of claim 1, wherein said one or more PTAD-derivatized vitamin D metabolites comprises PTAD-derivatized 1,25-dihydroxyvitamin $D_3$ (PTAD-1α,25(OH)$_2$D$_3$).

14. The method of claim 1, wherein said sample comprises plasma or serum.

15. The method of claim 1, wherein steps (ii)-(v) are conducted in an on-line fashion.

\* \* \* \* \*